United States Patent
Pak et al.

(10) Patent No.: US 9,844,605 B2
(45) Date of Patent: Dec. 19, 2017

(54) **TRANSGENIC *CAENORHABDITIS ELEGANS* COMPRISING A HUMAN PROTEIN WITH A TENDENCY TO AGGREGATE FUSED TO A FLUORESCENT PROTEIN**

(71) Applicant: University of Pittsburgh—of the Commonwealth System of Higher Education, Pittsburgh, PA (US)

(72) Inventors: Stephen C. Pak, Pittsburgh, PA (US); David H. Perlmutter, Pittsburgh, PA (US); Gary A. Silverman, Pittsburgh, PA (US)

(73) Assignee: THE UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

(21) Appl. No.: 14/335,413

(22) Filed: Jul. 18, 2014

(65) Prior Publication Data

US 2014/0331341 A1  Nov. 6, 2014

Related U.S. Application Data

(63) Continuation of application No. 12/881,976, filed on Sep. 14, 2010, now Pat. No. 8,809,617.

(60) Provisional application No. 61/258,384, filed on Nov. 5, 2009.

(51) Int. Cl.
| | |
|---|---|
| *A01K 67/00* | (2006.01) |
| *A61K 49/00* | (2006.01) |
| *C07K 14/47* | (2006.01) |
| *A01K 67/033* | (2006.01) |
| *A01K 67/027* | (2006.01) |
| *C12Q 1/68* | (2006.01) |
| *G01N 33/50* | (2006.01) |
| *A61K 35/00* | (2006.01) |

(52) U.S. Cl.
CPC ...... *A61K 49/0008* (2013.01); *A01K 67/0278* (2013.01); *A01K 67/0336* (2013.01); *C07K 14/47* (2013.01); *C12Q 1/6897* (2013.01); *G01N 33/5085* (2013.01); *A01K 2267/0312* (2013.01); *A61K 35/00* (2013.01); *C07K 2319/60* (2013.01); *C12Q 2600/136* (2013.01); *G01N 2500/10* (2013.01)

(58) Field of Classification Search
CPC ............ A01K 67/0336; A01K 67/0278; A01K 2267/0312; A61K 49/0008; A61K 35/00; G01N 2500/10; G01N 33/5085; C12Q 1/6897; C12Q 2600/136; C07K 14/47; C07K 2319/60
See application file for complete search history.

(56) References Cited

U.S. PATENT DOCUMENTS

| | | | |
|---|---|---|---|
| 5,658,900 A | 8/1997 | Boireau et al. | |
| 5,780,483 A | 7/1998 | Widdwson et al. | |
| 8,809,617 B2 | 8/2014 | Pak et al. | |
| 9,072,772 B2 | 7/2015 | Pak et al. | |
| 9,452,171 B2 | 9/2016 | Pak et al. | |
| 2003/0023997 A1* | 1/2003 | Peraus | A01K 67/0336 800/13 |
| 2003/0224508 A1* | 12/2003 | Ill | C07K 14/755 435/320.1 |
| 2004/0213771 A1* | 10/2004 | Sluder | C07K 14/4354 424/94.1 |
| 2005/0160482 A1* | 7/2005 | Blakely | A01K 67/0336 800/3 |
| 2006/0079556 A1 | 4/2006 | Sher et al. | |
| 2006/0141625 A1* | 6/2006 | Sisk | C12N 15/85 435/455 |
| 2007/0275957 A1 | 11/2007 | Weiner et al. | |
| 2009/0054404 A1 | 2/2009 | Fox et al. | |
| 2009/0087916 A1* | 4/2009 | Sato | G01N 33/6896 436/86 |
| 2009/0311786 A1* | 12/2009 | Fire | A61K 48/0066 435/455 |
| 2010/0076018 A1* | 3/2010 | Liu | A61K 31/4741 514/311 |
| 2010/0263062 A1 | 10/2010 | Dillin et al. | |
| 2011/0154510 A1 | 6/2011 | Pak et al. | |
| 2012/0129839 A1 | 5/2012 | Perlmutter et al. | |
| 2014/0047569 A9 | 2/2014 | Pak et al. | |
| 2014/0331341 A1 | 11/2014 | Pak et al. | |

FOREIGN PATENT DOCUMENTS

| | | |
|---|---|---|
| CN | 101023944 | 8/2007 |
| WO | WO 1994/018972 | 9/1994 |
| WO | WO 1996/030766 | 10/1996 |

(Continued)

OTHER PUBLICATIONS

U.S. Appl. No. 14/728,619 (US 2015/0265626), filed Jun. 2, 2015 (Sep. 24, 2015).
U.S. Appl. No. 14/728,619, Nov. 18, 2015 Non-Final Office Action.
U.S. Appl. No. 13/463,638, May 28, 2015 Issue Fee Payment.
U.S. Appl. No. 14/535,210, Nov. 9, 2015 Non-Final Office Action.
U.S. Appl. No. 12/881,976 (US 8,809,617), filed Sep. 14, 2010 (Jun. 23, 2011).
U.S. Appl. No. 13/362,606 (US 2012/0129839), filed Jan. 31, 2012 (May 24, 2012).
U.S. Appl. No. 13/463,638 (US 2014/0047569), filed May 3, 2012 (Feb. 13, 2014).

(Continued)

*Primary Examiner* — Titilayo Moloye
(74) *Attorney, Agent, or Firm* — Baker Botts L.L.P.

(57) ABSTRACT

The present invention relates to methods and compositions for high content drug screening in *Caenorhabditis elegans* which may be used to identify compounds that treat disorders associated with protein aggregation. It is based, at least in part, on the discovery that *Caenorhabditis elegans*, genetically modified to create a model system for disorders of protein aggregation, could be used, in a high throughput screening system, to identify agents that reduce the amount of aggregated protein.

16 Claims, 29 Drawing Sheets

(56) References Cited

FOREIGN PATENT DOCUMENTS

Figure 1A:
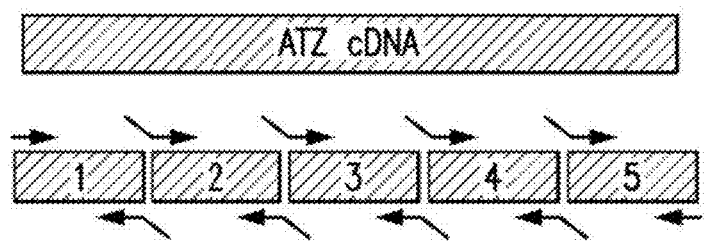

| WO | WO 1998/028971 | | 7/1998 |
|---|---|---|---|
| WO | WO1998028971 | A2 * | 7/1998 |
| WO | WO 1998/048784 | | 11/1998 |
| WO | WO2000063427 | A2 * | 10/2000 |
| WO | WO2000073510 | A1 * | 12/2000 |
| WO | WO2001060840 | A3 * | 8/2001 |
| WO | WO 2002/096431 | | 12/2002 |
| WO | WO 2005/011610 | | 2/2004 |
| WO | WO 2008/030617 | A2 | 3/2008 |
| WO | WO 2008/092898 | A1 | 8/2008 |
| WO | WO 2008/097924 | A2 | 8/2008 |
| WO | WO 2009/036275 | | 3/2009 |
| WO | WO 2009/039284 | A1 | 3/2009 |
| WO | WO 2009/049242 | | 4/2009 |
| WO | WO 2010/085452 | A1 | 7/2010 |

OTHER PUBLICATIONS

U.S. Appl. No. 14/535,210, filed Nov. 6, 2014.
U.S. Appl. No. 12/881,976, Jul. 7, 2014 Issue Fee payment.
U.S. Appl. No. 12/881,976, Apr. 11, 2014 Notice of Allowance.
U.S. Appl. No. 12/881,976, Nov. 25, 2013 Amendment and Request for Continued Examination (RCE).
U.S. Appl. No. 12/881,976, Nov. 7, 2013 Advisory Action.
U.S. Appl. No. 12/881,976, Oct. 21, 2013 Response to Final Office Action.
U.S. Appl. No. 12/881,976, Jul. 19, 2013 Final Office Action.
U.S. Appl. No. 12/881,976, May 13, 2013 Response to Non-Final Office Action.
U.S. Appl. No. 12/881,976, Dec. 11, 2012 Non-Final Office Action.
U.S. Appl. No. 12/881,976, Aug. 13, 2012 Response to Restriction Requirement.
U.S. Appl. No. 12/881,976, Jul. 13, 2012 Restriction Requirement.
U.S. Appl. No. 13/362,606, Nov. 6, 2014 Issue Fee payment.
U.S. Appl. No. 13/362,606, Aug. 15, 2014 Notice of Allowance.
U.S. Appl. No. 13/362,606, Jun. 4, 2014 Response to Non-Final Office Action.
U.S. Appl. No. 13/362,606, Feb. 4, 2014 Non-Final Office Action.
U.S. Appl. No. 13/362,606, Dec. 6, 2013 Response to Restriction Requirement.
U.S. Appl. No. 13/362,606, Nov. 7, 2013 Restriction Requirement.
U.S. Appl. No. 13/463,638, Apr. 29, 2015 Notice of Allowance.
U.S. Appl. No. 13/463,638, Mar. 23, 2015 Response to Office Action.
U.S. Appl. No. 13/463,638, Dec. 29, 2014 Non-Final Office Action.
U.S. Appl. No. 13/463,638, Oct. 30, 2014 Notice of Appeal and Pre-Appeal Brief.
U.S. Appl. No. 13/463,638, Aug. 8, 2014 Advisory Action.
U.S. Appl. No. 13/463,638, Jul. 30, 2014 Response to Final Office Action.
U.S. Appl. No. 13/463,638, May 30, 2014 Final Office Action.
U.S. Appl. No. 13/463,638, May 13, 2014 Response to Non-Final Office Action.
U.S. Appl. No. 13/463,638, Nov. 22, 2013 Non-Final Office Action.
U.S. Appl. No. 13/463,638, Jun. 24, 2013 Response to Restriction Requirement.
U.S. Appl. No. 13/463,638, Jan. 23, 2013 Restriction Requirement.
Ambrósio, et al., "Neurotoxic/neuroprotective profile of carbamazepine, oxcarbazepine and two new putative antiepileptic drugs, BIA 2-093 and BIA 2-024", *Eur. J. Pharmacol.*, 406(2):191-201 (2000).
Arena, et al., "Huntington's Disease: Clinial Effects of a Short-Term Treatment with Pimozide", *Advances in Biochemical Psychopharmacology*, 24:573-575 (1980).
Bauer, et al., "Inhibition of Rho Kinases Enhances the Degradation of Mutant Huntingtin", *The Journal of Biological Chemistry*, 284(19):13153-13164 (2009).
Berger, et al., "Rapamycin alleviates toxicity of different aggregate-prone proteins", *Human Molecular Genetics*, 15(3):433-442 (2006).
Boland, et al., "Autophagy Induction and Autophagosome Clearance in Neurons: Relationship to Autophagic Patology in Alzheimer's Disease", *The Journal of Neuroscience*, 28(27):6926-6937 (2008).
Borowicz, et al., "Acute and Chronic Treatment with Mianserin Differentially Affects the Anticonvulsant Activity of Conventional Antiepileptic Drugs in the Mouse Maximal Electroshock Model", *Psychopharmacolgy*, 195(2):167-174 (2006).
Burton, et al., "Anaesthesia in Elderly Patients with Neurodegenerative Disorders—Special Considerations", *Drugs and Aging*, 21:229-242 (2004).
Cabral, et al., "Processing by Endoplasmic Reticulum Mannosidases Partitions a Secretion-impaired Glycoprotein into Distinct Disposal Pathways", *The Journal of Biological Chemistry*, 275(32):25015-25022 (2000).
Carlson, et al., "Multiple Tissues Express $Alphas_1$-Antitrypsin in Transgenic Mice and Man", *J. Clin. Invest.*, 82(1):26-36 (1988).
Carlson, et al., "Accumulation of PiZ $\alpha_1$-Antitrypsin Causes Liver Damage in Transgenic Mice", *J. Clin. Invest*, 83:1183-1190 (1989).
Chaudhuri et al., "Protein-misfolding diseases and chaperone-based therapeutic approaches", *FEBS Journal*, 273:1331-1349 (2006).
Cohen, et al., "Anti-Amyloid Effects of Small Molecule Aβ-Binding Agents in PS1/APP Mice", *Lett. Drug Des. Discov.*, 6(6):437 (2009).
Cohen, et al., "Reduced IGF-1 Signalling Delays Age-Associated Proteotoxicity in Mice", *Cell*, 139(6):1157-1169 (2009).
Cui, et al., "Role of glutathione in neuroprotective effects of mood stabilizing drugs lithium and valproate", *Neurosocience*, 144(4):1447-1453 (2006).
Dollinger, et al., "A chimeric Ligand Approach Leading to Potent Antiprion Active Acridine Derivatives: Design, Synthesis, and Biological Investigations", *Journal of Medicinal Chemistry*, 49(22):6591-6595 (2006).
Feng, et al., "Small-molecule aggregates inhibit amyloid polymerization", *Nature Chemical Biology*, 4:197-199 (2008).
Filali, et al., "Age-related cognitive decline and nesting behavior in an APPswe/PS1 bigenic model of alzheimer's disease", *Brain Res.*, 1292:93-99 (2009).
Frey, et al., "Transient cholestatic hepatitis in a neonate associated with carbamazepine exposure during preganancy and breast-feeding", *Eur J. Pediatr.*, 150(2):136-138 (1990).
Gao, et al., "Carbamazepine induction of apoptosis in cultured cerebellar neurons: effects of N-methyl-D-aspartate, aurintricarboxylic acid and cycloheximide", *Brain Res.*, 703(1-2):63-71 (1995).
Gong, et al., "Persistent improvement in synaptic and cognitive functions in an alzheimer mouse model after rolipram treatment", *The Journal of Clinical Investigation*, 114:1624-1634 (2004).
Gosai, et al., "Automated High-Content Live Animal Drug Screening Using C. elegans Expressing the Aggregation Prone Serpin $\alpha 1$-Antitrypsin Z", *PLoS One*, 5911):e15460 (2010).
Grant, et al., "Oxcarbazepine. a review of its pharmacology and therapeutic potential in epilepsy, trigeminal neuralgia and affective disorders", *Drugs*, 43(6):873-888 (1992).
Grieco, et al., "Fatty liver and drugs", *Eur Rev Med Pharmacol Sci.*, 9(5):261-263 (2005).
Haas, et al., "Soluble protein oligomers in neurodegeneration: lessons from the Alzheimer's amyloid beta-peptide", *Nat. Rev. Mol. Cell Biol.*, 8(2):101-112 (2007).
Harada, et al., "Autophagy Activation by Rapamycin Eliminates Mouse Mallory-Denk Bodies and Blocks Their Proteasome Inhibitor-Mediated Formation", *Hepatology*, 47(6):2026-2035 (2008).
Hidvegl, et al., An Autophagy-Enhancing Drug Promotes Degradation of Mutant $\alpha_1$-antitrypsin Z and Reduces Hepatic Fibrosis, *Science*, 329:229-232 (2010).
Hidvegl, et al., "Regulator of G signalling 16 is a marker for the distinct endoplasmic reticulum stress state associated with aggregated mutant $\alpha_1$-antitrypsin Z in the classical form of $\alpha_1$-antitrypsin deficiency", *The Journal of Biological Chemistry*, 282(38):27769-27780 (2007).
Hidvegl, et al., "Accumulation of Mutant $\alpha_1$-Antitrypsin Z in the Endoplasmic Reticulum Activates Caspases-4 and -12, NFκB, and

(56) References Cited

OTHER PUBLICATIONS

BAP31 but not the Unfolded Protein Response", *The Journal of Biological Chemistry*, 280(47):39002-39015 (2005).
Holcomb, et al., "Behavioral changes in transgenic mice expressing both amyloid precursor protein and presenilin-1 mutations: lack of association with amyloid deposits", *Behav. Genet.*, 29(3):177-185 (1999).
Hosokawa, et al., "Generation of cell lines with tetracycline-regulated autophagy and a role for autophagy in controlling cell size", *FEBS Letters*, 580(11):2623-2629 (2006).
International Search Report for PCT/US2010/044243, dated Sep. 30, 2010.
International Search Report for PCT/US2010/002898, dated Jan. 31, 2011.
Juruena, et al., "Bipolar I and II disorder residual symptoms: oxcarbazepine and carbamazepine as add-on treatment to lithium in a double-blind, randomized trial", *Prog. Neuropsychopharmacol Biol. Psychiatry*, 33(1):94-99 (2009).
Kamimoto, et al., "Intracellular inclusions containing mutant alpha1-antitrypsin Z are propagated in the absence of autophagic activity", *The Journal of Biological Chemistry*, 281(7):4467-4476 (2006).
Kirkin, et al., "A role for ubiquitin in selective autophagy", *Mol. Cell.*; 34(3):259-269 (2009).
Korenyi, et al., "Drug Treatment in 117 Cases of huntington's Disease with Special Reference to Fluphenazine (Prolixin)", *Psychiatric Quarterly*, 41:203-210 (1967).
Kruse, et al., "Characterization of an ERAD Gene as VPS30/ATG6 Reveals Two Alternative and Functionally Distinct Protein Quality Control Pathways: One for Soluble Z Variant of Human α-1 Proteinase Inhibitor (A1PiZ) and Another for Aggregates of A1PiZ", *Molecular Biology of the Cell*, 17(1):203-212 (2006).
Lawless et al., "Endoplasmic reticulum stress—A double edged sword for Z alpha-1 antitrypsin deficiency hepatoxicity", *The International Journal of Biochemistry & Cell Biology*, 40:1403-1414 (2008).
Lee, et al., "Protein Folding and Diseases", *Journal of Biochemistry and Molecular Biology*, 38:275-280 (2005).
Lin, et al., "A Naturally Occuring nonpolymerogenic Mutant of α1-Antitrypsin Characterized by Prolonged Retention in the Endoplasmic Reticulum", *The Journal of Biological Chemistry*, 276(36):33893-33898 (2001).
Loberts, et al., "Additivity of Dilantin and Vinblastine Inhibitory Effects on Microtubule Assembly", *Cancer Research*, 59(19):4816-4822 (1999).
Lomas, et al., "The mechanism of Z alpha 1-antitrypsin accumulation in the liver", *Nature*, 357(6379):605-607 (1992).
Luef, et al., "Non-alcoholic fatty liver disease (NAFLD), insulin resistance and lipid profile in antiepileptic drug treatment", *Epilepsy Res.*, 86(1):42-47 (2009).
Maeda, et al., "IKKβ is required for prevention of apoptosis mediated by cell-bound but not by circulating TNFα", *Immunity*, 19(5):725-737 (2003).
Mizushima, et al., "How to Interpret LC3 Immunoblotting", *Autophagy*, 3(6):542-545, (2007).
Mizushima, et al., "Autophagy fights disease through cellular self-digestion", *Nature*, 451(7182):1069-1075 (2008).
Naisbitt, et al., "Hypersensitivity Reactions to carbamazepine: Characterization of the Specificity, Phenotype, and Cytokine Profile of Drug-Specific T Cells Clones", *Molecular Pharmacology*, 63(3):732-741 (2003).
Nixon, "Autophagy, amyloidogenesis and Alzheimer diease", *Journal of Cell Science*, 120(Pt 23):4081-4091 (2007).
Österreicher, et al., "Angiotensin-Converting-Enzyme 2 Inhibits Liver Fibrosis in Mice", *Hepatolgy*, 50:929-938 (2009).
Oury, et al., "Attenuation of Bleomycin-Induced Pulmonary Fibrosis by a Catalytic Antioxidant Metalloporphyrin", *Am. J. Respir. Cell Mol. Biol.*, 25(2):164-169 (2001).

Pan, et al., "SNP-mediated translational suppression of ERManl modifies the onset of end-stage liver disease in alpha1-antitrypsin defiency", *Hepatology*,50(1):275-281 (2009).
Paranjpe, et al., "Cell cycle effects resulting from inhibition of hepatocyte growth factor and its receptor c-Met in regenerating rat livers by RNA interference", *Hepatology*, 45(6):1471-1477 (2007).
Perlmutter et al., FASEB Summer Research Conferences, From unfolded proteins in the endoplasmic reticulum to disease, "Acummulation of an aggregation-prone protein in the ER causes liver disease in α1-antitrypsin deficiency", Abstract, (Jun. 7-12, 2009).
Perlmutter, ., "Accumulation of an aggregation-prone mutant protein in the endoplasmic reticulum causes liver disease in alpha-1-antitrypsin deficiency: The role of autophagy and other intracellular disposal pathways", Presentation, National Institute of Diabetes & Digestive and Kidner Diseases Workshop, Bethesda, MD, Jan. 29, 2009.
Perlmutter, "Alpha-1 antitrypsin deficiency: an Aggregation-prone protein causes childhood liver disease". Presentation, Howard Rappaport Memorial Lecture, Pediatric Grand Rounds, Mt. Sinai School of Medicine, New York, NY, Feb. 26, 2009.
Perlmutter, "Alpha-1-Antitrypsin Deficiency: Liver Inflammation and Carcinoma from Aggregation-prone Protein," Presentation, Pediatric Grand Rounds, University of California, San Diego, CA, Mar. 19, 2009.
Perlmutter, "Alpha-1-Antitrypsin Deficiency: Childhood Liver Disease from an Aggregation-prone Protein," Presentation, Pediatric Grand Rounds, Children's Hospital, Boston, MA, May 20, 2009.
Perlmutter, "Autophagic Disposal of the Aggregation-Prone Protein that Causes Liver Inflammation and Carcinogenesis in α-1-antitrypsin Deficiency", *Cell Death and Differentiation*, 16(1):39-45 (2009).
Perlmutter, et al., "The role of autophagy in Alpha-1-Antitrypsin deficiency: A specific cellular response in genetic diseases associated with aggregation-prone proteins", *Autophagy*, 2(4):258-263 (2006).
Pickford, et al., "The autophagy-related protein beclin 1 shows reduced expression in early Alzheimer disease and regulates amyloid β accumulation in mice", *The Journal of Clinical Investigation*, 118(6):2190-2199 (2008).
Piitulainen, et al., "Alpha1-antitrypsin deficiency in 26-year-old sugjects: lung, liver, and protease/protease inhibitor studies", *Chest.*, 128(4):2076-2081 (2005).
Powers, et al., "Biological and Chemical Approaches to Diseases of Proteostasis Defiency", *Annual Review of Biochemistry*, 78:959-991 (2009).
Qu, et al., "Degradation of a Mutant Secretory Protein, $α_1$-antitrypsin Z, in the Endoplasmic Reticulum Requires Proteasome Activity", *The Journal of Biological Chemistry*, 271(37):22791-22795 (1996).
Ramirez, et al., "Prevention of Alzheimer's Disease Pathology by Cannabinoids: Neuroprotection Mediated by Blockade of Microglial Activation", *The Journal of Neuroscience*, 25:1904-1913 (2005).
Ravikumar, et al., "Clearance of mutant aggregate-prone proteins by autophagy", *Methods Mol. Biol.*, 445:195-211 (2008).
Rudnik, et al., "Analyses of hepatocellular proliferation in a mouse model of alpha-1-antitrypsin deficiency", *Hepatology*, 39(4):1048-1055 (2004).
Sarkar,et al., "Lithium induces autophagy by inhibiting inositol monophosphatase", *The Journal of Cell Biology*, 170(7):1101-1111 (2005).
Sarkar, et al., "Small molecules enhance autophagy and reduce toxicity in Huntington's disease models", *Nat. Chem Biol.;* 3(6):331-338 (2007).
Schmidt, et al., "Grp78, Grp94, and Grp170 interact with α1-antitrypsin mutants that are reatined in the endoplasmic reticulum", *Am J. Physiol Gastrointest Liver Physiol.*, 289:G444-G455 (2005).
Seki, et al., "CCR2 Promotes Hepatic Fibrosis in Mice", *Hepatology*, 50:185-197 (2009).
Sifers, "Medicine. Clearing conformational disease", *Science*, 329(5988):154-155 (2010).

(56) References Cited

OTHER PUBLICATIONS

Stepanović-Petrović, et al., "The Antinociceptive Effects of anticonvulsants in a Mouse Visceral Pain Model", *Anesthesia & Analgesia*, 106(6):1897-1903 (2008).
Strang, "Imipramine in treatment of Parkinsonism: A double-Blind Placebo Study", *British Medical Journal*, 2(5452):33-34 (1965).
Teckman, et al., "Mitochondrial autophagy and injury in the liver in $\alpha_1$-antitrypsin defiency", *Am J Physiol Gastrointest Liver Physiol*, 286(5):G851-G862 (2004).
Teckman, et al., "Retention of mutant $\alpha_1$-antitrypsin Z in endoplasmic reticulum is associated with an autophagic response", *Am J Physiol Gastrointest Liver Physiol*, 279(5):G961-G974 (2000).
Teckman, et al., "Fasting in $\alpha_1$-antitrypsin deficient liver: constitutive activation of autophagy", *Am J Physiol Gastrointest Liver Physiol*, 283(5):G1156-G1165 (2002).
Wu, et al., "A lag in intracellular degradation of mutant $\alpha 1$-antitrypsin correlates with the liver disease phenotype in homozygous PiZZ $\alpha 1$-antitrypsin deficiency", *PNAS*, 91(19):9014-9018 (1994).
Zhang, et al., "Small molecule regulators of autophagy identified by an image-based high-throughput screen", *PNAS*, 104(48):19023-19028 (2007).
Zhang, et al., "Microtubule-binding drugs offset tau sequestration by stabilizing microtubules and reversing fast axonal transport deficits in a tauopathy model", *Proceedings of the National Academy of Sciences*, 102:227-231 (2005).
Balch et al., "Adapting proteostasis for disease intervention", *Science*, Feb. 15, 2008, vol. 319: 916-919.
Bleicher et al., "Hit and lead generation: Beyond high-throughput screening", Nature Reviews, May 2003, vol. 2: 369-378.
Bossle et al., "Synthesis and Biological Activity of New 2-Substituted Analogs of Fluphenazine", J Med Chem. 19(3), 370-373 (1976).
Breger et al., "Anti-fungal chemical compounds indentified using a C. elegans pathogenicity assay", PloS Pathogens, Feb. 2007, 3(2) e18: 0168-0178.
Brideau et al., "Improved statistical methods for hit selection in high-throughput screening", The Society for Biomolecular Screening, 2003, 8(6): 634-647.
Chao et al., "Structure-guided synthesis of tamoxifen analogs with improved selectivity for the orphan ERRγ", Bioorg. Med Chem. Lett. 16(4), 821-824 (2006).
Driscoll et al., "The mec-4 gene is a member of a family of *Caenorhabditis elegans* genes that can mutate to induce neuronal degeneration", Nature, Feb. 14, 1991, vol. 349: 588-593.
Dycaico et al., "Neonatal hepatitis induced by a1-Antitrypsin: A transgenic mouse model", Science, Dec. 9, 1988, vol. 242: 1409-1412.
Ellerbrock et al., "Screening for presenilin inhibitors using the free-living nematode, Caenorhabditis elegans", The Society for Biomolecular Screening, 2004, 9(2): 147-152.
Faber et al., "Polyglutamine-mediated dysfunction and apoptotic death of a Caenorhabditis elegans sensory neuron", Proc. Natl. Acad Sci. USA, Jan. 1999, vol. 96: 179-184.
Frearson et al., "HTS and hit finding in academia—from chemical genomics to drug discovery", *Drug Discovery Today*, Dec. 2009, 14(23/24): 1150-1158.
Giuliano et al., "Advances in high content screening for drug delivery", ASSAY and Drug Development Technologies, 2003, 1(4): 565-577.
Gleeson et al., "AD MET rules of thumb II: A comparison of the effects of common substituents on a range of ADMET parameters", Bioorganic & Medicinal Chemistry, 2009, vol. 17: 5906-5919.
Gleeson, "Generation of a set of simple, interpretable ADMET rules of thumb", J Med Chem., 2008, vol. 51: 817-834.
Grover et al., "Differential Effects of Paclitaxel (Taxol) Analogs Modified at Positions C-2, C-7, and C-3' on Tubulin Polymerization and Polymer Stabilization: Identification of a Hyperactive Paclitaxel Derivative†", Biochemistry 34, 3927-3934 (1995).
Haney et al., "High-content screening moves to the front of the line", Drug Discovery Today, Oct. 2006, 11 (19/20): 889-894.
Hirata et al., "Potential CNS Antitumor Agents-Phenothiazines II: Fluphenazine Analogs" J Pharm. Sci. 67(2), 157-162 (1978).
Hodgson, "ADMET-tuming chemicals into drugs", Nature Biotechnology, Aug. 2001, vol. 19: 722-726.
Hoffner et al., "Protein Aggregation in Huntington's Disease", Biochimie, 84:273-278 (2002).
Johnston et al., "Cdc25B dual-specificity phosphatase inhibitors identified in a high throughput screen of the NIH compound library", ASSAY and Drug Development Technologies, Jun. 2009, 7(3): 250-265.
Johnston et al., "Development and implementation of a 384-Well homogeneous fluorescence intensity high-throughput screening assay to identify mitogen-activated protein kinase phosphatase-I dual-specificity protein phosphatase inhibitors", ASSAY and Drug Development Technologies, 2007, 5(3): 319-332.
Johnston et al., "Development of a 384-Well colorimetric assay to quantify hydrogen peroxide generated by the redox cycling of compounds in the presence of reducing agent", ASSAY and Drug Development Technologies, 2008, 6(4): 505-518.
Johnston et al., "HTS identifies novel and specific uncompetitive inhibitors of the twocomponent NS2B-NS3 proteinase of west Nile virus", ASSAY and Drug Development Technologies, 2007, 5(6): 737-750.
Kang et al., "Dual roles of autophagy in the survival of Caenorhabditis elegans during starvation", Genes and Development, 2007, vol. 21: 2161-2171.
Kok et al., "Induction of apoptosis on carcinoma cells by two synthetic cantharidin analogues", Int. J Mal. Med 17(1), 151-157 (2006).
Kopito et al., "Conformational Disease", Nature Cell Biology, 2:E207-E209 (2000).
Kruse et al., "Characterization of an ERAD gene asVPS30/ATG6 reveals two alternative and functionally distinct protein quality control pathways: One for soluble Z variant of human a-1 proteinase inhibitor (AlPiZ) and another for aggregates of AlPiZ", Molecular Biology of the Cell, Jan. 2006, vol. 17: 203-212.
Kwok et al., "A small-molecule screen in C. elegans yields a new calcium channel antagonist", Nature, May 2006, vol. 441: 91-95.
Lee et al., "High-content screening: Emerging hardware and software technologies", Methods in Enzymology, 2006, vol. 414: 468-483.
Link, "Expression of human β-amyloid peptide in transgenic Caenorhabditis elegans", Proc. Natl. Acad Sci. USA, Sep. 1995, vol. 92: 9368-9372.
Luke et al., "An intracellular serpin regulates necrosis by inhibiting the induction and sequelae of lysosomal injury", Cell, Sep. 21, 2007, vol. 130: 1108-1119.
Lum et al., "Autophagy in metazoans: Cell survival in the land of plenty", Nature Reviews/Molecular Cell Biology, Jun. 2005, vol. 6: 439-448.
Malo et al., "Statistical practice in high-throughput screening data analysis", Nature Biotechnology, Feb. 2006, 24(2): 167-175.
Martin et al., "Therapeutic perspectives for the treatment of Huntington's disease: Treating the whole body", Histol Histopathol., 23(2):237-250 (2008).
Mayr et al., "Novel trends in high-throughput screening", Current Opinion in Pharmacology, 12009, vol. 9: 580-588.
McCluskey et al., "The First Two Cantharidin Analogues Displaying PP1 Selectivity", Bioorganic & Medicinal Chemistry Letters 12(3):391-393 (2002).
Melendez et al., "Autophagy genes are essential for dauer development and life-span extension in C elegans", Science, Sep. 5, 2003, vol. 301: 1387-1391.
Molina et al., "Zebrafish chemical screening reveals an inhibitor of Dusp6 that expands cardiac cell lineages", Nature Chemical Biology, Sep. 2009, 5(9): 680-687.
Morley et al., "The threshold for polyglutamine-expansion protein aggregation and cellular toxicity is dynamic and influenced by aging in Caenorhabditis elegans", PNAS, Aug. 6, 2002,99(16): 10417-10422.

(56) References Cited

OTHER PUBLICATIONS

Moy et al., "High-throughput screen for novel antimicrobials using a whole animal infection model", ACS Chemical Biology, 2009, 4(7): 527-533.
Moyna et al., "Conformational Studies of Paclitaxel Analogs Modified at the C-2' Position in Hydrophobic and Hydrophilic Solvent Systems", J Med Chem. 40(20), 3305-3311 (1997).
Nehrke et al., "The NHX family of Na+—H+exchangers in Caenorhabditis elegans", The Journal of Biological Chemistry, Aug. 9, 2002, 277(32): 29036-29044.
Nehrke, "A reduction in intestinal cell pHi due to loss of the Caenorhabditis elegans Na+/W exchanger NHX-2 increases life span", The Journal of Biological Chemistry, Nov. 7, 2003, 278(45): 44657-44666.
North et al., "Prostaglandin E2 regulates vertebrate haematopoietic stem cell homeostasis", Nature, Jun. 21, 2007, vol. 447: 1007-1011.
Okoli et al., "Identification of antifungal compounds active against Candida albicans using improved high-throughput Caenorhabditis elegans Assay", PloS ONE, Sep. 2009, 4(9) e7025: 1-8.
Parmar et al., "Alpha-1-antitrypsin deficiency, the serpinopathies and conformation disease", JR Coll Physicians Land, 34(3):295-300 (2000) (Abstract only).
Perlmutter, "Liver injury in a α1-antitrypsin deficiency: an aggregated protein induces mitochondrial injury", J Clin. Invest., 2002, vol. 110: 1579-1583.
Petrascheck et al., "An antidepressant that extends lifespan in adult Caenorhabditis elegans", Nature, Nov. 22, 2007, vol. 450: 553-556.
Rihel et al., "Zebrafish behavioral profiling links drugs to biological targets and rest/wake regulation", Science, Jan. 15, 2010, vol. 327: 348-351.
Royal et al., "Temperature-sensitive mutant of the Caenorhabditis elegans neurotoxic MEC-4(d) DEG/EnaC channel identifies a site required for trafficking or surface maintenance", The Journal of Biological Chemistry, Dec. 23, 2005, 280(51): 41976-41986.
Silverman et al., "Modeling molecular and cellular aspects of human disease using the nematode Caenorhabditis elegans", Pediatric Research, 2009, 65(1): 10-18.
Stockwell, "Chemical genetics: Ligand-based discovery of gene function", Nature Reviews/Genetics, Nov. 2000, 1(2): 116-125.
Stoller et al., "α1-antitrypsin deficiency", Lancet, Jun. 25-Jul. 1, 2005: 365(9478): 2225-2236.
Szewczyk et al., "Chemically defined medium and Caenorhabditis elegans", BMC Biotechnology, 2003, 3, 19-eoa.
Thaqi et al., "Synthesis and biological activity of D-5,6-norcantharimides: importance of the Δ5,6-bridge", Eur. J Med Chem. 45(5), 1717-1723 (2010).
Tran et al., "Automated, quantitive screening assay for antiangiogenic compounds using transgenic zebrafish", Cancer Research, Dec. 1, 2007, 67(23): 11386-11392.
Walker et al., "Molecular cloning and heterologous expression of the C-13 phenylpropanoid side chain—CoA acyltransferase that functions in Taxol biosynthesis" Proc. Natl. Acad Sci. USA. 99(20), 12715-12720 (2002).
Werner et al., "Proteasome-dependent endoplasmic reticulum-associated protein degradation: An unconventional route to a familiar fate", Proc. Natl. Acad. Sci. USA, Nov. 1996, vol. 93: 13797-13801.
Williams et al., "Novel targets for Huntington's disease in an mTOR-independent autophagy pathway", Nature Chemical Biology, May 2008, 4(5): 295-305.
Yu et al., "Dorsomorphin inhibits BMP signals required for embryogenesis and iron metabolism", Nature Chemical Biology, Jan. 2008, 4(1): 33-41.
Zhang et al., "A simple statistical parameter for use in evaluation and validation of high throughput screening assays", Journal of Biomolecular Screening, 1999, 4(2): 67-73.
U.S. Appl. No. 15/247,518 (US 2016/0361319), filed Aug. 25, 2016 (Dec. 15, 2016).
U.S. Appl. No. 15/296,247 (US 2017/0049783), filed Oct. 18, 2017 (Feb. 23, 2017).
U.S. Appl. No. 14/535,210, Oct. 18, 2016 Issue Fee Payment.
U.S. Appl. No. 14/535,210, Jul. 27, 2016 Notice of Allowance.
U.S. Appl. No. 14/535,210, Jun. 23, 2016 Request for Continued Examination (RCE).
U.S. Appl. No. 14/535,210, Jun. 7, 2016 Notice of Allowance.
U.S. Appl. No. 14/535,210, Apr. 11, 2016 Response to Non-Final Office Action.
U.S. Appl. No. 14/728,619, Aug. 24, 2016 Issue Fee Payment.
U.S. Appl. No. 14/728,619, May 25, 2016 Notice of Allowance.
U.S. Appl. No. 14/728,619, Mar. 18, 2016 Response to Non-Final Office Action.
U.S. Appl. No. 15/247,518, Apr. 17, 2017 Non-Final Office Action.
U.S. Appl. No. 15/296,247, Mar. 3, 2017 Non-Final Office Action.

* cited by examiner

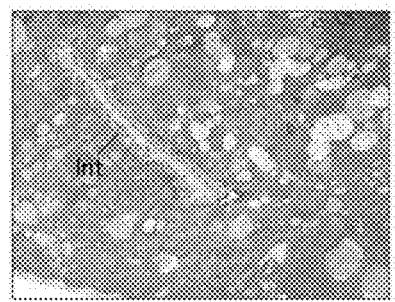 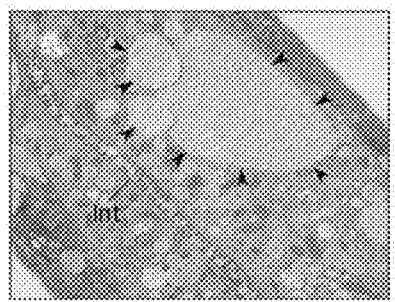
FIG. 4A  FIG. 4B
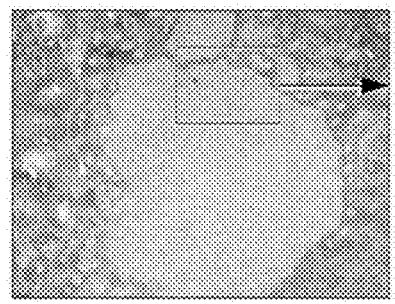 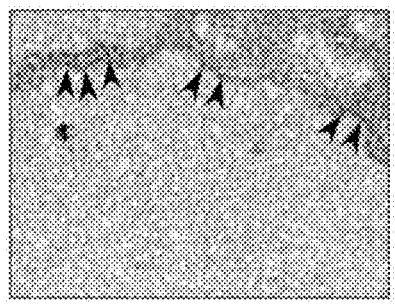
FIG. 4C  FIG. 4D

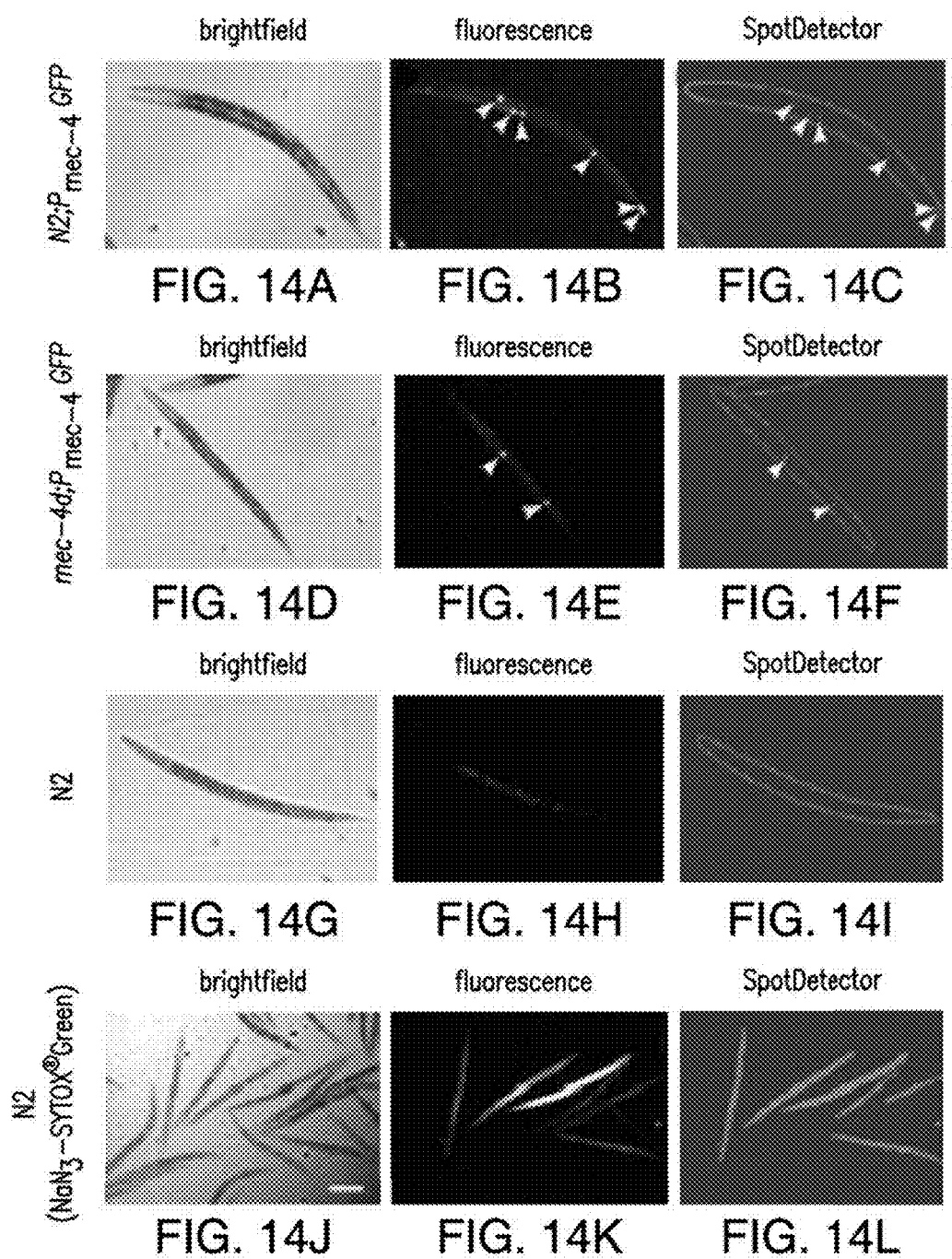

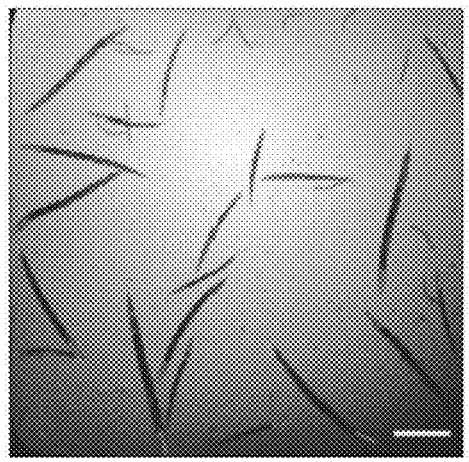
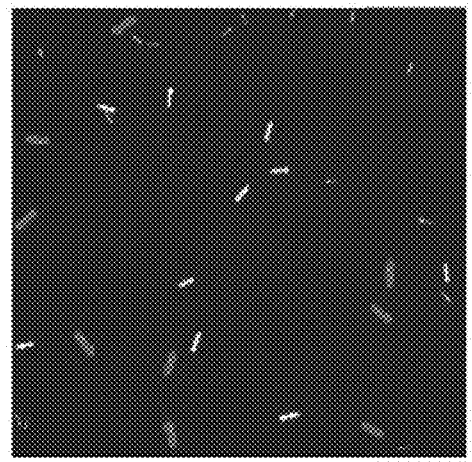
FIG. 15A FIG. 15B
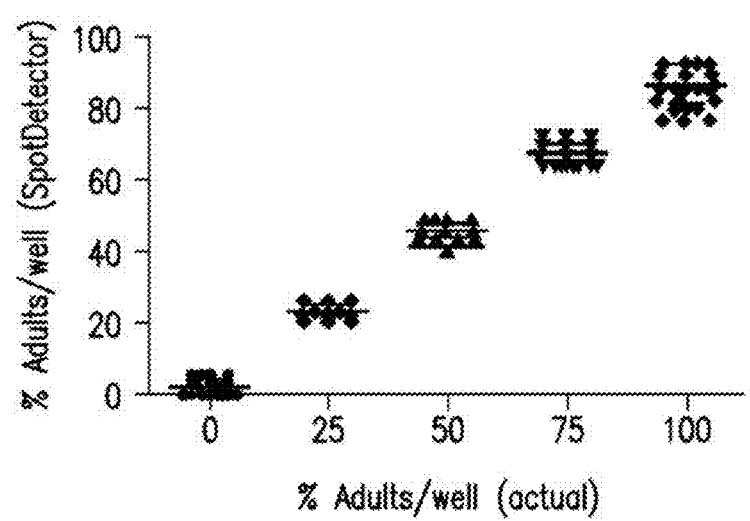
FIG. 15C

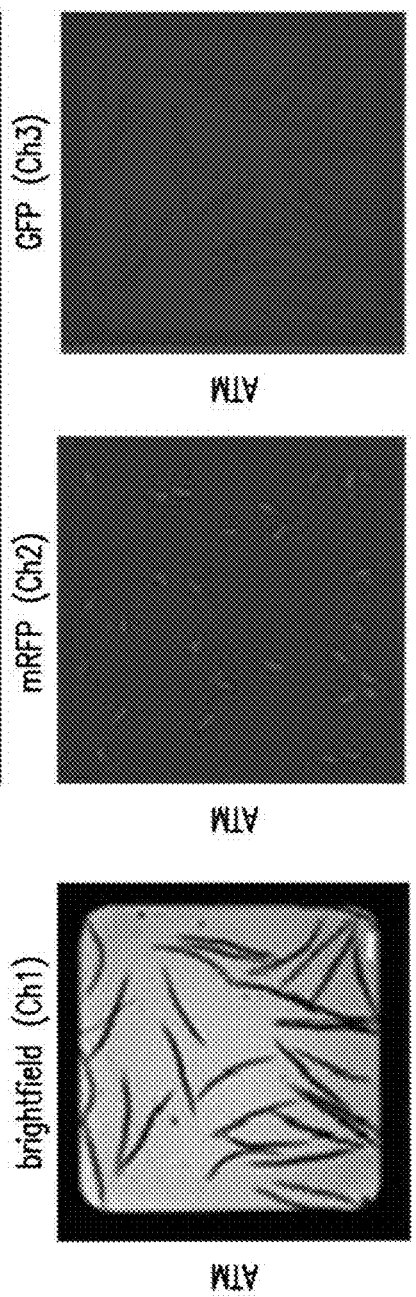
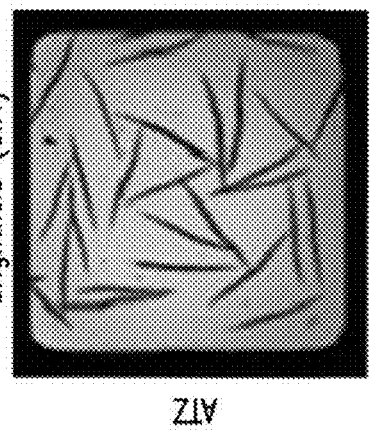
FIG. 16A  FIG. 16B  FIG. 16C
FIG. 16D  FIG. 16E  FIG. 16F

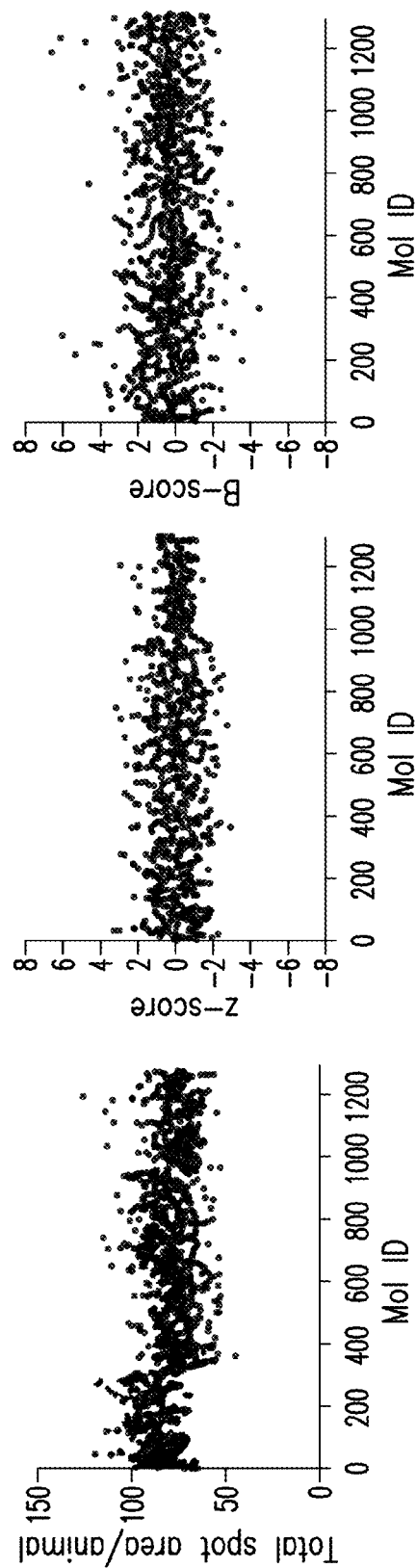

_US 9,844,605 B2_

TRANSGENIC CAENORHABDITIS ELEGANS COMPRISING A HUMAN PROTEIN WITH A TENDENCY TO AGGREGATE FUSED TO A FLUORESCENT PROTEIN

CROSS REFERENCE TO RELATED APPLICATIONS

This application is a continuation of co-pending U.S. patent application Ser. No. 12/881,976, filed Sep. 14, 2010, which claims priority to U.S. Provisional Patent Application No. 61/258,384, filed Nov. 5, 2009, each of which is hereby incorporated by reference in its entirety herein.

GRANT INFORMATION

This invention was made with government support under grant DK079806 awarded by the National Institutes of Health. The government has certain rights in the invention.

1. INTRODUCTION

The present invention relates to methods and compositions for high content drug screening in C. elegans which may be used to identify compounds that treat disorders associated with protein aggregation.

2. BACKGROUND OF THE INVENTION

2.1 Disorders of Protein Aggregation

A number of disorders are associated with the presence of protein aggregates. These disorders may alternatively be referred to as disorders of protein polymerization or of protein misfolding, but are collectively referred to herein as disorders of protein aggregation.

The classical form of α1-antitrypsin ("AT") deficiency is an autosomal co-dominant disorder that affects approximately 1 in 2000 live births (1). It is caused by a point mutation that alters the folding of an abundant liver-derived plasma glycoprotein during biogenesis and also renders it prone to aggregation (2). In addition to the formation of insoluble aggregates in the ER of liver cells, there is an 85-90% reduction in circulating levels of AT, the predominant physiologic inhibitor of neutrophil elastase. Individuals who are homozygous for the mutant allele are susceptible to premature development of chronic obstructive pulmonary disease. Pulmonary involvement is believed to be caused by a loss-of-function mechanism, as lack of AT in the lung permits elastase to slowly destroy the pulmonary connective tissue matrix (3).

AT deficiency is the most common genetic cause of liver disease in children and also causes liver disease and hepatocellular carcinoma in adults. In contrast to pulmonary involvement, liver inflammation and carcinogenesis are believed to be caused by a gain-of-toxic function mechanism. This is most clearly demonstrated by introducing the mutant human ATZ allele as transgene into genetically engineered mice (4,5). Insoluble aggregates in hepatocytes, hepatic inflammation and carcinogenesis evolve even though the endogenous anti-elastases of the transgenic mouse are intact.

Cohort studies from an unbiased Swedish newborn screening program have shown that only 8-10% of the affected homozygous population develop clinically significant liver disease through the first 30 years of life (6). This has led to the concept that genetic and/or environmental modifiers determine whether an affected homozygote is susceptible to, or protected from, liver disease. Furthermore, it has led to consideration of two general explanations for the effects of such modifiers: variation in the function of intracellular degradative mechanisms and/or variation in the signal transduction pathways that are activated to protect the cell from protein mislocalization and/or aggregation.

Studies in this area have so far indicated that the proteasome is responsible for degrading soluble forms of ATZ (7,8) and that macroautophagy is specialized for disposal of the insoluble aggregates that accumulate in the ER (9, 10). In terms of cellular response pathways, it is thought that accumulation of ATZ activates NFκB and autophagy but not the unfolded protein response (11, 12).

Aggregation of protein is associated with a number of other disorders. Among these is Alzheimer's Disease ("AD"), a disorder which affects four million people in the United States and has an incidence estimated at 1 in 68 individuals. As such, AD is the most common form of age-dependent neurodegeneration. Most cases are recognized by the sporadic onset of dementia during the seventh decade of life while the less common, mutation-linked familial cases cause dementia that is recognized by the fifth decade. AD is associated with the accumulation of aggregation-prone peptides in the brain, especially amyloid-β ("Aβ") peptides, but hyperphosphorylated tau proteins also contribute to the tangles and plaques that constitute the histological hallmarks of the disease.

AD is thought to be caused by a gain-of-toxic function mechanism that is triggered by the accumulation of aggregated Aβ and tau and worsened by aging (13). Recent studies have shown that the prevalence of autophagosomes is increased in dystrophic neurons of the AD brain, a finding that is recapitulated in mouse models of the disease (14). Most of the evidence suggests that autophagy plays a role in disposal of aggregated proteins that might have toxic effects on neurons (15, 16). In fact, the neuropathological effects of Aβ in a mouse model of AD were ameliorated by enhancing autophagy via overexpression of the autophagy protein beclin 1 (16). In a study by Cohen et al., breeding of a mouse model of AD to a mouse model with targeted disruption of the IGF-1 receptor demonstrated that reduced IGF-1 signaling blunted and delayed the toxic effect of Aβ accumulation (17). Although this could be attributed in part to sequestration of soluble Aβ oligomers into dense aggregates of lower toxicity, it is well established that IGF-1 signaling inhibits autophagy and therefore that these mice would likely have enhanced autophagy. Thus, based on the current literature, autophagy may be increased in AD, but the load of oligomers may be too great to avoid toxic Aβ accumulation.

Other disorders associated with increased protein aggregates include Parkinson's Disease and Huntington's Chorea. Parkinson's Disease is associated with the presence of protein aggregates in the form of "Lewy Bodies", which contain a number of proteins including one or more of alpha-synuclein, ubiquitin, neurofilament protein, alpha B crystallin and tau protein. Interestingly, a number of other disorders manifested as dementia are also associated with the presence of Lewy Bodies in neurons—these include Alzheimer's Disease, Pick's Disease, corticobasal atrophy, multiple system atrophy, and so-called "dementia with Lewy Bodies" or "DLB". Huntington's Chorea is associated with aggregates of huntingtin protein containing a mutation that results in long tracts of polyglutamine ("polyQ") which result in improper protein processing and aggregate formation. In addition, protein aggregation has been observed in the context of ischemic or traumatic injury, including but not limited to chronic traumatic brain injury.

Recently, Hidvegi et al. have reported that the anticonvulsant drug carbamazepine was able to promote the degradation of ATZ protein in cells and animals manifesting the ATZ mutation, and was observed to decrease the amount of ATZ accumulated in the liver in a mouse model of AT deficiency (18).

2.2 Drug Screening Systems

The development of small-molecule therapeutics via reverse chemical genetic (i.e., target-directed) screens has accelerated, in part, due to the genome-driven discovery of new drug targets, the expansion of natural and synthetic combinatorial chemistry compound collections and the development of high- and ultra high-throughput screening (HTS) technologies (20, 21). Despite these advances, a lead series painstakingly developed in vitro may be abandoned due to the loss of activity or an unfavorable therapeutic index upon testing in mammalian cell cultures, vertebrate animals or phase 1 clinical trials (22, 23). Frequently, attrition of a lead series is due to unfavorable drug absorption, distribution, metabolism, excretion or toxicity (AD-MET) (24, 25).

Some ADMET deficiencies can be avoided, by conducting the initial drug screens in cells. Initially, however, cell-based screening systems suffered from a lack of assay robustness, intensive labor and resource utilization, and low throughput; especially in terms of data acquisition, storage and analysis. The subsequent development of high-content screening (HCS) technologies, which combines automated fluorescence microscopy with quantitative cellular image analysis, has converted cell-based screening into a viable platform for HTS drug discovery campaigns (26). The major advantage of HCS is the simultaneous acquisition of multiple information-rich parameters (e.g., size, shape, granularity and fluorescence intensity) for each cell in culture (27). Temporal and spatial integration of these parameters facilitates the evaluation of compound effects on complex physiological processes such as cell death activation, cell-to-cell contacts, vesicular trafficking and the translocation of fluorescent markers to different subcellular locations (26, 27).

While HCS using cell-based assays facilitate the elimination of compounds that are directly cytotoxic, they are unable to identify those that lose their desired therapeutic effect in vivo, or demonstrate deleterious side effects on complex developmental or physiological processes, such as cellular migration or synaptic transmission, respectively. For this reason, forward chemical genetic screens (i.e., phenotype-directed) using live animals that model human disease phenotypes might serve as suitable alternatives to target-directed reverse chemical screens (28). Drug screens using live organisms provide several distinct advantages over molecular- or cell-based assays and include: 1) the assessment of ADMET characteristics at the earliest stages of the drug discovery process, 2) the identification of leads without detailed knowledge of specific disease-related targets or molecular pathways and 3) the avoidance of ascertainment biases associated with targeting pathways or molecules whose involvement may prove to be tangential to the disease process. Despite these advantages, the assimilation of live animals into drug screening protocols presents logistical challenges. These barriers include labor- and cost-intensive development of suitable disease phenotypes; screening protocols that are low-throughput and unamenable to statistically robust HCS-like formats; and the prohibitive consumption of compound libraries. Over the last several years, however, investigators began adapting small organisms, such as *Caenorhabditis elegans* and *Danio rerio*, to HTS protocols (29-37). Taken together, these studies suggest that organisms dispensed by automated liquid-handling workstations and cultivated in microtiter plates may provide an economical alternative to molecular and cell-based screens. *C. elegans*, in particular, should be an ideal candidate for live animal HCS campaigns, as their tissues are transparent at all developmental stages, the use of fluorescent probes and tissue-specific fluorescent transgenic markers to study physiological processes in vivo are well established, fundamental cell biological processes are highly conserved across species, and aspects of mammalian diseases can be successfully modeled in these invertebrates (reviewed in 38). Nonetheless, experimental variables that affect high-quality HCS protocols, such as sample preparation, assay strategy, and image acquisition, have yet to be optimized for any organism (39).

3. SUMMARY OF THE INVENTION

The present invention relates to methods and compositions for high content drug screening in *C. elegans* which may be used to identify compounds that treat disorders associated with protein aggregation. It is based, at least in part, on the discovery that *C. elegans*, genetically modified to create a model system for disorders of protein aggregation, could be used, in a high throughput screening system, to identify agents that reduce the amount of aggregated protein (in particular, ATZ protein). In preferred embodiments, the assay system of the invention utilizes an all-liquid work-flow strategy that essentially eliminates a major bottleneck in the screening process and fully exploits the advantages of *C. elegans* as a platform for in vivo high-content and high-throughput pre-clinical drug discovery campaigns. According to the invention, adapting an automated system that streamlines the image acquisition and data analysis components to accurately define objects and detect tissue-specific changes using fluorescent markers enables monitoring complex physiological processes and screening for compounds that modulate these processes.

4. BRIEF DESCRIPTION OF THE FIGURES

FIG. 1A-D. Overlap-extension PCR strategy for introducing introns. To optimize expression in *C. elegans*, synthetic introns (~50 bp) were introduced into the ATZ cDNA. (A) Oligonucleotides primers flanked with synthetic intronic sequences (colored) were used to amplify small (~250-350) fragments of the ATZ cDNA. (B) PCR fragments were gel purified and adjacent fragments were incubated for 45 s at 95° C. and 68° C. for 10 cycles in the presence of dNTPs and Pfu DNA polymerase to promote annealing and extension of complementary strands. (C) Agarose gel showing individual PCR fragments (lanes 1-5). Overlap extension products 1+2 (lane 6), 4+5 (lane 7), [1+2]+3 (lane 8), [1+2+3]+[4+5] (lane 9). (D) ATZ with 4 synthetic introns (colored).

FIGS. 2A-E. DIC (left) and fluorescence (right) photomicrographs of transgenic animals. For orientation in each paired set of figures, white arrowheads indicate corresponding basal surfaces of intestinal cells. (A) Adult worm harboring Pnhx-2::GFP shows diffuse intracellular GFP expression within the intestinal cells. (B) and (C) Pnhx-2::sGFP and Pnhx-2::sGFP::ATM transgenic animals secrete GFP into the extracellular pseudocoelomic space (asterisks). Note only background autofluorescent granules (lysosomes) in intestinal cells, but no cytoplasmic GFP at even high integration. (D) Pnhx-2::sGFP::ATZ animals accumulate ATZ "globules" within intestinal cell cytoplasm (red arrowheads) and fail to secrete detectable amounts of fusion protein into the pseudocoelomic space. (E) A second larval (L2) stage, Pnhx-2::sGFP::ATZ animal showing prominent intracellular inclusions of sGFP::ATZ (red arrowheads) that are comparable to those of the adult. In some animals, a second type of granule was seen occasionally (blue arrowheads). The subcellular location of this granule has not yet been identified.

Figure 3A:
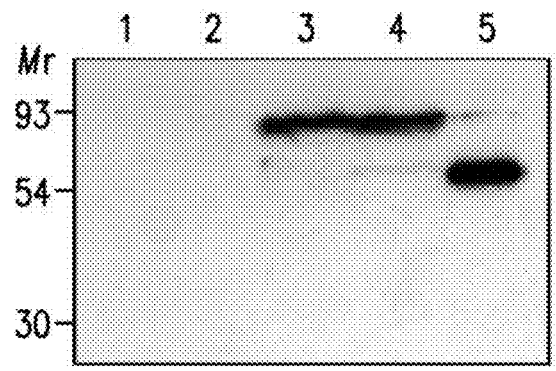
Figure 3B:
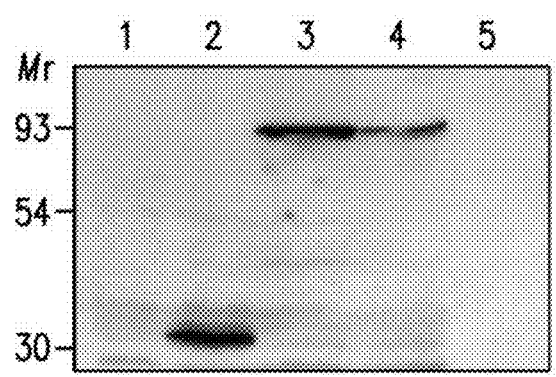

FIG. 3A-B. Immunoblot of worm lysates after SDS-PAGE. Immunoblots were probed with anti-human AT (A) and anti-GFP (B) antibodies. Lane 1, N2; lane 2, Pnhx-2::sGFP; lane 3, Pnhx-2::sGFP::ATM; lane 4, Pnhx-2::sGFP::ATZ; lane 5, purified plasma AT standard.

FIG. 4A-D. Electron micrographs of ATZ globule-containing intestinal cells of transgenic worms. Cross and transverse sections of early larval stage worms expressing sGFP::ATM (A) or sGFP::ATZ (B) transgenes. Arrowheads point to large intracellular inclusions similar to those found in ATZ liver. A close-up of another ATZ inclusion (C). A higher magnification of the boxed area is shown in (D). Arrowheads point to ribosomes of the dilated ER. Int, intestinal lumen.

Figure 5:
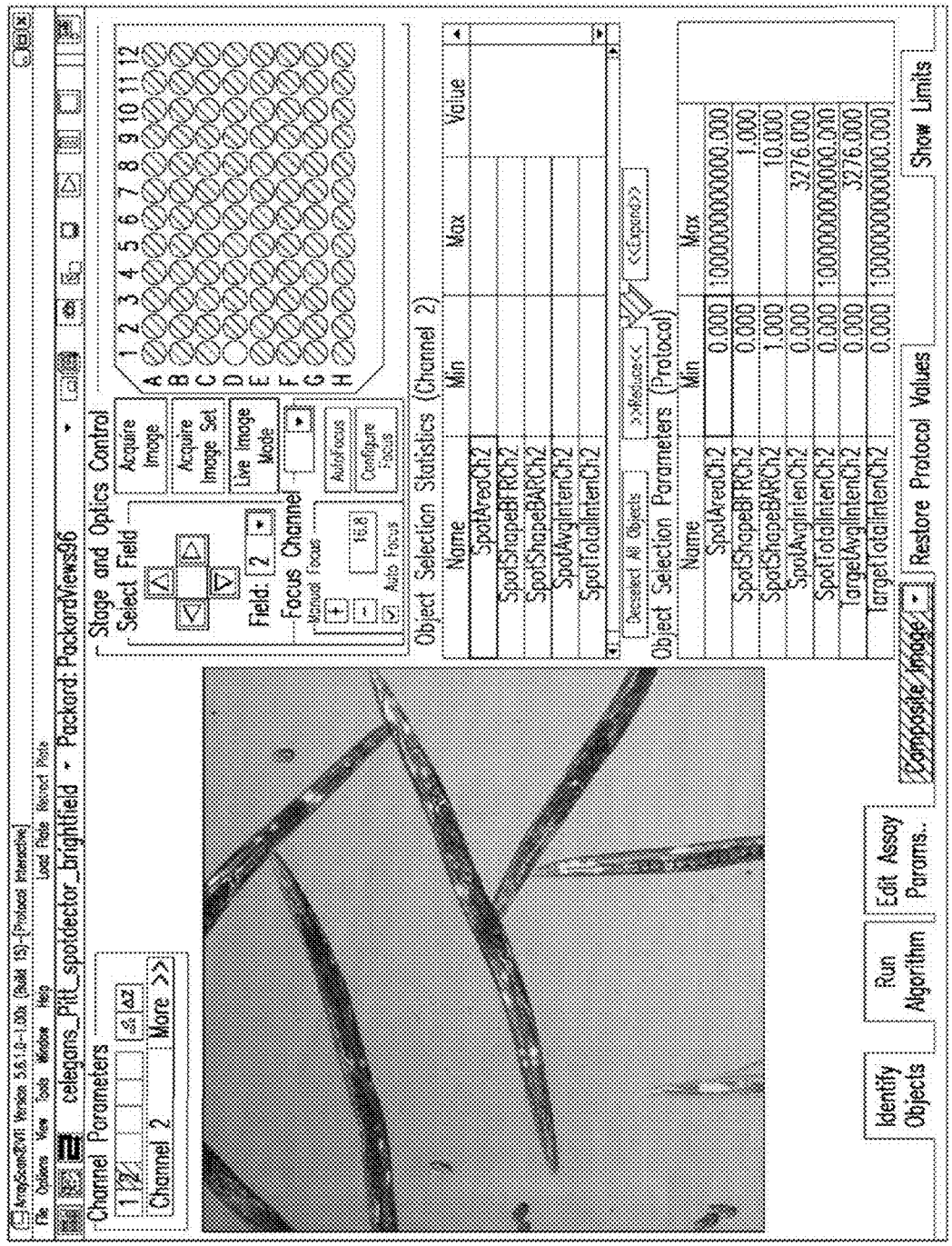

FIG. 5. ArrayScanVTi screen shot interface. Bright field and fluorescent image of sGFP::ATZ animals in one of four fields from well D1.

Figure 6:
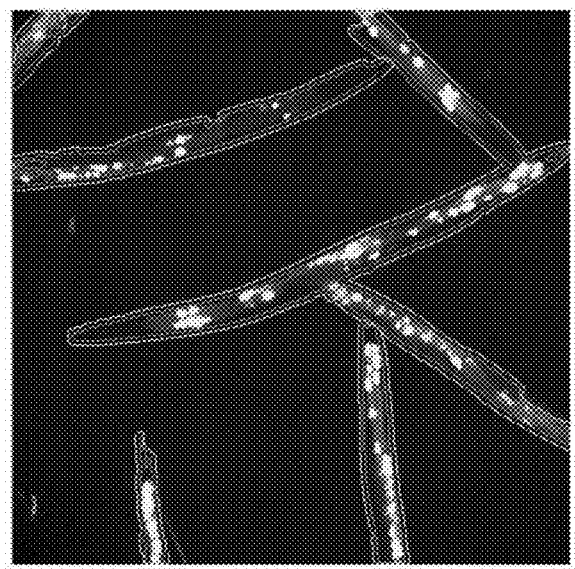

FIG. 6. Detection of worm boundaries and ATZ aggregates. Objects (blue outline) and spots (red dots) selected) by the ArrayScanVTi algorithms. Only these selected elements were used for subsequent data analysis (see FIGS. 7 and 8).

Figure 7:
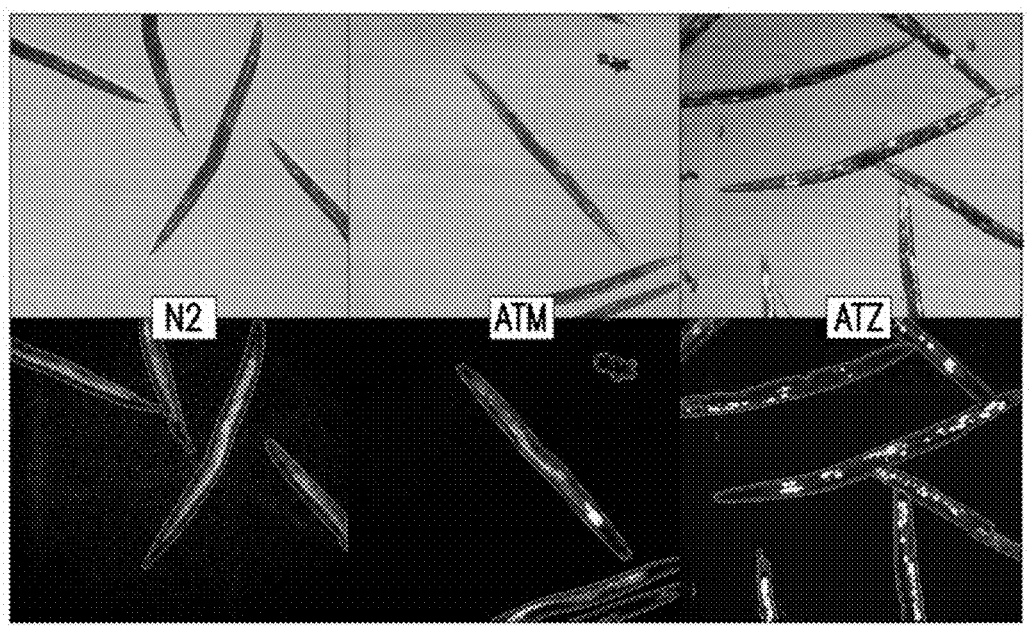

FIG. 7. Detection of fluorescent "aggregates" in N2, sGFP::ATM and sGFP::ATZ worms. Top images are merged bright field and GFP fluorescence images (top) were analyzed quantitatively for size and number of fluorescent "aggregates" (bottom). The algorithm does not distinguish between GFP in the pseudocoelomic space (sGFP::ATZ animals) and GFP in actual inclusions (sGFP::ATZ). However, these GFP collections vary significantly in size and number, which permits discrimination between the transgenic lines. See FIG. 8 for analysis.

Figure 8A:
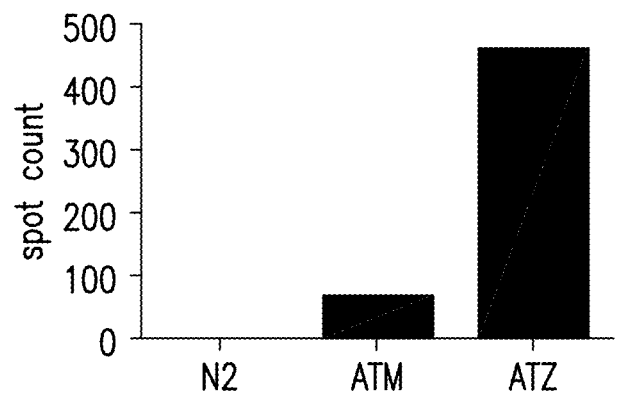
Figure 8B:
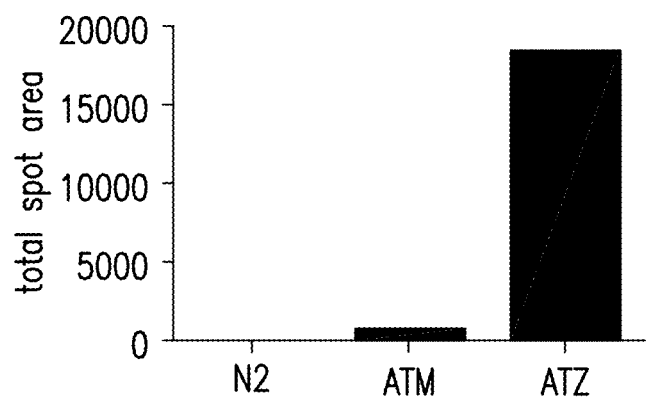
Figure 8C:
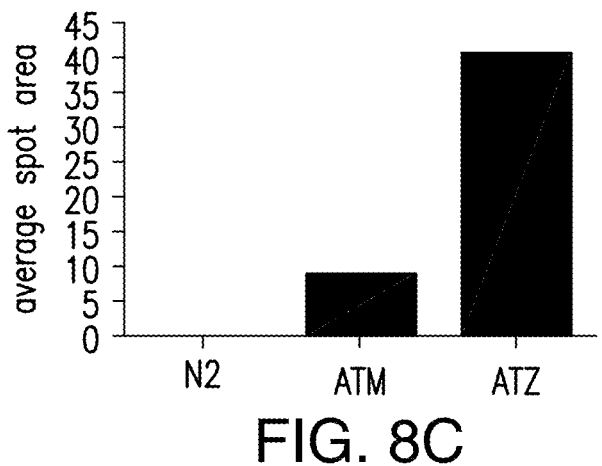

FIG. 8A-C. Comparison of aggregate number (A), total aggregate area (B) and average aggregate size (C) in N2, sGFP::ATM (red) and sGFP::ATZ (blue) animals. Data were derived from those animals shown in FIG. 7.

Figure 9:
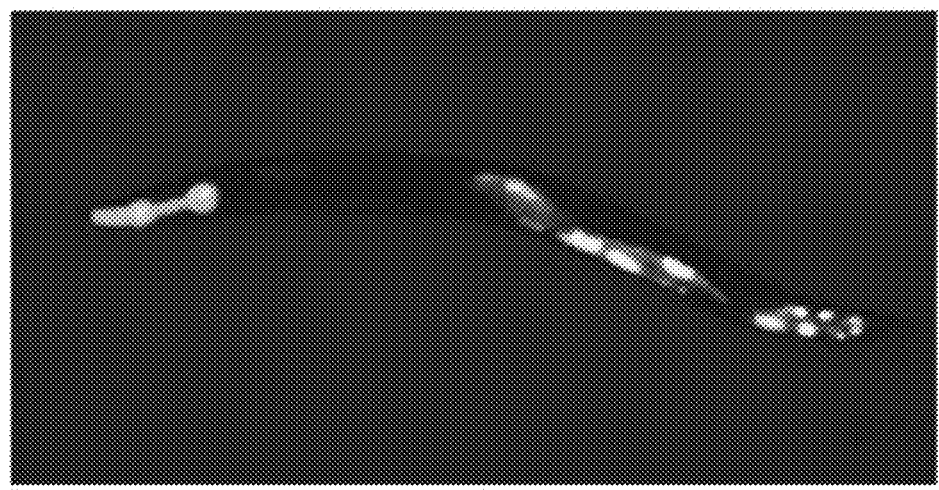
Figures 10A, 10B, 10C, 10D, 10E:
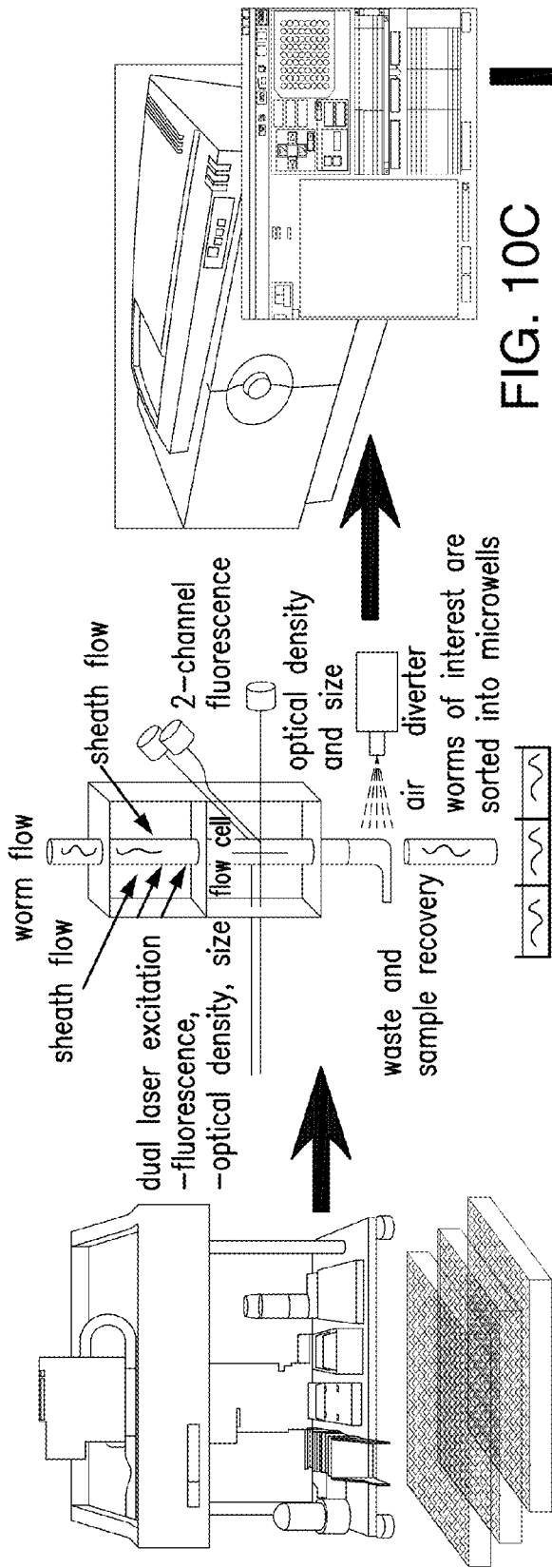

FIG. 9. New improved transgenic line with mCherrry expression in the head region.

FIG. 10A-E. Global strategy for high-throughput screening of lead compounds that alter ATZ aggregation. (A) Compounds, media and E. coli are dispensed into 96-well plates using a high-throughput robotic liquid handler. (B) Worms are sorted based on size and GFP fluorescence and automatically transferred into 96-well plates. (C) An automated high-throughput microscopic imaging system captures images and converts them into numerical data that identifies changes in aggregate number, size and intensity. (D) Lead compounds are identified and further scrutinized to confirm positives and eliminate nuisance compounds. (E) New compounds are synthesized to develop potential therapeutics.

Figure 11:
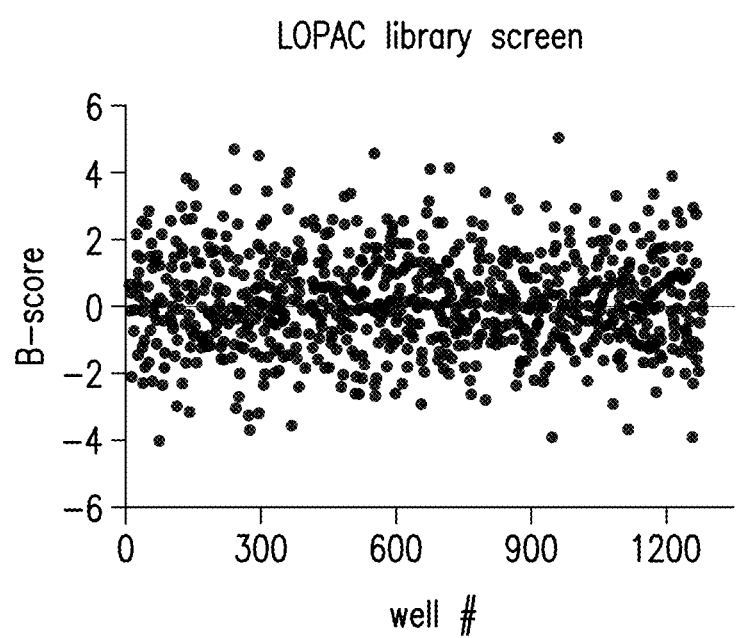

FIG. 11. B-score analysis of LOPAC compounds.

FIG. 12A-E. Animal (object) detection using the ArrayScan $V^{TI}$. Thirty-five adult or mixed stage animals were dispensed into 384-well plates, imaged and analyzed using the ArrayScan $V^{TI}$ and SpotDetector BioApplication. (A) A brightfield image of adult animals. (B) SpotDetector correctly identified all the worms in the field as indicated by the blue outline. (C) A representative brightfield image of a well containing 36 animals with a predetermined percentage (0, 25, 50, 75 and 100%) of adults sorted into a 384-well plate. (D) SpotDetector was optimized to identify large (L4 and adult stage) worms (blue outline) and exclude smaller (L1, L2 and L3 stage) worms (orange outline). (E) Correlation between the percent of adults actually sorted per well in d vs. the percent of adults as determined by SpotDetector. The slope and goodness-of-fit ($r^2$) of the linear regression were 0.72 and 0.85, respectively. The slope of the line was significantly different to 1 ($P<0.05$). Scale bar, 450 µm.

Figure 13A:
Figure 13B:
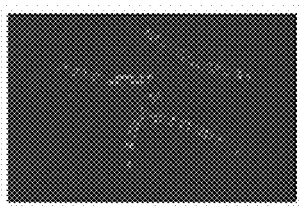
Figure 13C:
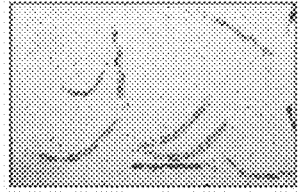
Figure 13D:
Figure 13E:
Figure 13F:
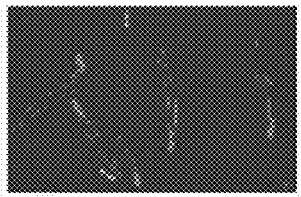
Figure 13G:
Figure 13H:
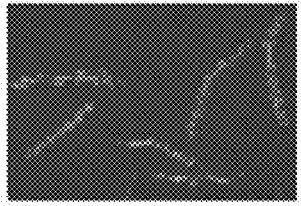
Figure 13I:
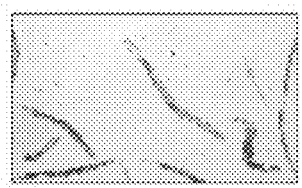
Figure 13J:
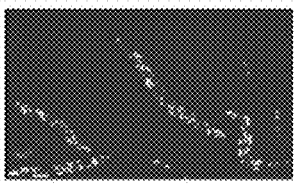
Figure 13K:
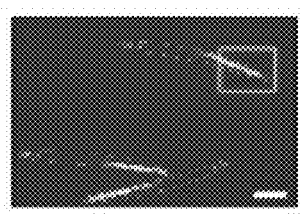
Figure 13L:
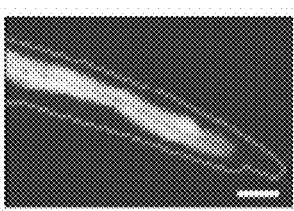
Figure 13M:
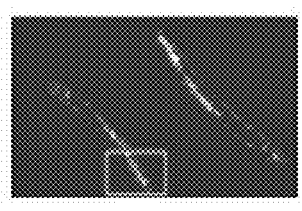
Figure 13N:
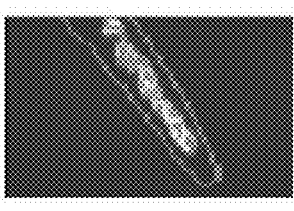
Figure 13O:
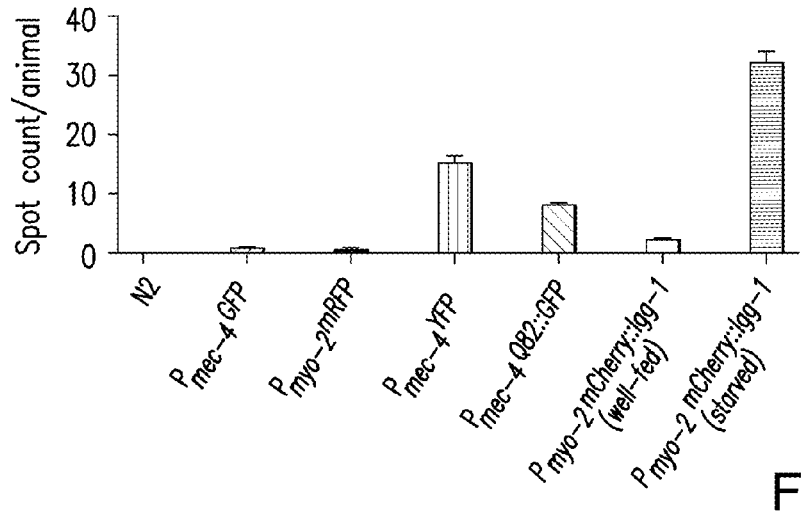
Figure 13P:
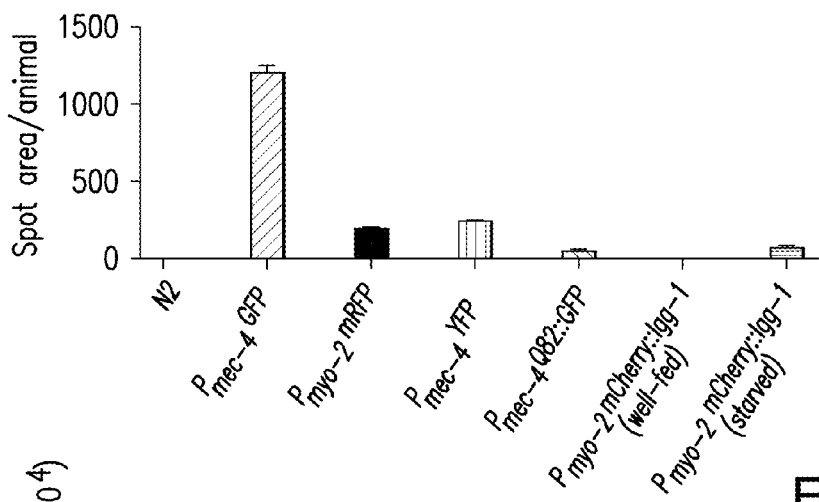
Figure 13Q:
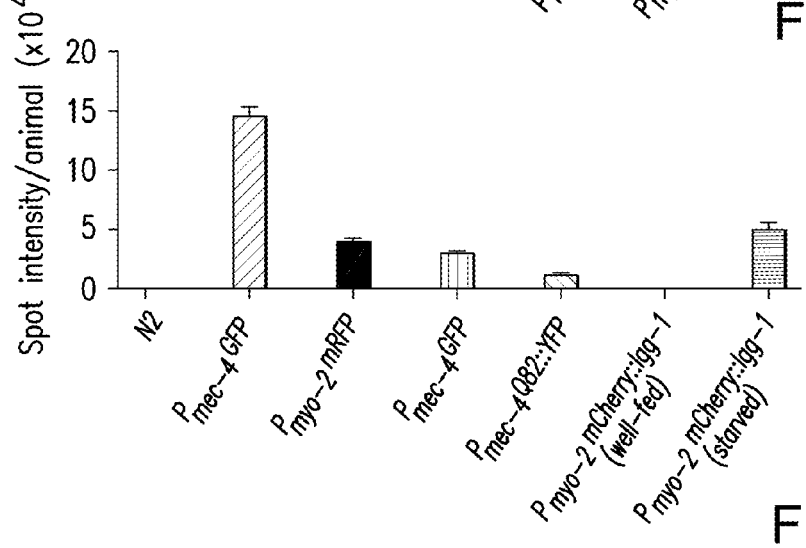

FIG. 13A-Q. Automated detection and quantification of cells, tissues, subcellular protein aggregates or autophagy in individual animals. (A-J) The SpotDetector BioApplication was used to identify and quantitate different types of transgene expression (left of panels) in adult animals. The brightfield channel (left panels) was used to discriminate between complete adult animals (outlined in blue) and debris or incomplete animals (outlined in orange), while a fluorescence channel (colored overlays in right panels) was used to detect different types of fluorescently tagged transgenes in correctly identified objects. (K-N) Fluorescence images of well-fed (K) and starved (M) animals expressing the autophagy marker, mCherry::LGG-1. In well-fed animals, mCherry::LGG-1 was diffusely cytoplasmic (K). In contrast, induction of autophagy by starvation leads to a punctate fluorescence pattern within intestinal cells, as LGG-1 is incorporated in to autophagosomes (M). (L, N) Higher magnification of the boxed areas in k and m, respectively. (O-Q) The different types of transgene expression were quantified by spot count (O), spot area (P) or spot intensity (Q) per animal. Spot count, spot area and spot intensity values for each of the transgenic lines were significantly (Student's t-test, $P<0.001$) different to that of N2 animals. Data derived from 10-50 wells containing ~20 animals/well. Scale bars, 225 µm (A-J, K, M), 50 µm (L, N).

Figure 14M:
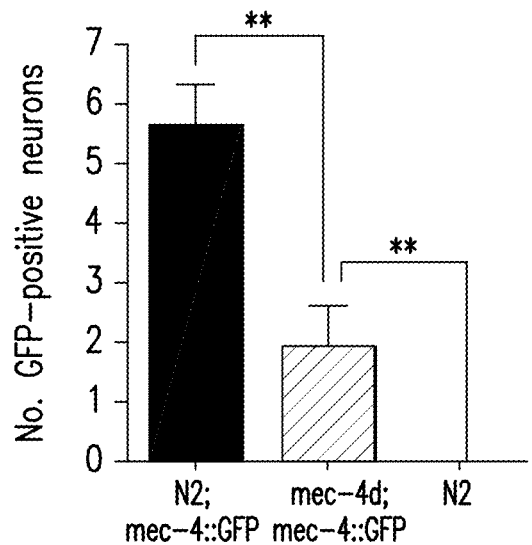
Figure 14N:
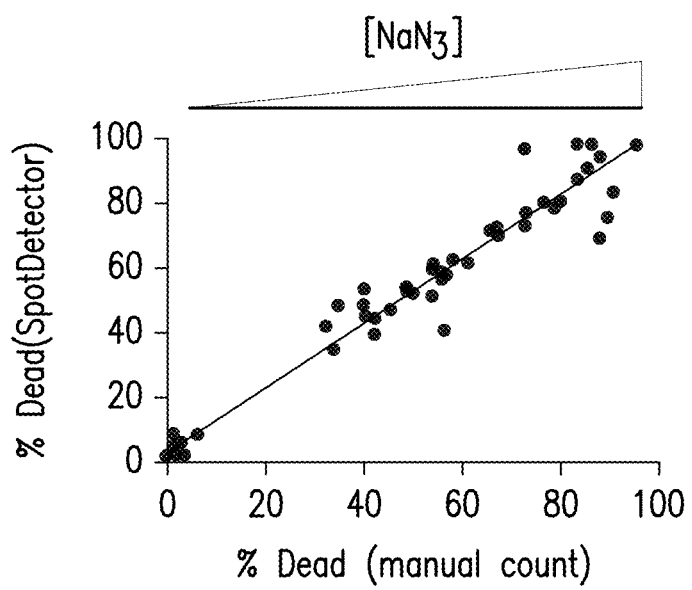

FIG. 14A-N. Identification of live cells or dead animals using C. elegans. The ArrayScan $V^{TI}$ and SpotDetector BioApplication was used to discriminate between wild-type and toxic gain-of-function mec-4(d) mutants based on the survival of the 6 mechanosensory neurons in C. elegans. Brightfield (left), fluorescence (center) and SpotDetector rendered (right) images are depicted for each line. (A-C, M) In N2 (wild-type) animals, $P_{mec-4}$GFP expression was evident within 5.7±0.7 touch-sensing neurons (arrowheads). (D-F, M) In the mec-4(d) mutant background, the number of $P_{mec-4}$GFP expressing neurons (arrowheads) was significantly reduced and averaged 2.0±0.7 neurons per animal. (g-i, m) No GFP-positive neurons were identified in non-transgenic, N2 worms. Data derived from minimum of 32 wells containing ~20 animals/well. Statistical significance determined using the Student's t-test, **$P<0.001$. The system was then used to discriminate live from dead animals. (J-L) Adult worms expressing the pharyngeal marker, $P_{myo-2}$mRFP, were incubated with various concentrations of NaAz, stained with SYTOX® Green and imaged using the ArrayScan $V^{TI}$ (J, K). The SpotDetector BioApplication was optimized to determine the percentage of dead animals by counting the number of SYTOX® Green-positive bodies (1) and dividing by the total number of $P_{myo-2}$mRFP-positive heads detected in the GFP and TRITC fluorescence channels, respectively. (N) Percentage of dead animals at different NaAz concentrations as determined by visual inspection versus that determined by SpotDetector. The slope and goodness-of-fit ($r^2$) of the linear regression were 1.0 and 0.95, respectively. The slope of the line was not significantly different to 1 indicating near 1:1 correlation (P>0.95). Scale bars, 100 µm (a-i), 225 µm, (j-l).

FIG. 15A-C. Identification of animals in a mixed population using a fluorescent head-marker. Thirty-six animals expressing the pharyngeal marker, $P_{myo-2}$mRFP were sorted into wells of 384-well plate. The wells contained different percentages (0-100%) of L4/young, and the SpotDetector BioApplication was optimized to select this group and reject younger animals (L1, L2 and L3 stages). (A) A brightfield-mRFP composite image of transgenic worms at different stages expressing $P_{myo-2}$mRFP. (B) A SpotDetector image showing the ability to differentiate adults (magenta overlay) from earlier staged larvae (white overlay) based on a combination of fluorescent spot area and intensity in the pharyngeal region. (C) Correlation between the percent of adults actually sorted per well vs. the percent of adults as determined by SpotDetector. The slope and goodness-of-fit ($r^2$) of the linear regression were 0.92 and 1.0, respectively. The slope of the line was not significantly different to 1 indicating near 1:1 correlation (P>0.05). Scale bar, 450 µm.

FIG. 16A-K. High-content analysis of transgenic animals expressing the wild-type (ATM) and mutant (ATZ) forms of human α1-antitrypsin (AT) fused to GFP. Thirty-five young adult animals were sorted into wells of a 385-well plate and imaged using the ArrayScan $V^{TI}$. (A, D) Brightfield images of sGFP::ATM and sGFP::ATZ expressing transgenic animals, respectively. (B, E) SpotDetector images of fluorescent red-heads for corresponding transgenic lines pictured in a and d, respectively. (C, F) SpotDetector images of sGFP::ATM and sGFP::ATZ expressing transgenic animals imaged in b and e, respectively. (G) The average number of transgenic animals in each well was determined by counting the number of mRFP-positive heads in channel 2 (TRITC). (H-J) The amount of sGFP::ATZ (green intracellular inclusions) accumulating within the intestinal cells of transgenic animals was compared to that of the sGFP::ATM line using the SpotDetector BioApplication to analyze the signal detected in channel 3 (GFP). Animals expressing the mutant protein (ATZ) were distinguished clearly from those animals expressing the wild-type protein (ATM) whether comparing total spot count (H), area (I) or intensity (J) per animal. Number of animals analyzed 2,240 (ATM) and 2,240 (ATZ). Error bars represent SD. (K) Assay quality was assessed using a scatter plot comparing total GFP-spot area/well (n=100 wells or 3,500 animals per strain) of sGFP::ATZ animals (○) to that of wild-type animals (●). Solid and dotted lines indicate the mean spot area ±3 standard deviations from the mean, respectively. The Z'-factor for this assay≈0.7.

FIG. 17A-K. LOPAC library screen. (A) Total spot area per animal (object), (B) z-scores and (C) B-scores from a representative screen assaying the effects of 1280 LOPAC compounds on sGFP::ATZ accumulation in transgenic animals. The x-axis represents the molecular identification (Mol ID) number of the compound. Known autofluorescent compounds were excluded from the plot. Selected compounds, based on rank-order (Supplementary Table 1) were analyzed for dose-dependent responses. Well images and dose-responses were obtained for compounds that decreased ((D) cantharidin, (E) fluphenazine and (F) pimozide) or increased ((G) tyrphostin AG 879) sGFP::ATZ accumulation. In each panel (D-G), well images on the left and right are DMSO (control)- and drug-treated animals, respectively. (H-K) Higher magnification fluorescent (top) and merged DIC (bottom) images of (H, J) DMSO- or (I, K) cantharidin-treated animals. Note loss of GFP::ATZ accumulation in the cantharidin treated animal. Scale bars, 450 µm (D-G) and 50 µm (H-K). Error bars represent SEM. Number of animals used was 140 for each compound concentration and 520 for the DMSO control. Significance was determined using an unpaired Student's t-test. Asterisks indicate values that differed significantly from animals treated with DMSO. *P<0.01 and **P<0.001.

FIG. 18A-E. Induction of autophagy by hit compounds. Images of transgenic animals expressing Pnhx-2mCherry:lgg-1 treated with various compounds are shown. Images were acquired using a Nikon instruments TiEclipse widefield light microscope fitted with a 20× Plan Apochromat objective. Images were then deconvolved using Volocity (Perkin Elmer, v 5.3.2). Deconvolved z planes were then merged to a single plane. Well-fed animals treated with DMSO (A) show a diffuse mCherry expression throughout the intestine. In contrast, animals treated with Cantharidin (B), Fluphenazine (C) and Pimozide (D) show a markedly punctate distribution pattern indicative of increased autophagic activity. Starved (E) animals are included as a positive control for autophagy. Scale bar, 50 µm.

Figure 19:
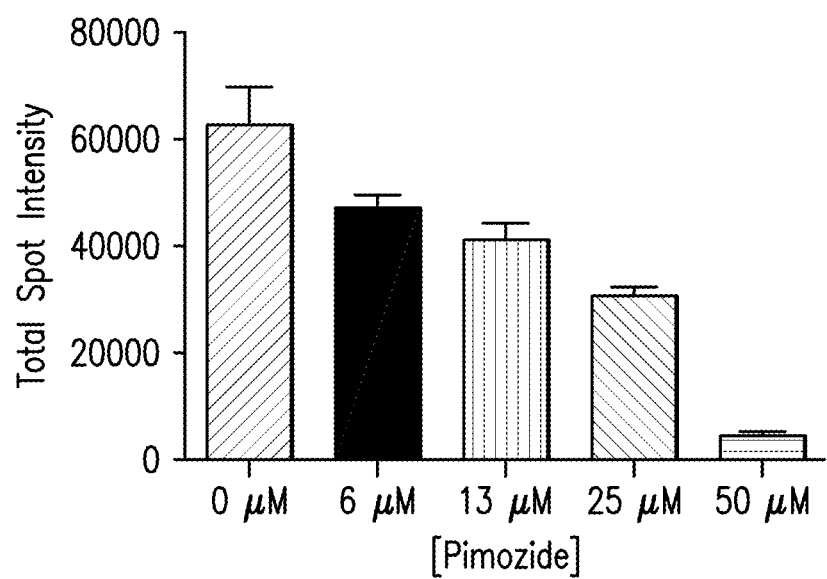

FIG. 19. Dose response effect of pimozide in HCS assay.

Figure 20:
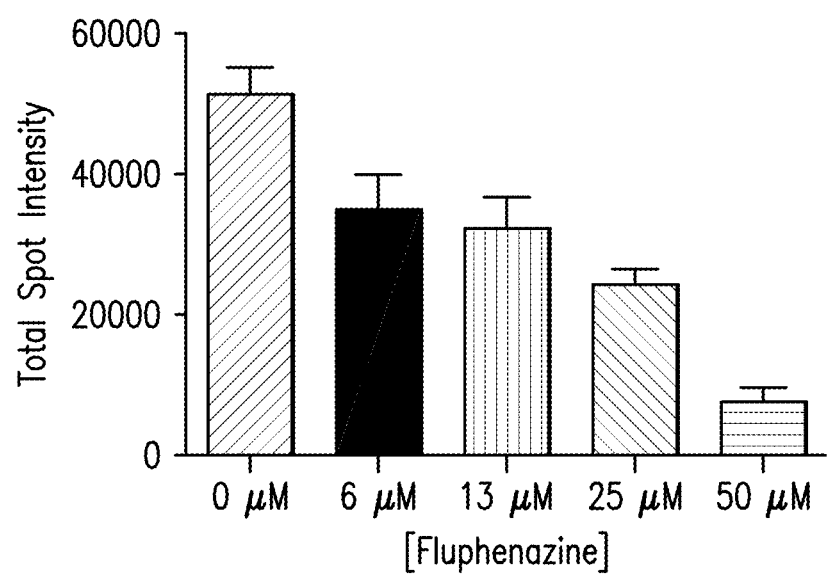

FIG. 20. Dose response effect of fluphenazine in HCS assay.

Figure 21:
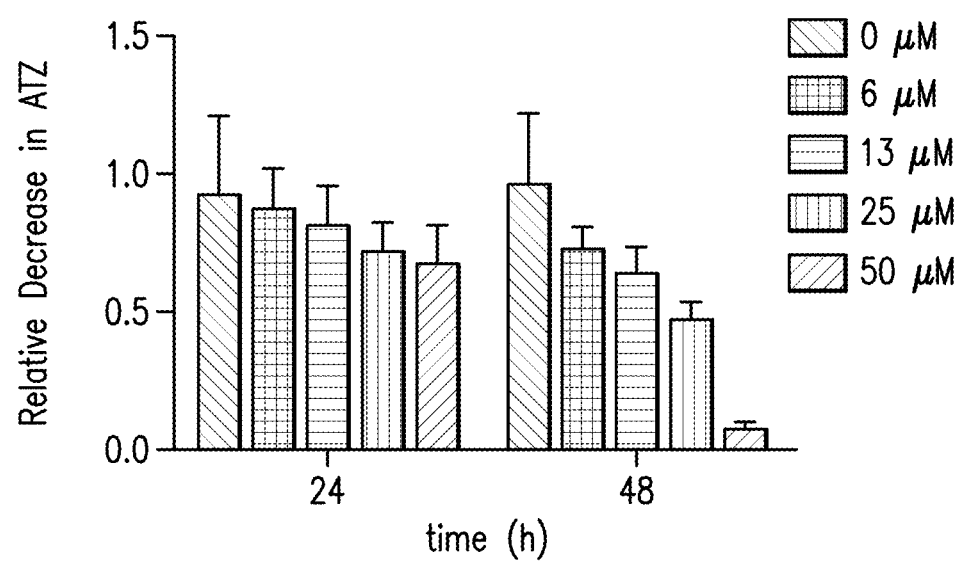

FIG. 21. Time/dose response effect of fluphenazine in HCS assay.

Figure 22:
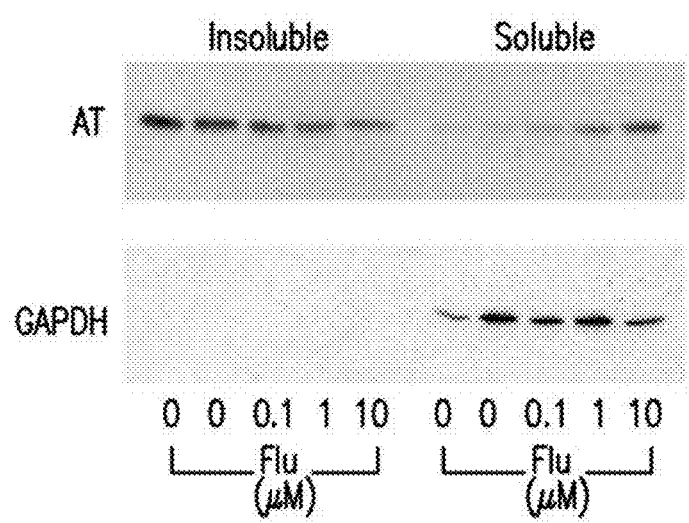

FIG. 22. HTO/Z cells were incubated for 24 hrs in the absence or presence of fluphenazine.

5. DETAILED DESCRIPTION OF THE INVENTION

For clarity of description and not by way of limitation, the detailed description of the invention is divided into the following subsections:
(i) constructs;
(2) model systems; and
(3) assays.

5.1 Constructs

The present invention provides for at least two types of constructs: first, an aggregation-prone protein construct which encodes a protein with a tendency to aggregate (which may also be referred to as a "aggregatable protein"), the expression of which results in the generation of aggregated protein in *C. elegans* and second, a marker construct which comprises a marker gene that encodes a marker protein, the expression of which assists in the characterization of animals in the assay, either by facilitating counting, developmental staging, organ localization, or some other characterization of the worm. Said constructs may comprise a promoter active in *C. elegans* which may optionally confer tissue specific, location-specific, and/or developmental stage-specific expression, operably linked to a nucleic acid encoding a protein with a tendency to aggregate or a marker protein (or, in non-limiting embodiments, both). Said constructs may optionally be comprised in vectors known in the art (e.g., a plasmid, phage or virus) or may be introduced directly into *C. elegans*. Said constructs may further comprise additional elements known in the art, for example, but not limited to, one or more selection marker, a translation termination site, etc.

In non-limiting embodiments of the invention, it may be desirable to express the protein with a tendency to aggregate and/or the marker protein in a particular cell type or location in the worm. As such, it may be desirable to use a promoter that is selectively active in said cell type or region. *C. elegans* has been extensively characterized, and lists of cell-type and location specific promoters are known in the art (see, for example, *C. elegans* II, second edition, Cold Spring Harbor Monograph Series, Vol 33, Cold Spring Harbor Press, Cold Spring Harbor, N.Y. (1997), and www-.wormbase.org. For example, and not by way of limitation:

neuron-specific promoters include, but are not limited to, ace-1, acr-5, aex-3, apl-1, alt-1, cat-1, cat-2, cch-1, cdh-3, ceh-2. ceh-2, ceh-6, ceh-10, ceh-14, ceh-17, ceh-23, ceh-28, ceh-36, che-1, che-3, cfi-1, cgk-1, cha-1, cnd-1, cod-5, daf-1, daf-4, daf-7, daf-19, dbl-1, des-2, deg-1, deg-3, del-1, eat-4, eat-16, ehs-1, egl-10, egl-17, egl-19, egl-2, egl-36, egl-5, egl-8, fax-1, flp-1, flp-1, flp-3, flp-5, flp-6, flp-8, flp-12, flp-13, flp-15, flp-3, fir-4, gcy-10, gcy-12, gcy-32, gcy-33, gcy-5, gcy-6, gcy-7, gcy-8, ggr-1, ggr-2, ggr-3, glr-1, glr-5, glr-7, glt-1, goa-1, gpa-1, gpa-1, gpa-2, gpa-3, gpa-4, gpa-5, gpa-6, gpa-7, gpa-8, gpa-9, gpa-10, gpa-11, gpa-13, gpa-14, gpa-15, gpa-16, gpb-2, gsa-1, ham-2, her-1, ida-1, ina-1, lim-4, lim-6, lim-6, lim-7, lin-11, lin-4, lin-45, mab-18, mec-3, mec-4, mec-7, mec-8, mec-9, mec-18, mgl-1, mgl-2, mig-1, mig-13, mus-1, ncs-1, nhr-22, nhr-38, nhr-79, nmr-1, ocr-1, ocr-2, odr-1, odr-2 odr-10, odr-3, odr-3, odr-7, opt-3, osm-10, osm-3, osm-9, pag-3, pef-1, pha-1, pin-2, rab-3, ric-19, sak-1, sdf-13, sek-1, sek-2, sgs-1, snb-1, snt-1, sra-1, sra-10, sra-11, sra-6, sra-7, sra-9, srb-6, srg-2, srg-, srd-1, sre-1, srg-13, sro-1, str-1, str-2, str-3, syn-2, tab-1, tax-2, tax-4, tig-2, tph-1, ttx-3, ttx-3, unc-3, unc-4, unc-5, unc-8, unc-11, unc-17, unc-18, unc-25, unc-29, unc-30, unc-37, unc-40, unc-3, unc-47, unc-55, unc-64, unc-86, unc-97, unc-103, unc-115, unc-116, unc-119, unc-129, and vab-7 promoters;

muscle-specific promoters include the hlh-1, mlc-2, myo-3, unc-54 and unc-89 promoters, pharynx specific promoters include the ceh-22, hlh-6 and myo-2 promoters; and gut-specific promoters include the nhx-2, vit-2, cpr-1, ges-1, mtl-1, mtl-2, pho-1, spl-1, vha-6 and elo-6 promoters.

Non-limiting examples of proteins with a tendency to aggregate include, but are not limited to, the human proteins: AT mutants ATZ, Siiyama and Mmalton; huntingtin; synuclein; amyloid beta; neuroserpin; ubiquitin; neurofilament protein; alpha B crystallin and tau, or a non-human equivalent thereof, or an aggregatable portion thereof. Because it is desirable to be able to detect aggregated proteins in *C. elegans*, in preferred, non-limiting embodiments of the invention the protein with a tendency to aggregate is comprised in a fusion protein with a second, detectable protein, for example, but not limited to, a fluorescent protein such as green fluorescent protein, enhanced green fluorescent protein, red fluorescent protein, yellow fluorescent protein, etc. As such, a portion of the native protein with a tendency to aggregate may optionally be omitted in the encoded fusion protein, and/or an additional protein or peptide may be comprised in the fusion protein, for example to link the protein with a tendency to aggregate with the detectable protein, provided that the tendency of the protein to aggregate is not substantially impaired (in specific non-limiting examples, at least about 90 percent or at least about 95 percent or at least about 98 percent of the native protein with a tendency to aggregate (examples of a "aggregatable portion") is present in the fusion protein). Likewise, it may be desirable to truncate or otherwise modify a native fluorescent protein to accommodate it into the fusion protein; such modifications are within the scope of the invention provided that the fluorescent protein remains fluorescent.

Non-limiting examples of marker proteins are the various fluorescent proteins that are fluorescent in vivo known in the art, including, but not limited to, green fluorescent protein, enhanced green fluorescent protein, red fluorescent protein, yellow fluorescent protein, etc.

In particular, non-limiting embodiments of the invention, expression of the marker construct results in a single detectable region (or image) per worm. "A single detectable region" means that using a detection means appropriate for the assay, expression of the marker results in a pattern of detectable signal which can be perceived as a single region (for example, the pharyngeal region, the head region, the worm surface, or the entire worm) so that perception of that region allows for the discrimination of one worm from another and therefore facilitates accurate counting of worms. In specific non-limiting embodiments according to this paragraph, the marker gene is operably linked to a pharynx-specific (e.g. myo-2) *C. elegans* promoter.

In particular, non-limiting embodiments of the invention, expression of the marker construct results in a defined number of detectable regions (or images) per worm. "A defined number of detectable regions" means that using a detection means appropriate for the assay, expression of the marker results in a pattern of detectable signal which can be consistently perceived as a defined number of regions (for example, 2 or 3 or 4, etc. regions), so that perception of that region allows for the discrimination of one worm from another and therefore facilitates accurate counting of worms (where the number of images counted reflects the number of worms presented multiplied by a factor which is the defined number of detectable regions per worm). In specific non-limiting embodiments according to this paragraph, one or more marker gene is operably linked to one or more promoter so that the marker is expressed two detectable regions per animal, so that the number of worms present may be determined by counting the number of detectable regions and dividing by two. An analogous approach could be used to produce worms having three detectable regions which could be determined by counting the regions and dividing by three, etc.

In related non-limiting embodiments, the invention provides for other methods of defining worms and worm boundaries. For example, the present invention provides for a transgenic *C. elegans* worm expressing myo-3::mCherry which is specifically expressed in the muscles and effectively creates an outline of the worm. Such worms may be further engineered to express ATZ::GFP in any tissue and quantify ATZ aggregation/polymerization within the myo-3::mCherry boundary.

The present invention further provides for worms carrying at least three transgenes. In a specific, non-limiting embodiment, a transgenic *C. elegans* may be engineered to express the fusion proteins ATZ::YFP, myo-2::CFP and LGG-1::mCherry. These worms may be used to identify/study the effect of a particular compound on ATZ disposition and autophagy, simultaneously. Similarly, we could engineer worms to express hsp-4::mCherry as the third marker to study the "unfolded protein response" (UPR). As an alternative non-limiting example, a *C. elegans* may be engineered to express myo-2::mCherry (red-head marker), nhx-2::sGFP::ATZ (intestine) and lgg-1::CFP (blue marker for autophagy). In such worms, the red head (mCherry) region may be used to determine the number of worms in the well, the green (GFP) regions may be measured to determine the extent of ATZ aggregation/polymerization and the blue (CFP) region may be used to measure the level of autophagy.

In particular, non-limiting embodiments of the invention, in order to facilitate expression in C. elegans, which is believed to be more efficient in the presence of introns, where a nucleic acid encoding either a protein with a tendency to aggregate (or aggregatable portion thereof) or a marker protein lacks introns, one or more (e.g., 1, 2, 3 or 4, etc.) "synthetic" intron may be introduced (either by engineering blunt-end restriction sites into the protein-encoding DNA (e.g., cDNA) by site-directed mutagenesis or by overlap-extension PCR (see below)). Synthetic introns are between 48-51 bp in length and include consensus splice acceptor (AGGUAAGU) and splice donor (CAGG) sequences at the 5' and 3' ends, respectively.

Accordingly, in one set of particular, non-limiting embodiments, the present invention provides for an aggregated protein construct comprising a nucleic acid encoding a protein with a tendency to aggregate (for example, but not limited to, a human protein such as ATZ, huntingtin, synuclein, amyloid beta, neuroserpin, ubiquitin, neurofilament protein, alpha B crystallin and tau, or a non-human equivalent thereof, or an aggregatable portion thereof) optionally comprised in a fusion protein with a detectable protein such as a fluorescent protein, operably linked to a C. elegans promoter, where said promoter may, for example, be a neuron-specific promoter, a gut (e.g. intestinal) specific promoter, a muscle specific promoter, a pharynx-specific promoter, or a tail specific promoter, and where said nucleic acid encoding a protein with a tendency to aggregate optionally comprises one or more synthetic intron.

In a specific, non-limiting embodiment of an aggregated protein construct according to the invention which is expressed in intestinal cells of C. elegans, Pnhx-2sGFP::ATM may be generated by inserting a 4 kb nhx-2 promoter fragment into HindIII/XbaI restriction sites of the expression vector, pPD95.85. Then a KasI restriction site may be introduced by site-directed mutagenesis into the GFP translational stop codon. A 1.4 kb fragment containing the ATM cDNA and 3 synthetic introns may be cloned into the KasI site. Pnhx-2sGFP::ATZ may be generated by site-directed mutagenesis of Pnhx-2sGFP::ATM, thereby generating the E342K (Z) mutation.

Figure 1B:
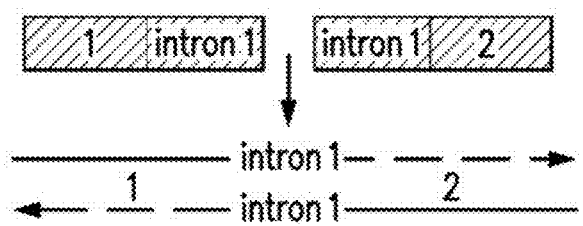

In a related specific, non-limiting embodiment, to improve ATZ expression, synthetic introns resembling those found in C. elegans may be introduced into the ATZ cDNA using overlap-extension PCR (FIG. 1A-B). Large oligonucleotides consisting of ~50 nucleotides of synthetic intron (carefully designed to contain appropriate 5' and 3' donor/acceptor sequences) and ~22 nt sequence complementary to the ATZ coding region may be synthesized and used as primers to amplify small regions of the ATZ cDNA (see FIG. 1A). The amplified fragments may be joined pairwise using overlap-extension PCR to generate larger fragments containing intronic regions (see FIGS. 1B and 1C). Once the 5 pieces are joined together, the complete ATZ fragment containing all of the synthetic introns may be amplified using primers flanked with Kas I recognition sites (see FIG. 1D) and cloned into the expression vector pPD95.85 to generate Pnhx-2::sGFP::ATZ.

In additional non-limiting specific embodiments of aggregated protein constructs, constructs encoding neuroserpin which are expressed in intestinal or neuronal cells of C. elegans are shown in TABLE 3 below.

In a specific, non-limiting embodiment of a marker construct according to the invention that is expressed selectively in the C. elegans pharynx, a transcriptional Pmyo-2mRFP fusion (where RFP is "Red Fluorescent Protein") construct may be constructed by subcloning the myo-2 promoter and the mRFP cDNA into the SphI/XbaI and NheI/EcoRV sites of the canonical expression vector, pPD49.26, respectively.

5.2 Model Systems

A "model system" according to the invention comprises a C. elegans adapted to serve as a model of a disorder of protein aggregation. For example, a model system may be a Caenorhabditis elegans carrying a transgene comprising an aggregated protein construct comprising a nucleic acid encoding a protein with a tendency to aggregate (for example, but not limited to, a human protein such as ATZ, huntingtin, synuclein, amyloid beta, neuroserpin, ubiquitin, neurofilament protein, alpha B crystallin and tau, or a non-human equivalent thereof, or an aggregatable portion thereof), optionally comprised in a fusion protein with a detectable protein such as a fluorescent protein, operably linked to a C. elegans promoter, where said promoter may, for example, be a neuron-specific promoter, a gut (e.g. intestinal) specific promoter, a muscle specific promoter, a pharynx-specific promoter, or a tail specific promoter, and where said nucleic acid encoding a protein with a tendency to aggregate optionally comprises one or more synthetic intron, as described in the section above. In particular, non limiting embodiments, said C. elegans may further comprise an additional transgene comprising a marker construct comprising a marker gene operably linked to a C. elegans promoter and encoding a marker protein, as described in the section above. Preferably, where the protein with a tendency to aggregate is comprised in a fusion protein with a first fluorescent protein and where the marker construct encodes a second fluorescent protein, the first and second fluorescent protein are not the same (for example, so that their fluorescent emissions are distinguishable (for example, they may have a different wavelength)). In a specific non-limiting embodiment of such a model system, expression of the marker construct results in a single or otherwise consistently countable detectable region (or image) per worm.

In particular, non-limiting embodiments, the present invention provides for a model system for α1-antitrypsin deficiency comprising a C. elegans carrying a transgene comprising an aggregated protein construct comprising a nucleic acid encoding ATZ optionally comprised in a fusion protein with a detectable protein such as a fluorescent protein, operably linked to a C. elegans promoter, where said promoter is a gut specific promoter, and where said nucleic acid encoding ATZ optionally comprises one or more synthetic intron. In particular, non limiting embodiments, said C. elegans may further comprise an additional transgene comprising a marker construct comprising a marker gene operably linked to a C. elegans promoter and encoding a marker protein.

In another particular, non-limiting embodiment, the present invention provides for a model system for a disorder associated with protein aggregation in neurons comprising a Caenorhabditis elegans carrying a transgene comprising an aggregated protein construct comprising a nucleic acid encoding a protein with a tendency to aggregate (for example, but not limited to, a human protein such as huntingtin, synuclein, amyloid beta, neuroserpin, ubiquitin, neurofilament protein, alpha B crystallin and tau, or a non-human equivalent thereof, or an aggregatable portion thereof), optionally comprised in a fusion protein with a detectable protein such as a fluorescent protein, operably linked to a C. elegans promoter, where said promoter may, for example, be a neuron-specific promoter, a gut (e.g. intestinal) specific promoter, a muscle specific promoter, a pharynx-specific promoter, or a tail specific promoter, and where said nucleic acid encoding a protein with a tendency to aggregate optionally comprises one or more synthetic intron, as described in the section above. In particular, non limiting embodiments, said *C. elegans* may further comprise an additional transgene comprising a marker construct comprising a marker gene operably linked to a *C. elegans* promoter and encoding a marker protein. As specific non-limiting examples of such embodiments, in a model system for AD the protein with a tendency to aggregate may be human amyloid beta, or an aggregatable portion thereof; in a model system for Parkinson's disease the protein with a tendency to aggregate may be human synuclein, or an aggregatable portion thereof; in a model system for Huntington's disease the protein with a tendency to aggregate may be human huntingtin, or an aggregatable portion thereof; in a model system for chronic traumatic brain injury the protein with a tendency to aggregate may be human tau protein, or an aggregatable portion thereof; and so forth.

Transgenic *C. elegans* may be prepared by methods known in the art, including, but not limited to, microinjection or microparticle bombardment. In a specific, non-limiting embodiment of the invention, an aggregated protein construct and/or a marker construct may be introduced by injection into the gonad of a young adult hermaphrodite worm, for example, at a concentration of about 80 ng/µl.

5.3 Assays

In particular, non-limiting embodiments, the present invention provides for a method of determining whether a test compound has activity in treating a disorder of protein aggregation (and/or activity in reducing the amount of protein polymer), comprising:

(i) administering said test compound to a plurality of transgenic *C. elegans* carrying (a) a first transgene comprising a nucleic acid encoding a human protein with a tendency to aggregate, or an aggregatable portion thereof, operably linked to a *C. elegans* promoter, where the expression of the human protein results in a detectable accumulation of human protein in the *C. elegans* (which may be detectable, for example, because the human protein with a tendency to aggregate, or an aggregatable portion thereof, may be comprised in a fusion protein with a first fluorescent protein) and (b) a second transgene comprising a marker construct comprising a marker gene encoding a marker protein (e.g., a second fluorescent protein) operably linked to a *C. elegans* promoter;

(ii) determining the change in the amount of human protein (or aggregatable portion thereof) associated with the administration of test compound in the plurality of *C. elegans* (for example, by determining a change in the level of fluorescence associated with a first fluorescent protein fused to the aggregatable protein, as compared to a standard value, or compared to the amount of protein prior to administration of the compound in the same population of worms, or compared to the amount of protein in a parallel control population of worms that have not been exposed to the compound);

(iii) using the marker protein, determining the number of *C. elegans* in said plurality (for example, where the marker protein generates a single or a definite number of images per worm, counting those images as a direct method of determining the number of worms, and where the marker protein may be a second fluorescent protein having a fluorescence distinguishable from that of the first fluorescent protein fused to the aggregatable protein);

(iv) using the results of (ii) and (iii), determining the change in the amount of human protein per worm resulting from the administration of test compound;

Wherein, if administration of the test compound results in a significant decrease in the amount of human protein per worm, then the test compound is indicated to be therapeutically effective in a disorder of protein aggregation.

The methods are preferably practiced in a high-throughput format where at least 96 or at least 384 (or more) test compounds may be tested in parallel.

In a specific, non-limiting embodiment of the invention, a 96 well-based assay may be performed as follows. Fifty-five young adult stage worms may be dispensed into 96-well plates using the COPAS BioSort (worm sorter). Worms may then be immobilized by the addition of 0.1 M sodium azide to facilitate image capture. The plates may be placed into a computerized high throughput plate reader, ArrayScanVTi (Thermofisher Cellomics Products). ArrayScanVTi may be set up to rapidly scan wells and capture multiple images using brightfield and fluorescence parameters. Algorithms, as discussed below, may be used to identify and quantify defined spots (fluorescent granules) and objects (individual animals). A typical screen shot of the ArrayScanVTi interface is shown in FIG. 5. In this case, brightfield and GFP fluorescence images were taken from 4 different fields within each well using a 5× Carl Zeiss objective. A single field showing a brightfield and GFP fluorescence overlay illustrates GFP aggregates throughout the length of the intestine (FIG. 5, well D1). To quantify these GFP aggregates, algorithms were developed to first identify the objects of interest (adult worms) and quantify the number and intensity of the spots (aggregates). FIG. 6 shows exactly the elements from FIG. 5 that were selected for data analysis. ArrayScanVTi correctly identified all adult worms in the field of view (blue outline) and excluded all eggs and other debris that would alter the analysis. Moreover, the algorithm identified all the ATZ aggregates (FIG. 6, red spots) within the set boundary (FIG. 6, red outline).

To quantify the differences between the types of animals, the total number of spots and the total and average spot area for multiple detection fields may be determined by the algorithm (for example, see FIG. 8). In a preferred, specific, non-limiting embodiment of the invention, a transgenic *C. elegans* that expresses an ATZ/GFP fusion protein and carries a second transgene encoding a red fluorescent protein (mCherry) as marker protein which is expressed only in the head (pharynx) region of the worm. The expression of a second fluorescent marker that has a distinct expression pattern than GFP::ATZ (intestine) has several major advantages. First, the bright expression of the mCherry protein significantly improves focus time and efficiency. Second, with optimized algorithms, red heads can be easily counted to obtain accurate worm number per well. Thirdly, since the pharynx is in the same focal plane as the intestine, GFP::ATZ aggregates can be more efficiently and accurately measured. By simply dividing the total GFP fluorescence in the well by the total number red heads, the average GFP fluorescence per worm can be determined, a capability that was problematic to achieve using the brightfield object identification algorithms.

In another specific non-limiting embodiment of the invention, a 384-well assay may be performed as follows. A 384-well-based assay has several advantages over the 96-well format. First, one can screen more compounds using the same number of worms needed for a 96-well plate. Second, images can be captured using the 2.5× objective. This reduces the number of fields needed to capture the well from 16 to 1. For this assay, the Arrayscan VTi may be fitted with a 0.63× coupler. The 0.63× coupler allows the capture of 100% of the well (as opposed to ~90% using the 1× coupler) allowing one to account for all the worms on in the well, leading to a considerably smaller variance between replicate wells. Two μl of stock (10 mM) compounds may be diluted with 98 μl of S-medium to a final concentration of 200 μM drug in 2% DMSO and S-medium. Fifteen μl of the diluted compounds may then be transferred to 384-well plates using a robotic liquid handler (EP3). Prior to the experiment, fifteen μl of 4×OP50/antibiotic solution may be added to each well. Using the COPAS Biosort, 35 L4-young adult stage worms may be deposited into each well and allowed to incubate for 24 or 48 h at 22° C. At the end of the incubation period, worms may be immobilized by the addition of sodium azide or levamisole to a final concentration of 12.5 mM and 4 mM, respectively. The worms may then be imaged using the high speed, automated imaging device, ArrayScan VTi. Image capture and data analysis may be performed using the Spot Detector BioApplication with algorithms optimized for worms. B-score statistical analyses may be performed to identify compounds that had a significant (>2 SDs away from the mean) effect on ATZ aggregation. A summary of a typical LOPAC screen is shown in FIG. 11.

In another specific non-limiting embodiment of the invention, compound tracking and data analysis for the primary HCS assay may be performed using ActivityBase™ (IDBS, Guildford, UK), CytoMiner (UPDDI) software and visualized using Spotfire™ DecisionSite® (TIBCO Software Inc., Somerville, Mass., USA) software, as described in 60-63. Custom calculators were written to process the HCS data and perform the z-score and B-score statistical analysis (64,65). As a measure of assay quality and robustness, the Z'-factor 30 may be used. The Z'-factor may be calculated from the mean and the standard deviation of the negative and positive control populations as follows:

$$Z'=1-((3\times(\sigma_p+\sigma_n))/(\mu_p-\mu_n))$$

where σ is the standard deviation, μ is the mean and p and n are positive and negative controls, respectively. Z'-factors between 0.5 and 1.0 indicate the separation band (signal window) between the positive and negative controls is wide and the assay is of excellent quality and suitable for HTS/HCS. Z'-factors between 0 and 0.5 indicate a good quality screen, whereas a score <0 indicates the assay is of poor quality and unsuitable for HTS/HCS. The z-score plate-based statistical scoring method may be used as described previously to identify compounds that behaved as statistical outliers compared to the other substances (n=320, no controls) tested on an assay plate for selected HCS multiparameter measurements output by the image analysis module (62). The z-score=$(X_i-\overline{X})/\sigma$, where $X_i$ is the raw measurement on the ith compound, and $\overline{X}$ and σ are the mean and standard deviation of all the sample measurements on a plate. The B-score may be calculated from all of the sample measurements on an assay plate and used an iterative mathematical model to eliminate systematic row and column artifacts on a plate. The mathematical model of the B-score may be described as:

$$Y_{ijp}=\mu_{ijp}+YR_{ip}+YC_{jp}+\epsilon_{ijp}$$

where $Y_{ijp}$ is the compound measurement at $i_{th}$ row and $j_{th}$ column of the $p_{th}$ plate, $\mu_{ijp}$ is the 'true' activity value, $\epsilon_{ijp}$ is the random error of the assay on the $p_{th}$ plate, and $YR_{ip}$ and $YC_{jp}$ represent the row and column artifacts on the pth plate, respectively. A two-way median polish statistic method may be applied to estimate the B-score of a HCS assay. The random error estimate, $\hat{\epsilon}_{ijp}$, of the measurement at $i_{th}$ row and $j_{th}$ column of the $p_{th}$ plate may be calculated by fitting a two-way median polish as:

$$\hat{\epsilon}_{ijp}=Y_{ijp}-\hat{Y}_{ijp}=Y_{ijp}-(\hat{\mu}+\hat{R}^{ip}+\hat{C}_{jp})$$

where $\hat{Y}_{ijp}$ is the fitted compound value, $\hat{\mu}$ is the estimated average of the plate, and $\hat{R}_{ip}$ and $\hat{C}_{jp}$ are the estimated systematic artifacts for the $i_{th}$ row on $p_{th}$ plate and $j_{th}$ column on $p_{th}$ plate, respectively. Next the median absolute deviation (MAD) of the random error estimate on $p_{th}$ plate may be computed as:

$$MAD_p=\text{Median}\{|\hat{\epsilon}_{ijp}-\text{Median}(\hat{\epsilon}_{ijp})|\}$$

At the last step, the B score may be calculated as:

$$B-\text{score}=\frac{\hat{\epsilon}_{ijp}}{MAD_p}$$

The compounds may be ranked according to ascending B-score values. Rank-scores may be calculated by taking the average of compound rankings from two independent drug screens. Compounds with rank-scores <110 may be considered to significantly decrease the accumulation of sGFP::ATZ inclusions. Conversely, compounds with rank-scores >1225 may be considered to significantly increase the accumulation of sGFP::ATZ inclusions. Selected compounds may be chosen for further analysis, for example in a human cell culture and/or animal model assay.

The foregoing specific examples may readily be modified to study other proteins with a tendency to aggregate according to the invention.

6. EXAMPLE: HIGH THROUGHPUT GENETIC AND DRUG SCREENS FOR α1-ANTITRYPSIN DEFICIENCY USING C. ELEGANS

Several characteristics of AT deficiency make it an attractive target for chemoprophylaxis strategies involving high-throughput screening of small molecule libraries. First, the disease predominantly involves an ER translocation defect, wherein mutant ATZ protein retains some of its anti-elastase activity (i.e., ATZ can inhibit neutrophil elastase albeit not as efficiently as AT). Thus, small molecules that increase ATZ secretion could theoretically prevent tissue damage in both lung and liver. Second, the severity of tissue injury caused by ATZ is thought to be influenced by genetic and environmental modifiers that regulate endogenous quality control mechanisms for disposal of misfolded proteins. Compounds that enhance these degradative processes could therefore be used in patients to prevent liver damage in combination with strategies specifically designed to prevent lung damage.

A tractable genetic model of this disease would greatly enhance the ability to elucidate the mechanism of tissue damage and the endogenous mechanisms that protect against protein misfolding. As shown by the results of experiments described below, the conformational disease of AT deficiency can be modeled in C. elegans. Animals expressing wild-type AT (ATM) secrete the protein. In contrast, animals expressing ATZ develop intracellular inclusions and show a slow growth and larval arrest/lethality phenotype. Further, an assay using this model has been adapted to allow for automated high-throughput screening.

Many different abbreviations have been used in the literature to designate α1-antitrypsin (AT) and its mutant alleles. To avoid confusion, the nomenclature for mutant and wild-type AT alleles used herein is described in TABLE 1.

TABLE 1

AT allele/gene product abbreviations

| abbreviation | description of allele and gene product |
|---|---|
| AT | generic for antitrypsin, does not designate a specific allele |
| ATM | wild-type M allele, also referred to as AT in many publications |
| ATZ | classical Z mutant with E342K mutation that is polymerogenic and accumulates in the ER |
| ATM-Saar | 32 amino acid C-terminal truncation mutant that is non-polymerogenic and accumulates in the ER; referred to as AT Saar in our previous publications. |
| ATZ-Saar | 32 amino acid C-terminal truncation mutant that also has the point mutation of ATZ, but is non-polymerogenic and accumulates in the ER; referred to as AT saar Z in our previous publications. |
| ATS | E264V - second most common mutation |
| ATI | R39C - decreased inhibitory activity, mild deficiency |
| $ATM_{malton}$ | TTC deletion/DF52 - shorter polymers in plasma @2-3 units; better secreted than Z |
| $ATM_{siiyama}$ | S53F - polymers in plasma@15-20 units; second site mutation (F51L) enhances secretion $M_{siiyama} >> Z$ |
| $AT_{Hong\ Kong}$ | TC deletion; L318fsX334, ERAD substrate; loss 61 aa; not secreted |

Construction of ATZ Expression Plasmids.

To readily visualize ATZ aggregates in live animals without the need for complex immunological staining methods, ATZ was fused to the green fluorescent protein (GFP). Although, GFP-fusions have been used extensively in cell culture and other systems, their usefulness in studying ATZ aggregation has not been tested in C. elegans. Since ATZ aggregation is thought to occur via insertion of the reactive site loop (RSL) of one molecule into the β-sheet of another, it was unclear whether GFP would interfere with this process. To assess this, N- and C-terminal GFP-ATZ fusion constructs were engineered. The nhx-2 promoter (Pnhx-2), which drives expression specifically in the intestinal cells through all stages of postembryonic development, was chosen to direct expression of the fusion construct. The C. elegans intestine is the center of metabolic activity and the organ that most closely resembles the human liver (where ATM is normally synthesized). In addition, the intestine would be the predominant site of absorption for compounds added to the media. To direct transgene expression to the ER-Golgi secretory pathway, the synthetic signal peptide from the C. elegans expression vector, pPD95.85, was used (Fire Lab C. elegans Vector Kit, 1995).

Figure 1C:
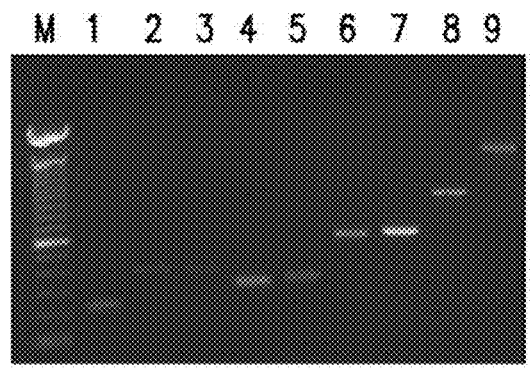
Figure 1D:
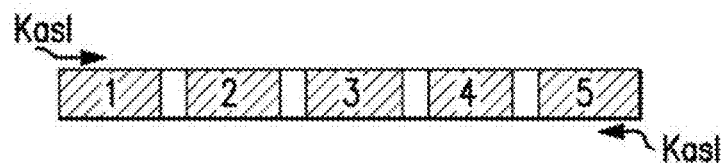

Initial expression studies using human AT cDNA were hampered by low expression of the transgene. In C. elegans, transgene expression is quantitatively enhanced by the presence of intronic sequences. As such, genomic DNA is preferred over cDNA. The large gene size and variations in RNA splicing requirements between human and C. elegans make it impractical to use genomic ATZ DNA for expression studies in C. elegans. To improve ATZ expression, synthetic introns resembling those found in C. elegans were introduced into the ATZ cDNA. Typically, introns are introduced by engineering unique blunt end restriction enzyme sites in the cDNA by site-directed mutagenesis. This approach is labor intensive, inefficient and dictated by the presence of favorable sequences. As an alternate approach, a strategy was devised for intron insertion using overlap-extension PCR (FIG. 1A-B). Large oligonucleotides consisting of ~50 nt of synthetic intron (carefully designed to contain appropriate 5' and 3' donor/acceptor sequences) and ~22 nt sequence complementary to the ATZ coding region were synthesized and used as primers to amplify small regions of the ATZ cDNA (FIG. 1A). The amplified fragments were joined pairwise using overlap-extension PCR to generate larger fragments containing intronic regions (FIGS. 1B and 1C). Once the 5 pieces were joined together, the complete ATZ fragment containing all of the synthetic introns was amplified using primers flanked with Kas I recognition sites (FIG. 1D) and cloned into the expression vector pPD95.85 to generate Pnhx-2::sGFP::ATZ. A control construct designed to express ATM, Pnhx-2::sGFP::ATM, was also generated. Prior to the insertion of the ATZ fragment, several modifications were made to pPD95.85 vector to facilitate cloning and to ensure proper transgene fusion. First, a unique Kas I restriction enzyme site was introduced 3' to the GFP coding sequence to accommodate insertion of ATZ. Second, the stop codon of GFP was removed to ensure read-through to the downstream ATZ gene. All of the constructs were sequenced to confirm the absence of mutations and in-frame insertion of coding regions. In addition to the ATZ and wild-type alleles (ATM), a series of constructs were generated containing several other well-described AT mutations to determine how their phenotypes compare to that of ATZ. A list of all the AT constructs is shown in TABLE 2. Studies comparing the position (N- or C-terminus) of the GFP fusion indicated that N-terminal GFP::AT fusions were more efficiently expressed. As such, all subsequent AT expression constructs were generated with N-terminally fused GFP. In addition to AT, another serpin aggregation disorder called Familial encephalopathy with neuroserpin inclusion bodies (FENIB) has also been modeled in C. elegans. Naturally occurring mutations cause neuroserpin to aggregate in a manner similar to that of ATZ. Thus, a C. elegans model of FENIB may be used for the study of neuroserpin aggregation and the identification of therapeutic drugs. Constructs used to generate neuroserpin transgenic worms are shown in TABLE 3.

TABLE 2

AT constructs used to generate transgenic worms

| Name | Promoter | Sig | GFP | Description |
|---|---|---|---|---|
| Pnhx-2::sATM | intestine | No | none | Secreted ATM (no GFP) |
| Pnhx-2::sATZ | intestine | No | none | Secreted ATZ (no GFP) |
| Pnhx-2::GFP | intestine | No | — | Intracellular expression of GFP |
| Pnhx-2::GFP::ATM | intestine | No | N-terminal | Intracellular expression of GFP::ATM |

TABLE 2-continued

AT constructs used to generate transgenic worms

| Name | Promoter | Sig | GFP | Description |
|---|---|---|---|---|
| Pnhx-2::GFP::ATZ | intestine | No | N-terminal | Intracellular expression of GFP::ATZ |
| Pnhx-2::sGFP | intestine | Yes | | Secreted GFP (control) |
| Pnhx-2::sGFP::ATM | intestine | Yes | N-terminal | Secreted GFP::ATM |
| Pnhx-2::sGFP::ATZ | intestine | Yes | N-terminal | Secreted GFP::ATZ |
| Pnhx-2::sATM::GFP | intestine | Yes | C-terminal | Secreted ATM::GFP |
| Pnhx-2::sATZ::GFP | intestine | Yes | C-terminal | Secreted ATZ::GFP |
| Pnhx-2::sGFP::ATM.saar | intestine | Yes | N-terminal | Secreted GFP::ATM.saar |
| Pnhx-2::sGFP::ATZ.saar | intestine | Yes | N-terminal | Secreted GFP::ATZ.saar |
| Pnhx-2::sGFP::ATS | intestine | Yes | N-terminal | Secreted GFP::ATS |
| Pnhx-2::sGFP::ATI | intestine | Yes | N-terminal | Secreted GFP::ATI |
| Pnhx-2::sGFP::ATM$_{malton}$ | intestine | Yes | N-terminal | Secreted GFP::ATM$_{malton}$ |
| Pnhx-2::sGFP::ATM$_{siiyama}$ | intestine | Yes | N-terminal | Secreted GFP::ATM$_{siiyama}$ |
| Pnhx-2::sGFP::AT$_{Hong\ Kong}$ | intestine | Yes | N-terminal | Secreted GFP::AT$_{Hong\ Kong}$ |
| Psrp-2::GFP | hypoderm | No | — | Intracellular expression of GFP (control) |
| Psrp-2::sGFP | hypoderm | Yes | N-terminal | Secreted GFP (control) |
| Psrp-2::sGFP::ATM | hypoderm | Yes | N-terminal | Secreted GFP::ATM |
| Psrp-2::sGFP::ATZ | hypoderm | Yes | N-terminal | Secreted GFP::ATZ |

TABLE 3

Neuroserpin (NS) expression constructs

| Name | Promoter | Sig | Description |
|---|---|---|---|
| Pnhx-2::sGFP::NS | intestine | Yes | Wild-type neuroserpin |
| Pnhx-2::sGFP::NS(S49P) | intestine | Yes | Polymerigenic mutant |
| Pnhx-2::sGFP::NS(G392E) | intestine | Yes | Polymerigenic mutant |
| Punc-119::sGFP::NS | pan-neuronal | Yes | Wild-type neuroserpin |
| Punc-119::sGFP::NS(S49P) | pan-neuronal | Yes | Polymerigenic mutant |
| Punc-119::sGFP::NS(G392E) | pan-neuronal | Yes | Polymerigenic mutant |
| Pmec-4::sGFP::NS | mechanosensory neurons | Yes | Wild-type neuroserpin |
| Pmec-4::sGFP::NS(S49P) | mechanosensory neurons | Yes | Polymerigenic mutant |
| Pmec-4::sGFP::NS(G392E) | mechanosensory neurons | Yes | Polymerigenic mutant |
| Podr-10::sGFP::NS | chemosensory neurons | Yes | Wild-type neuroserpin |
| Podr-10::sGFP::NS(S49P) | chemosensory neurons | Yes | Polymerigenic mutant |
| Podr-10::sGFP::NS(G392E) | chemosensory neurons | Yes | Polymerigenic mutant |

Generation of ATZ Transgenic Animals.

Transgenic animals expressing AT were generated by injecting the plasmids in TABLE 2, into the gonads of young adult hermaphrodites at a concentration of 80 ng/µl. GFP-positive progeny were selected and propagated to confirm germline transmission. Injected DNA typically forms extra-chromosomal arrays that are transmitted (at rates ranging from 0-95%) to subsequent generations in a non-Mendelian manner. Stable, integrated lines, with 100% transmission rates, can be generated by exposing animals to high doses of gamma radiation. Apart from obviating the need for constant selection of GFP-positive worms under the fluorescent microscope, worms with integrated arrays display more stable and consistent transgene expression. Moreover, integrated lines are particularly advantageous for genetic screens and for experiments requiring analysis of large populations. For these reasons, stable, integrated lines were generated by exposing transgenic animals to 35Gy (3500 Rads) of gamma radiation. After stable integrants were identified, they were outcrossed 6 times to remove spurious mutations that may have been acquired as a result of the radiation treatment.

Figure 2A:
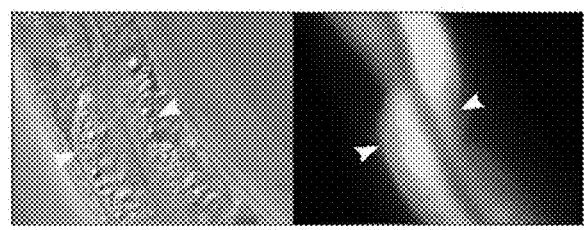
Figure 2B:
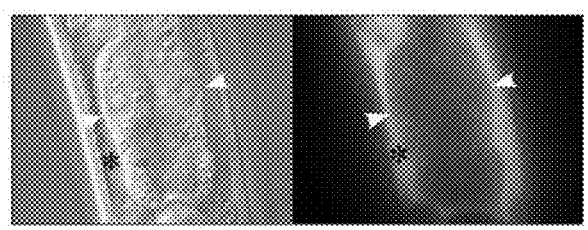
Figure 2C:
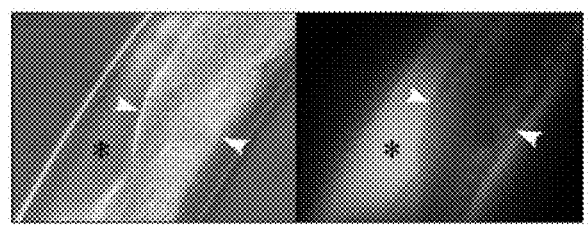
Figure 2D:
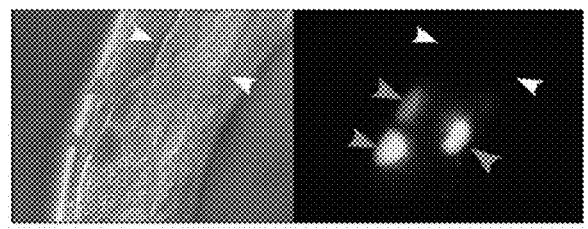
Figure 2E:
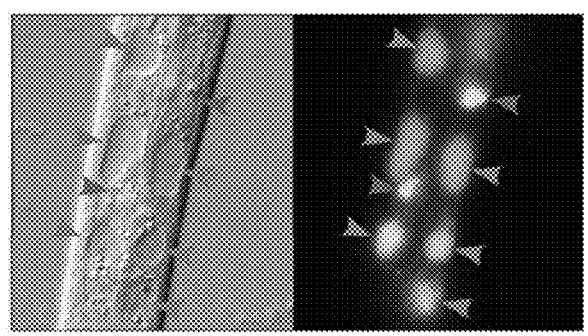

Although the intestinal specificity of the nhx-2-promoter has been described, the fate of intestinally secreted GFP (sGFP) was unknown. To address this issue, two constructs, Pnhx-2::GFP and Pnhx-2::sGFP, were prepared as positive controls for GFP secretion. Transgenic animals harboring Pnhx-2::GFP plasmids showed strong GFP expression in the intestinal cells (FIG. 2A). Transgenic animals harboring Pnhx-2::sGFP showed no visible GFP expression in the intestinal cells (FIG. 2B). Instead, diffuse GFP expression was seen in the pseudocoelomic space (FIG. 2B, asterisks). A similar expression pattern was observed in animals expressing ATM (Pnhx-2::sGFP::ATM) (FIG. 2C). These data indicated that the synthetic signal peptide of pPD95.85 was sufficient for directing the transgene to the ER-Golgi secretory pathway. In contrast, animals harboring the ATZ transgene (Pnhx-2::sGFP::ATZ) showed non-detectable levels of sGFP::ATZ in the pseudocoelomic space. Instead, bright intracellular GFP positive inclusions were observed (FIGS. 2D and 2E, red arrows), suggesting intracellular retention and aggregation. These observations closely resemble previous findings in human cell culture and mouse models and indicated that ATZ aggregation can be recapitulated in C. elegans.

To determine if correct fusion proteins were being synthesized, total worm lysates were analyzed by immunoblotting. Mixed staged worms were lysed by sonication. Following centrifugation to remove cell debris, worm lysates were boiled in sample buffer for 5 min and fractionated by SDS-PAGE. Gels were transferred to nitrocellulose membranes and AT and GFP protein bands were visualized by probing with anti-AT and anti-GFP antibodies, respectively (FIG. 3). The anti-human AT antibody did not react with any proteins in the lysates of the parental N2 (lane 1) or control sGFP (lane 2) expressing worms (FIG. 3A). In contrast, a protein band migrating at ~50 kDa, corresponding to the purified plasma AT, was recognized (lane 5). In addition, a protein band migrating at ~80 kDa was detected in the lysates of worms expressing sGFP::ATM (lane 3) and sGF-P::ATZ (lane 4) (FIG. 3A). To confirm that the ~80 kDa protein bands corresponded to sGFP::ATM and sGFP::ATZ fusion proteins, a parallel blot was probed with an anti-GFP antibody (FIG. 3B). Identically-sized protein bands were recognized by both antibodies (lanes 3 and 4) indicating that the ~80 kDa protein bands were indeed sGFP::ATZ or ::M) fusions.

To further characterize the nature and location of the ATZ globules, worms were fixed in glutaraldehyde, stained with osmium tetroxide and examined under an electron microscope (FIG. 4). No abnormal structures were observed in the intestinal cells of worms expressing sGFP::ATM (FIG. 4A). In contrast, large intracellular globules were present in sections of worms expressing sGFP::ATZ (FIGS. 4B and C, arrowheads). These globules appeared to be surrounded by ribosomes (FIG. 4D), suggesting retention of the ATZ proteins within the ER.

Development of a fully automated, high-content, high-throughput, whole organism-based screen for drugs and RNAis. *C. elegans* is a powerful genetic organism useful for the study of human diseases. Recently, there have been growing interest in using *C. elegans* as a tool in drug discovery. Efforts have been hampered by one major bottleneck—automated image capture and data analysis. The present invention now provides a fully automated, whole organism-based high-content screen (HCS) for drugs and RNAis modulating the disease phenotype. This method can be easily adapted to other *C. elegans* models and provides a stepping-stone for future *C. elegans*-based drug and RNAi screens.

The ability to conduct a high throughput drug screen depends largely on the capacity to rapidly and accurately detect and quantify the given phenotype. Prior to the present invention, automated image capture technology has focused largely on cells in culture. Image capture of multicellular, whole organisms is presented with numerous challenges such as autofocusing of the region of interest.

To determine whether the *C. elegans* model of ATZ could be used for high-content, high-throughput screens, a 96 well-based assay was developed. Fifty-five young adult stage worms were dispensed into 96-well plates using the COPAS BioSort (worm sorter). Worms were then immobilized by the addition of 0.1 M sodium azide to facilitate image capture. The plates were placed into a computerized high throughput plate reader, ArrayScanVTi (Thermofisher Cellomics Products). ArrayScanVTi was set up to rapidly scan wells and capture multiple images using bright field and fluorescence parameters. Complex algorithms were set up to identify and quantify defined objects (fluorescent granules) and events (individual animals). A typical screen shot of the ArrayScanVTi interface is shown in FIG. 5. In this case, bright field and GFP fluorescence images were taken from 4 different fields within each well using a 5× Carl Zeiss objective. A single field showing a bright field and GFP fluorescence overlay illustrates GFP aggregates throughout the length of the intestine (FIG. 5, well D1). To quantify these GFP aggregates, algorithms were developed to first identify the objects of interest (adult worms) and quantify the number and intensity of the spots (aggregates). FIG. 6 shows exactly the elements from FIG. 5 that were selected for data analysis. ArrayScanVTi correctly identified all adult worms in the field of view (blue outline) and excluded all eggs and other debris that would alter the analysis. Moreover, the algorithm identified all the ATZ aggregates (FIG. 6, red spots) within the set boundary (FIG. 6, red outline).

After defining the parameters to accurately identify worms and aggregates within ATZ worms, the sensitivity of the approach to discriminate between N2, sGFP::ATM and sGFP::ATZ animals was tested. In all cases, the algorithm identified correctly all adult worms in the field of view (FIG. 7, blue outline). As expected, no GFP aggregates were identified in N2 animals and a small number of "aggregates" were identified in sGFP::ATM animals. In contrast, numerous aggregates were identified within ATZ animals (FIG. 7, ATZ, red spots). To quantify the differences between the types of animals, the total number of spots and the total and average spot area for all 4 fields were determined by the algorithm (FIG. 8). Consistent with the fluorescence images, no aggregates (spots) were identified in the N2 animals. In contrast, >450 aggregates were identified in the well containing the sGFP::ATZ animals. A small number (<70) of spots were identified in the sGFP::ATM animals, however, the total and average spot areas were <5% and <20% that of ATZ animals, respectively. These results indicated that ATZ aggregates can be readily identified and quantified. These data also demonstrated the sensitivity of the system in detecting smaller and less intense aggregates, parameters that may be important for identifying compounds that induce a partial reduction in ATZ aggregation.

Although the above-mentioned method could discriminate between the various transgenic lines, the initial assay using the brightfield module was plagued with long focus times, inconsistent object identification and inaccurate determination of worm number per well. These problems are not limited to the Arrayscan VTi but to brightfield imaging in general. To circumvent these problems, a new transgenic AT lines that expresses a red fluorescent protein (mCherry) in the head (pharynx) region of the worm was developed (FIG. 9). The expression of a second fluorescent marker that has a distinct expression pattern than GFP::ATZ (intestine) has several major advantages. First, the bright expression of the mCherry protein significantly improves focus time and efficiency. Second, with optimized algorithms, red heads can be easily counted to obtain accurate worm number per well. Thirdly, since the pharynx is in the same focal plane as the intestine, GFP::ATZ aggregates can be more efficiently and accurately measured. By simply dividing the total GFP fluorescence in the well by the total number red heads, the average GFP fluorescence per worm can be determined, a capability that was problematic to achieve using the brightfield object identification algorithms.

Initial feasibility experiments were performed using 96-well plates. To increase the high-throughput capacity of the assays, a 384-well-based assay was developed. A 384-well-based assay has several advantages over the 96-well format. First, one can screen more compounds using the same number of worms needed for a 96-well plate. Second, images can be captured using the 2.5× objective. This reduces the number of fields needed to capture the well from 16 to 1. In addition, the Arrayscan VTi was fitted with a 0.63× coupler. The 0.63× coupler allows the capture of 100% of the well (as opposed to ~90% using the 1× coupler) allowing one to account for all the worms on in the well. This has lead to a considerably smaller variance between replicate wells.

Collectively, the ability to utilize an automated detection system to measure changes in the size and number of ATZ aggregates in individual animals cultured in 384-well plates removes the single most significant bottleneck/obstruction to the development of high throughput screening using a whole animal such as *C. elegans*.

A Small Molecule Screen of the LOPAC Library Identifies Drugs Potentially Useful for the Treatment of AT-Deficiency and Other Protein Aggregation Disorders.

To determine whether the *C. elegans* model could be used in a high-content, high-throughput drug screen context for modifiers of misfolded ATZ accumulation, a pilot screen of the LOPAC (library of pharmacologically active compounds) library was performed. The global strategy for high-throughput screen is shown in FIG. 10A-E.

Two μl of stock (10 mM) compounds were diluted with 98 μl of S-medium to a final concentration of 200 μM drug in 2% DMSO and S-medium. Fifteen μl of the diluted compounds were then transferred to 384-well plates using a robotic liquid handler (EP3). Prior to the experiment, fifteen μl of 4×OP50/antibiotic solution were added to each well. Using the COPAS Biosort, 35 L4-young adult stage worms were deposited into each well and allowed to incubate for 24 or 48 h at 22° C. At the end of the incubation period, worms were immobilized by the addition of sodium azide or levamisole to a final concentration of 12.5 mM and 4 mM, respectively. The worms were then imaged using the high speed, automated imaging device, ArrayScan VTi. Image capture and data analysis were performed using the Spot Detector BioApplication with algorithms optimized for worms. B-score statistical analyses were performed to identify compounds that had a significant (>2 SDs away from the mean) effect on ATZ aggregation. A summary of a typical LOPAC screen is shown in FIG. 11. Using the above approach, three screens of the LOPAC library were performed which identified a number of hit compounds that have potential therapeutic value (TABLE 4).

canonical expression vector, pPD49.26 (a kind gift from Dr. Andrew Fire, Stanford University School of Medicine), respectively. To generate the Pnhx-2mCherry::lgg-1 construct, a 3.5 kb genomic fragment containing the lgg-1 promoter, coding region and 3'-UTR was amplified and cloned into pCR®-Blunt II-TOPO® vector (Invitrogen, Carlsbad, Calif., USA). Using site directed mutagenesis a unique MluI restriction enzyme site, was introduced upstream of the lgg-1 translation start codon. The mCherry cDNA, lacking a translation stop codon, was inserted into the MluI site, which places it in-frame with the lgg-1 coding region. To direct expression of the mCherry::lgg-1 fusion gene in intestinal cells, we replaced the lgg-1 promoter with a 1.5 kb nhx-2 promoter using a HindIII restriction site. Pnhx-2sGFP::ATM was generated by inserting a 4 kb nhx-2 promoter fragment into HindIII/XbaI restriction sites of the expression vector, pPD95.85. Then a KasI restriction site was introduced by site-directed mutagenesis into the GFP translational stop codon. A 1.4 kb fragment containing the ATM cDNA and 3 synthetic introns was then cloned into the KasI site. Pnhx-2sGFP::ATZ was generated by site-directed mutagenesis of Pnhx-2sGFP::ATM, thereby generating the E342K (Z) mutation. The plasmid containing Pnhx-2GFP, pFH6IInhx-2, was a kind gift from Keith Nehrke (University of Rochester Medical Center) (59).

Worm Strain and Culture Conditions:

Worm strains: VK413 (Pnhx-2GFP), VK1093 (Pnhx-2mCherry::lgg-1), VK821 (Pmyo-2mRFP) were generated by injecting the respective plasmids into the gonad of young adult N2 hermaphrodites at a final concentration 80 ng/μl. Strains VK689 (Pnhx-2sGFP::ATM) and VK694 (Pnhx-2sGFP::ATZ) were generated by co-injecting the plasmids and Pmyo-2mRFP at a final concentration of 70 ng/ml and 10 ng/ml, respectively. The worm strain expressing Pclh-4GFP (pFL6IIclh-4) were a gift from Keith Nehrke 40. N2 and GF66 (Pvha-4Q82::YFP, 21) were obtained from *Caenorhabditis* Genetics Center (CGC), http://www.cbs.umn.edu/CGC/). Worms were routinely cultured at 22° C. on nematode growth medium (NGM) plates seeded with *E. coli* strain, OP50, unless otherwise specified.

Imaging of Transgenic Animals Using ArrayScan VTI:

Twenty N2 or transgenic L4-adult stage worms were transferred to 384-well plates containing 60 μl of PBS and anesthetized with 30 μl of 0.02 M NaAz prior to image capture. Images were acquired with the ArrayScan VTI HCS

TABLE 4

List of hit compounds

| Mol ID | Name | Description |
|---|---|---|
| 75 | W-7 hydrochloride | Calmodulin antagonist |
| 140 | H-89 | cAMP-dependent protein kinase (PKA) inhibitor |
| 248 | Cantharidin | Protein phosphatase 2A inhibitor |
| 249 | Chlorpromazine hydrochloride | Dopamine receptor antagonist; anti-emetic; antipsychotic |
| 275 | 4-Chloromercuribenzoic acid | Carboxy- and aminopeptidase inhibitor |
| 280 | Pyrocatechol | Carcinogen; causes DNA strand breakage |
| 291 | CGP-74514A hydrochloride | Cdk1 inhibitor |
| 318 | Cantharidic Acid | Protein phosphatase 1 (PP1) and 2A (PP2A) inhibitor |
| 396 | Dequalinium analog, C-14 linker | Protein kinase C-alpha (PKC-alpha) inhibitor |
| 553 | (−)-Eseroline fumarate | Metabolite of physostigmine (eserine); potent analgesic; cholinesterase inhibitor |
| 555 | Fluphenazine dihydrochloride | Dopamine receptor antagonist; antipsychotic |
| 600 | Idarubicin | Antineoplastic |
| 799 | Se-(methyl)selenocysteine hydrochloride | Potent chemopreventive agent |
| 946 | Pimozide | Ca2+ channel antagonist; antipsychotic; D2 dopamine receptor antagonist | listed in order of Mol ID

7. EXAMPLE: AUTOMATED HIGH-CONTENT LIVE ANIMAL DRUG SCREENING USING *C. ELEGANS*

7.1 Materials and Methods

Construction of Promoter-Transgene Fusions:

A transcriptional Pmyo-2mRFP fusion construct was constructed by subcloning the myo-2 promoter and the mRFP cDNA into the SphI/XbaI and NheI/EcoRV sites of the Reader (Cellomics, ThermoFisher, Pittsburgh, Pa., USA) fitted with a 5× or 2.5× objective and a 0.63× coupler. For the detection of various developmental stages using N2 worms, images were captured using the brightfield channel. Valid objects (adult worms) were automatically selected using the SpotDetector BioApplication (Cellomics). For image capture and analysis of the lines expressing fluorescent transgenes, we employed a 2-channel (brightfield and GFP or TRITC) assay. Algorithms were optimized to first identify valid objects (blue outline in FIGURES.), defined as non-overlapping, whole worms in the brightfield channel. Debris and partial worms were automatically excluded (orange outline in Figs.) from analysis. Fluorescent transgene expression, within valid objects, was quantified in the TRITC or GFP channels. SpotDetector BioApplication was optimized to identify transgene expression as spots. Parameters were optimized such that spots of varying shape, size and intensity could be identified. For this paper, spot count, spot total area and spot total intensity per object were used to compare transgene expression in different animals.

Whole Animal Alive-Dead Assay:

Adult N2; Is1033[Pmyo-2::mRFP] animals were incubated at room temperature with sodium azide (0-100 mM) for 4 hours. Animals were washed 5 times with M9 media and stained with 2 µM SYTOX™ Green (Invitrogen) for 5 minutes at room temperature (46). Approximately 50 animals/well were dispensed into an optical bottom black walled 96 well plate (Nunc Thermo Fisher Scientific, Rochester, N.Y., USA). Wells were imaged using the ArrayScan VTI over the entire area of the well in brightfield, red (TRITC) and green (GFP) channels at 50× magnification. The total number of animals and the number of dead bodies were determined by counting red and green spots, respectively. Data from SpotDetector algorithm were confirmed by manual counting of the live and dead animals. Percent dead=(the number of green objects detected/total number of animals)×100.

OP50 Preparation for Growth of Animals in Liquid Culture:

A single colony of OP50 was placed in 3 ml LB broth and incubated at 37° C. with vigorous shaking overnight. One milliliter of overnight culture was added to 1 L sterile LB broth and was incubated at 37° C. with vigorous shaking until reaching an OD600=0.5. The bacteria were washed twice with PBS and concentrated to an OD600=10.0. An equal volume of 50% glycerol was added for long-term storage at −80° C. After thawing, the bacteria were concentrated by centrifugation and re-suspended in PBS to an OD600=10.0.

Preparation of Animals for HCS Drug Screening:

Ten adult animals were placed on twelve 10 cm plates of NGM agar media spread with a lawn of *E. coli* strain OP50 (NGM/OP50). Approximately 7 days later, young adult stage F2 animals were isolated by differential sedimentation and transferred to 12 NGM/OP50 plates. After an overnight incubation at 22° C., adults were washed off with PBS and the remaining eggs were allowed to hatch overnight. Early-stage larvae were transferred to 48 NGM/OP50 plates and allowed to grow until most of the worms were in the 4th larval (L4) stage. Using the COPAS™ BIOSORT (Union Biometrica, Holliston, Mass., USA) approximately 15,000 L4 stage animals expressing similar levels of GFP were sorted into twelve 10 cm NGM/OP50 plates. After an overnight incubation at 22° C., gravid adults were washed off and transferred to fresh NGM/OP50 plates and allowed to lay eggs for 5 hours. Following this incubation period, adults were washed off and discarded leaving a synchronous population of eggs on the plates. The eggs were incubated at 22° C. for 40 hours or until the majority of the worms were in the L4/young adult stages. This method generated a population of ~200,000 age-synchronized animals for small molecule screening.

Compound Libraries and Handling, Dilution and Transfer to Assay Plates:

The 1280 compound Library of Pharmacologically Active Compounds (LOPAC) was purchased from Sigma-Aldrich (St. Louis, Mo., USA). Compounds were arrayed into 384-well microtiter master plates at a concentration of 10 mM in DMSO. LOPAC compounds were given unique University of Pittsburgh Drug Discovery Institute (UPDDI) substance identity numbers and were handled and stored as described (60-63). Daughter plates containing 2 µl of 10 mM compounds in DMSO were prepared and replicated from the LOPAC master plates using the Vprep (Agilent Technologies, Santa Clara Calif., USA) outfitted with a 384-well transfer head. Aluminum adhesive plate seals were applied with an Abgene Seal-IT 100 (Rochester, N.Y., USA) plate sealer and plates were stored at −20° C. in a Matrical MatriMinistore™ (Spokane, Wash., USA) automated compound storage and retrieval system. For the primary screen, daughter plates were withdrawn from the −20° C. freezer, thawed at ambient temperature and centrifuged 1-2 min at 50×g. The plate seals were removed and 98 µl of S-medium were added to the wells using the Flex Drop dispenser (Perkin Elmer, Waltham, Mass., USA). This intermediate stock of library compounds was at a concentration of 200 µM in 2% DMSO. The diluted compounds were mixed by repeated aspiration and dispensation using a 384-well P30 dispensing head on the Evolution-P3 (EP3) liquid handling platform (Perkin Elmer), and then 15 µl of each compound were transferred to the wells of assay plates. In the primary screen, compounds were screened individually at a final concentration of 50 µM.

Assay Plate Preparation for Drug Screen:

On the day of the screen, assay plates containing 15 µl of each compound were thawed and centrifuged at 214×g for 60 s. Fifteen microliters of 4× assay medium, which was prepared by mixing 4.0 ml OP50, 25.4 ml S-medium, 0.6 ml 100× antibiotic-antimycotic stock solution (stock contained 10,000 units penicillin, 10 mg streptomycin and 25 µg amphotericin B/ml, Sigma) and 24.0 µl 1 M FUDR, were added to each well. Animals were then sorted into the wells using the COPAS™ BIOSORT worm sorter.

Animal Sorting Using the COPAS™ BIOSORT:

To reduce assay variability, a tightly-synchronized population of worms was selected based on size (i.e., stage of development) and fluorescence intensity (i.e., transgene expression) using the COPAS™ BIOSORT. L4 to young adult-stage worms were initially selected using empirically-determined time-of-flight (TOF) and coefficient of extinction (EXT) values. Animals were also gated based on GFP fluorescence intensity. Approximately 30% of the starting population was selected. For analytical assays, animals were suspended in S-medium (minus EDTA) for sorting. The flow rate was maintained at ~25 worms/sec. Coincidence check was employed to enhance selection specificity. For LOPAC library screening, COPAS sheath fluid was replaced with 0.01% Triton X-100 in S-medium (minus EDTA) to promote healthy bacteria and worm growth. Thirty-five L4 to young-adult animals were sorted into wells containing compounds and assay medium. The final total volume per well after addition of the animals was 60 µl. Approximately 45,000 worms were required for each 384-well plate. On average, sorting time was 90 minutes per plate. The flow cell was periodically flushed between plates to prevent clogging. Four 384-well plates were routinely sorted on the same day. Plates were then sealed with ThinSeal T-2417-4 (ISC Bio-Express, Kaysville, Utah, USA) and incubated at 22° C. for 24-48 hours.

Imaging of Animals Using the ArrayScan VTI:

Prior to imaging, worms were anesthetized by adding 30 µl of 0.02 M NaN3 in PBS to each well. Plates were resealed, inverted twice, and incubated for 5 minutes at room temperature. Images were acquired with the Array-Scan VTI HCS Reader fitted with a 2.5× objective and a 0.63× coupler using a 2-channel (TRITC and GFP) assay. Real-time analysis was performed using the SpotDetector BioApplication optimized to quantify fluorescent protein expression in *C. elegans*. Image acquisition and analysis of a 384-well plate was completed in <45 minutes. The total number of animals in the well was determined by counting the number of red heads (Pmyo-2mRFP) in the TRITC channel. Total spot area or total spot intensity was determined by quantifying the GFP-positive spots in the GFP channel. Total spot area or total spot intensity per animal was determined by dividing the values from the GFP channel by that from the TRITC channel.

HCS Data Analysis:

Compound tracking and data analysis for the primary HCS assay were performed using ActivityBase™ (IDBS, Guildford, UK), CytoMiner (UPDDI) software and visualized using Spotfire™ DecisionSite® (TIBCO Software Inc., Somerville, Mass., USA) software, as described in 60-63. Custom calculators were written to process the HCS data and perform the z-score and B-score statistical analysis (64,65).

As a measure of assay quality and robustness, the Z'-factor 30 was used. The Z'-factor was calculated from the mean and the standard deviation of the negative and positive control populations as follows:

$$Z'=1-((3\times(\sigma_p+\sigma_n))/(\mu_p-\mu_n))$$

where σ is the standard deviation, µ is the mean and p and n are positive and negative controls, respectively. Z'-factors between 0.5 and 1.0 indicate the separation band (signal window) between the positive and negative controls is wide and the assay is of excellent quality and suitable for HTS/HCS. Z'-factors between 0 and 0.5 indicate a good quality screen, whereas a score <0 indicates the assay is of poor quality and unsuitable for HTS/HCS.

The z-score plate-based statistical scoring method was used as described previously to identify compounds that behaved as statistical outliers compared to the other substances (n=320, no controls) tested on an assay plate for selected HCS multi-parameter measurements output by the image analysis module (62). The z-score=$(X_i-\bar{X})/\sigma$, where $X_i$ was the raw measurement on the ith compound, and X and σ were the mean and standard deviation of all the sample measurements on a plate.

The B-score was calculated from all of the sample measurements on an assay plate and used an iterative mathematical model to eliminate systematic row and column artifacts on a plate. The mathematical model of the B-score was described as:

$$Y_{ijp}=\mu_{ijp}+YR_{ip}+YC_{jp}+\epsilon_{ijp}$$

where $Y_{ijp}$ was the compound measurement at $i_{th}$ row and $j_{th}$ column of the $p_{th}$ plate, $\mu_{ijp}$ was the 'true' activity value, $\epsilon_{ijp}$ was the random error of the assay on the $p_{th}$ plate, and $YR_{ip}$ and $YC_{jp}$ represented the row and column artifacts on the pth plate, respectively. A two-way median polish statistic method was applied to estimate the B-score of a HCS assay. The implemented procedures are described below. The random error estimate, $\hat{\epsilon}_{ijp}$, of the measurement at $i_{th}$ row and $j_{th}$ column of the $p_{th}$ plate was calculated by fitting a two-way median polish as:

$$\hat{\epsilon}_{ijp}=Y_{ijp}-\hat{Y}_{ijp}=Y_{ijp}-(\hat{\mu}+\hat{R}_{ip}+\hat{C}_{jp})$$

where $\hat{Y}_{ijp}$ was the fitted compound value, $\hat{\mu}$ was the estimated average of the plate, and $\hat{R}_{ip}$ and $\hat{C}_{jp}$ were the estimated systematic artifacts for the $i_{th}$ row on $p_{th}$ plate and $j_{th}$ column on $p_{th}$ plate, respectively. Next the median absolute deviation (MAD) of the random error estimate on $p_{th}$ plate was computed as:

$$MAD_p=Median\{|\hat{\epsilon}_{ijp}-Median(\hat{\epsilon}_{ijp})|\}$$

At the last step, the B score was calculated as:

$$B-score=\frac{\hat{\epsilon}_{ijp}}{MAD_p}$$

The compounds were ranked according to ascending B-score values. Rank-scores were calculated by taking the average of compound rankings from two independent drug screens. Compounds with rank-scores <110 significantly decreased the accumulation of sGFP::ATZ inclusions. Conversely, compounds with rank-scores >1225 significantly increased the accumulation of sGFP::ATZ inclusions. Selected compounds (based on cost and availability) from both groups were chosen for further analysis.

Hit Compound Characterization:

Compounds that were identified as potential hits were purchased (if available) and retested for verification. Compounds that failed to produce a dose-dependent response were not analyzed further. Compounds that produced a response in a dose-dependent manner were further tested for a time-dependent response. Compound dose-response curves were performed by dispensing 15 µl of a 4× stock solution into 384-well plates containing 15 µl of assay medium (see above). Thirty-five animals were sorted into each well bringing the volume to ~60 µl. The final compound concentrations in each well varied from 0-100 µM. Assay plates were incubated in a 22° C. incubator for 24 or 48 hours. Each compound was tested in quadruplicate in at least 2 independent experiments.

Statistical Evaluation:

Statistical evaluation of data was performed using Prism® (Graphpad Software). The significance of actual and predicted data in FIGS. 12, 14 and 15 was determined using a linear regression analysis and comparing the slope and goodness-of-fit (r2) values. Statistical significance of the spot count, spot area and spot intensity values between N2 (wild-type) and various transgenic lines in FIG. 13 and dose-response in FIG. 17 was determined using an unpaired, one-tailed, Student's t-test.

7.2. Results

Figure 12A:
Figure 12B:
Figure 12C:
Figure 12D:
Figure 12E:
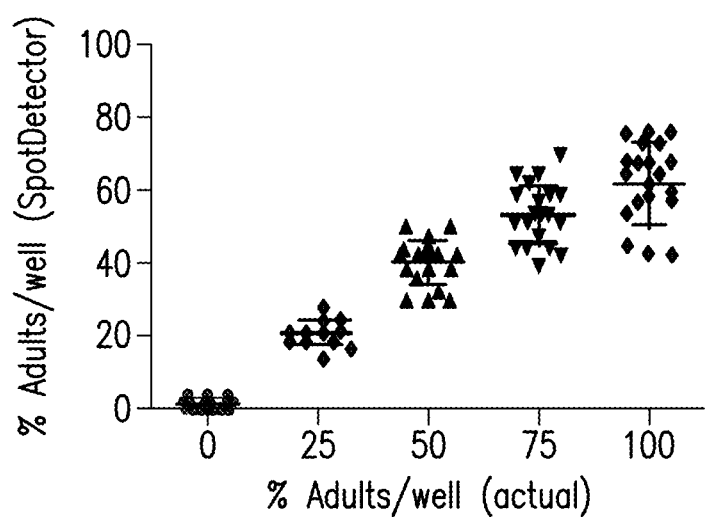

Detection of *C. elegans* Developmental Stages Based on Size:

An automated fluorescence microscopy imaging system by Cellomics, Inc., originally designed for HCS and data analysis using cells (http://www.cellomics.com/content/menu/ArrayScan/), was adapted to automate the detection and analysis of *C. elegans* in a 96- or 384-well microtiter format. The instrument, ArrayScan VTI, consists of an inverted light microscope (Axiovert 200M, Carl Zeiss) configured with a motorized objective turret with Plan-Neofluar objectives, a motorized 5-position filter cube turret, a mechanized stage, a 12-bit cooled CCD camera and controller software. Samples are illuminated for brightfield imaging using a broad white-light source and for florescence imaging in up to 4 different spectra using a mercury-based light source. Different types of analysis modules (Thermo Scientific BioApplications) automatically convert 16-bit monochromatic images into numeric data. To determine whether the ArrayScan VTI and the BioApplications software could distinguish accurately small animals instead of cells, the numbers of young adult C. elegans sorted into a 384-well plate were first assessed (FIG. 12A). The software application required that objects first be defined and counted in channel 1. Using brightfield illumination, the SpotDetector BioApplication, which was programmed to detect objects of a certain size, identified nearly all the adult animals (FIG. 12B, outlined in blue). Since the algorithm also excludes objects of a certain size, it was determined whether, the system could distinguish young adult animals from eggs and the smaller L1 through L4 larval forms. Populations of 36 animals, each containing different percentages of adult worms were sorted into 384-well microtiter plate (FIG. 12C). The SpotDetector BioApplication correctly selected (outlined in blue) and excluded (outlined in yellow) objects of the pre-selected size parameters (FIG. 12D). However, some animals were not counted in wells containing a higher proportion of adults. Miscounting, which decreased the overall goodness-of-fit of linear regression, was due to the inability of algorithm to resolve overlapping patterns into more than one discrete object (FIG. 12E). As expected, the accuracy of detection improved when <10 adults were added to a well. Of note, the program can be configured to detect animals at, for example, the L1-L2 stage and exclude those at the L3-L4 adult stages. Taken together, these studies suggested that the instrument could be used to screen for compounds that alter the growth and development of synchronized cultures by counting the proportion of animals of a particular size at a constant time point.

Detection of Tissues, Pathologic Subcellular Protein Aggregates and Autophagy within C. elegans:

Once valid objects are selected using the brightfield images in channel 1, the ArrayScan VTI can detect fluorescent "spots" in up to 4 different channels within each object and the SpotDetector BioApplication can display the data as a total fluorescent spot number, spot area or spot intensity per object. It was next determined whether this application was sensitive enough to identify different cell types (pharyngeal cells, excretory cell, intestinal cells), pathologic protein deposition (polyQ aggregates) or a physiological process (autophagy) within individual objects (animals). Fluorescent images (channel 2) were obtained for C. elegans strains carrying transgenes with tissue-specific promoters driving fluorescent protein expression in the pharynx (Pmyo-2RFP), the excretory gland cell (Pclh-4GFP) or intestinal cells (Pvha-6Q82::YFP, Pnhx-2GFP or Pnhx-2mCherry::lgg-1). Except for the polyQ82-containing construct, which generates cytosolic aggregates {40}, the others yielded a diffuse cytoplasmic fluorescence pattern under baseline conditions (FIGS. 13A-13J). In comparison to the minimal background fluorescence of wild-type (N2) animals, that of the transgenic animals was markedly increased using the SpotDetector BioApplication to measure either the total spot number, area or fluorescence intensity per animal (FIGS. 13O-13Q). Depending on the nature of the transgene expression pattern, certain comparisons were more meaningful. For example, total spot area or total spot intensity per animal, rather than total spot count, were better at discriminating pharyngeal or intestinal expression in comparison to background (FIGS. 13C-13F, 13P, 13Q). In contrast, total spot count per animal, was the more sensitive parameter to follow when assessing the presence of the secretory cell and the degree of protein aggregation in the animals expressing polyQ82 (FIGS. 13G-13J, 13O).

Macroautophagy is a cellular process in which a double membrane envelops cytosolic components or organelles (autophagosome) and delivers this material to a lysosome (autophagolysosome) for degradation and recycling (reviewed in 41). LGG-1/LC3/Atg8 is a diffuse cytosolic protein that participates in autophagosome formation and becomes inserted into the autophagosome membrane (42). Upon autophagosome formation, LGG-1 fused to mCherry changes its cytoplasmic distribution pattern from diffuse (lower fluorescence intensity) to punctate (higher fluorescence intensity) (42). To determine whether the imaging system could follow this process, a strain expressing a Pnhx-2mCherry::lgg-1 transgene was examined after starvation, a potent inducer of intestinal autophagosome formation (43). In well-fed animals, the diffuse cytoplasmic fluorescence in the intestinal cells was well above that of the N2 background (FIGS. 13K-13L, 13O-13Q). To detect mCherry::LGG-1 puncta, the diffuse fluorescence intensity of the well-fed animals was used to calibrate a threshold from which the SpotDetector BioApplication could detect any high-intensity spots. Although basal autophagy in the well-fed animals yielded a few spots (FIG. 13O), the large number of distinct puncta in the starved animals (FIGS. 13M, 13N, 13O-Q) indicated a marked increase in autophagy that was detected best by a statistically significant increase in spot count or total spot intensity per animal (FIGS. 13O and 13Q, respectively). Taken together, this versatile imaging platform quantitatively measured several different types of fluorescence patterns, thereby allowing for the interrogation of a wider range of biological processes, such as tissue organization, proteotoxicity and metabolic functions.

Detection of Live Cells and Dead Animals.

The nematode has served as an informative system to study the genetics of different modes of cell death. It was determined whether this imaging system could distinguish between live or dead cells using either the loss or gain of a fluorescent marker, respectively. mec-4, a member of the DEG/ENaC membrane cation channel superfamily, is expressed exclusively in the 6 mechanosensory neurons of C. elegans (44). A reporter strain containing an integrated transgene, ZB164 bzIs8[Pmec-4GFP]; mec-4(+), diving GFP expression in the mechanosensory neurons exhibits ~4-5 fluorescent cell bodies per L4/young adult animal (45). In contrast, post-developmental necrotic cell death gradually occurs in most of the mechanosensory neurons after the reporter strain is crossed with animals containing a toxic gain-of-function mutation, mec-4(d). To determine whether the imaging system could distinguish the wild-type from the mec-4(d) strain, adult animals were identified by brightfield illumination in channel 1 (FIGS. 14A, 14D, 14G), and for comparison, by fluorescence imaging to display the GFP-labeled mechanosensory neurons in channel 2 (FIGS. 14B, 14E, 14H). SpotDetector quantified the number of live florescent cells (spots) present in each brightfield object (FIGS. 14C, 14F, 14I). Consistent with previous studies, the mec-4(+) and mec-4(d) strains averaged ~6 and ~2 cells/animal, respectively (FIG. 14M)(45). Remarkably, the system was capable of discriminating between wild-type and mutant animals based on the differential viability of just six mechanosensory neurons.

Animals exposed to toxic doses of sodium azide (NaAz) undergo massive necrotic intestinal cell death characterized by a marked loss of membrane permeability (46). Thus, the uptake of the membrane impermeant fluorescent nucleic acid dye, SYTOX® Green, serves as a dead cell indicator. To determine whether the system could discriminate dead from live intestinal cells, we scanned and analyzed young adult animals exposed to different concentrations of NaAz in the presence SYTOX® Green. Dead animals showed extensive uptake of SYTOX® Green that was accurately detected by the imaging system (FIGS. 14J-14L). Analysis showed a dose dependent increase in the number of dead animals and an excellent correlation with the number counted manually (FIG. 14N). It was concluded that this automated system was capable of detecting dead cells and should prove useful in developing HCS for drugs that modulate necrotic cell death.

Development of a HCS Protocol Using *C. elegans*:

Although brightfield imaging in channel 1 accurately detected adult animals (objects) in the well of a 384-well plate (FIG. 12), the time required to autofocus and capture each animal, plus a need to limit the adult worm population to ~10 animals per well (due to overlapping) decreased throughput and assay robustness. To obviate these problems, Pmyo-2mRFP transgenic animals that expressed the fluorescent protein in their pharyngeal region were used (FIG. 13F). Since the total fluorescence area or total fluorescence intensity of this region was proportional to the overall size and developmental stage of the animals, it was determined whether fluorescence imaging of the "red-heads" using these parameters could be substituted for the more time-consuming brightfield imaging. As above (FIG. 12), populations of 36 transgenic animals were sorted, each containing different percentages of adult worms, into the wells of 384-well microtiter plate. A composite brightfield and fluorescence image showed that all of the animals had a detectable red-head that was proportional in area to the developmental stage and size of the animal (FIG. 15A). Next, brightfield optics were preset in channel 1 to detect the entire well as a single "object". Once an object was defined in channel 1, the SpotDetector BioApplication was programmed to select (pseudocolored red heads) or exclude (pseudocolored white heads) fluorescent spots above or below, respectively, a pre-determined threshold value based on a combination of fluorescent spot area and intensity (FIG. 15B). In this example, the algorithm correctly identified all 9 young adult animals and excluded ~24 of the larval forms (FIG. 15B). Since, the area of the red-heads was proportionally smaller than that of adult animals, the total count was rarely confounded by overlapping pharyngeal "spots". Thus, there was excellent correlation between the number of adult animals detected by the spot count and the actual number of animals in the wells (FIG. 4C). It was concluded that the number of adult animals accurately detected in a well of a 384 well plate increased from 10 to at least 35, when fluorescence imaging of the red-head marker, rather than the brightfield imaging of individual animals was used to obtain a valid animal count.

Figure 16G:
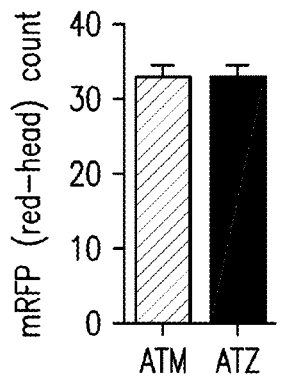
Figure 16H:
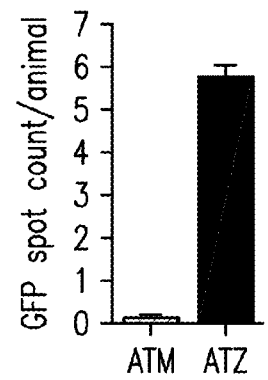
Figure 16I:
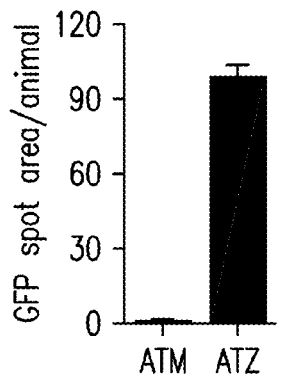
Figure 16J:
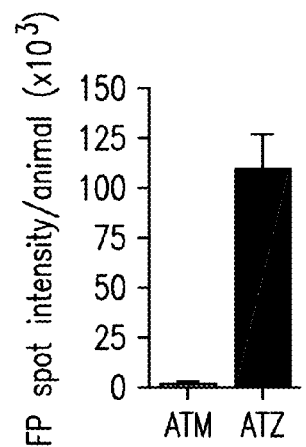

Since the imaging system can detect fluorescent "spots" in more than one channel, it was next determined whether a combination of two different fluorescent markers could be used to develop a high-content drug screening strategy using live animals. First, we developed an integrated transgenic line expressing the Z-mutation of the human secreted serpin, α1-anitrypsin (ATZ). This transgene, Pnhx2sGFP::ATZ, contains a human ATZ minigene fused C-terminal to GFP with N-terminal signal peptide (sGFP). An intestinal-specific promoter, nhx-2, drove fusion gene expression (47). In humans, this common Z mutation induces protein misfolding and accumulation within the endoplasmic reticulum of hepatocytes resulting in cellular injury and cirrhosis (reviewed in 48). Similarly, sGFP::ATZ aggregated within the endoplasmic reticulum of intestinal cells. As a control, an integrated transgenic line, expressing the wild-type fusion protein, sGFP::ATM. was generated. This protein was efficiently secreted into the intestinal lumen and pseudocoelomic space and was detectable microscopically only after a relatively long integration time. To facilitate analysis using the ArrayScan VTI, both strains were co-injected with the Pmyo-2mCherry transgene. Approximately 35 animals expressing sGFP::ATZ or sGFP::ATM were sorted into 384-well plates. To minimize variability, only Pnhx2sGFP::ATZ animals within a tight fluorescence window were sorted into the wells. Nearly the entire well was imaged in channel 1 using brightfield illumination (FIGS. 16A, 16D). These images, which were not used to identify individual animals, simply confirmed that that comparable numbers of young adult animals of both lines were sorted into the wells. Using channel 2 and 3, respectively, SpotDetector identified the red heads (FIGS. 16B, 16E) and either sGFP::ATM (barely detectable at the integration time used, FIG. 16C) or sGFP::ATZ (FIG. 16F) expression in the two different transgenic lines. Next, the red-heads detected in channel 2 were used to determine a "head count" and to show that the actual number of animals sorted into each well were nearly identical (FIG. 16G). Finally, the images obtained in channel 3 were used to measure three different parameters in each of the wells containing sGFP::ATM or sGFP::ATZ expressing animals (FIGS. 16H-16J). Data analysis indicated that the total GFP intensity, number of GFP spots or GFP area divided by the head count (i.e., parameter average per animal) were significantly increased in the sGFP::ATZ as compared to the sGFP::ATM expressing animals (FIGS. 16H-16J). Indeed, at the integration time used, sGFP::ATM expression was not significantly above that of wild-type animals.

Figure 16K:
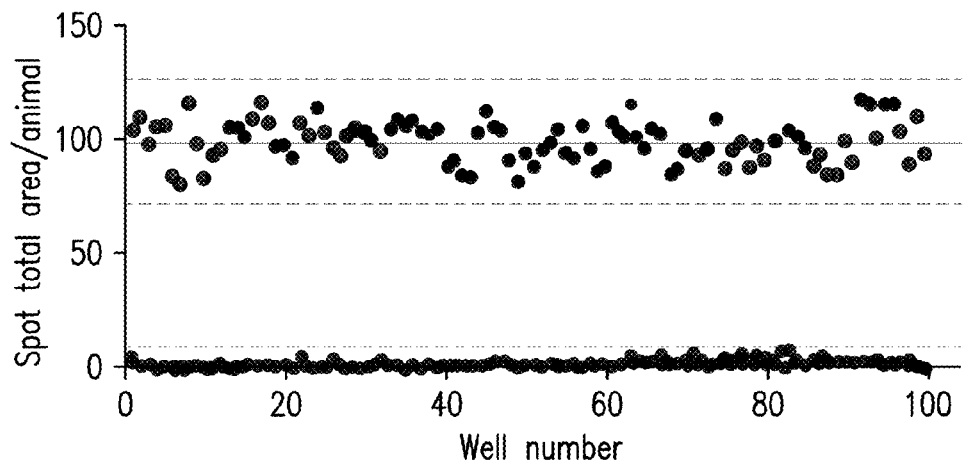
Figure 17:
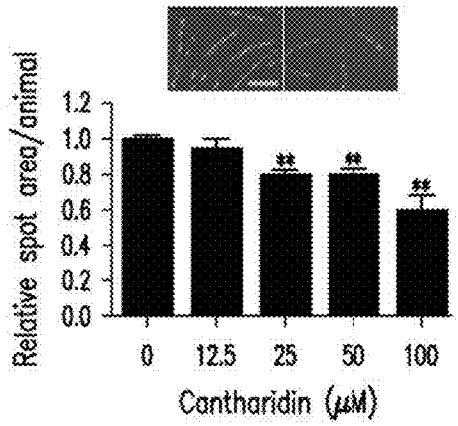
Figure 17:
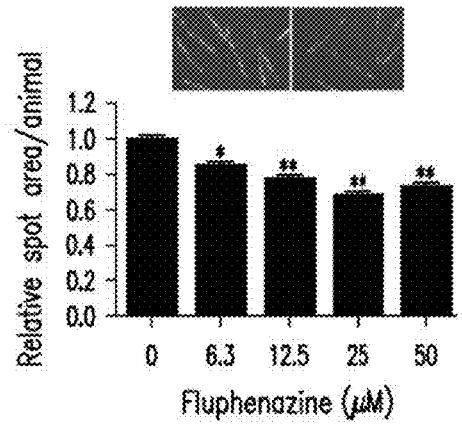
Figure 17:
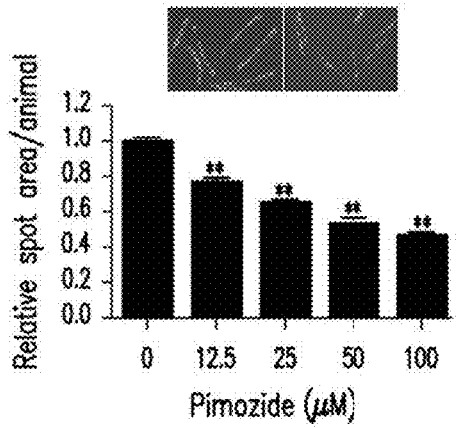
Figure 17:
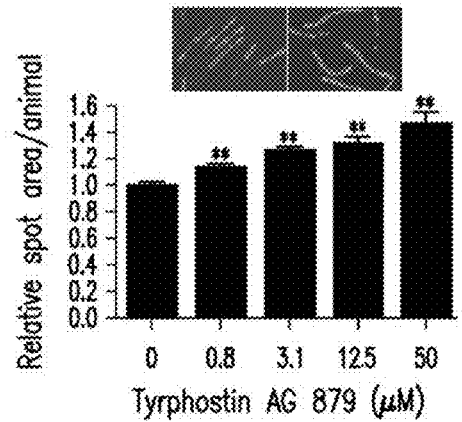
Figure 17I:
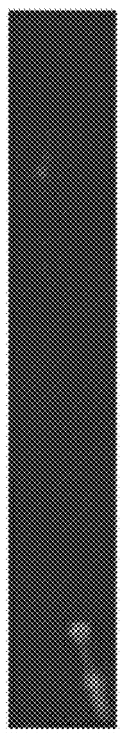
Figure 17K:
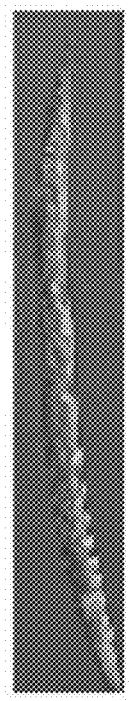
Figure 17H:
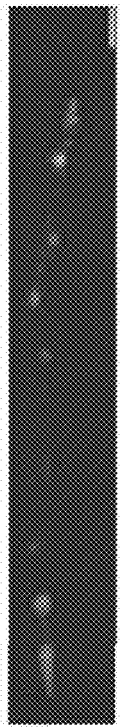
Figure 17J:
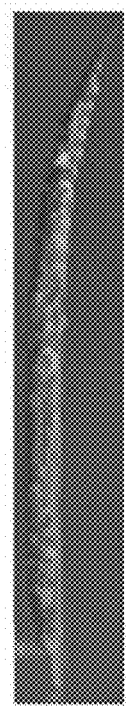
Figure 18A:
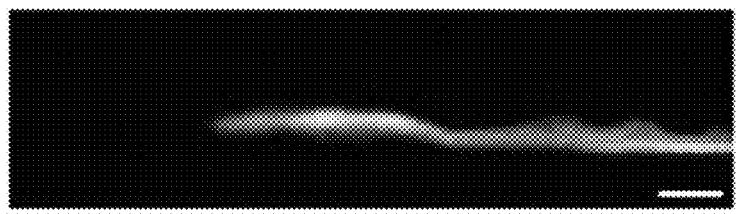
Figure 18B:
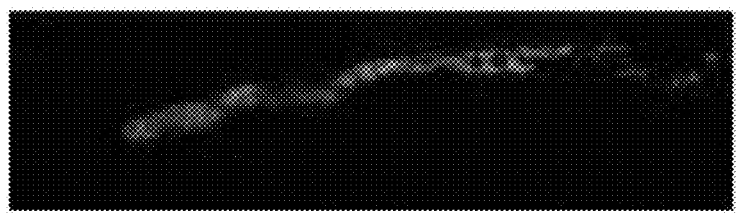
Figure 18C:
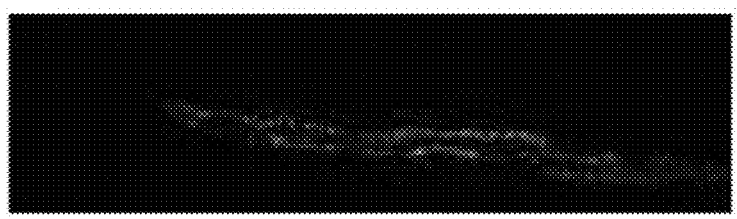
Figure 18D:
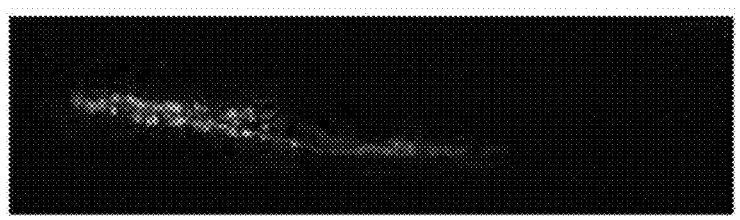
Figure 18E:
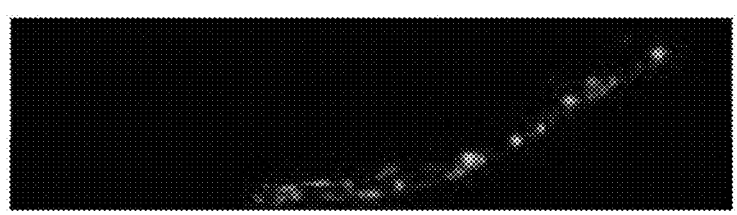

From these data it was concluded that the steady-state amounts of sGFP::ATZ in the transgenic line as compared to the control animals provided a dynamic range amenable to screening for compounds that altered sGFP::ATZ accumulation. However, prior to initiating a HCS campaign, the overall quality of the assay, using the Z'-factor as a metric, was tested (49). The Z'-factor, which is calculated from the mean and the SD of the negative and positive control populations, is a good indicator of the assay quality, robustness and reproducibility. Values between 0.5 and 1 are considered excellent and necessary before embarking upon a HTS/HCS campaign. To determine the quality of this assay, 180 wells containing wild-type and sGFP::ATZ animals were imaged using the ArrayScan VTI. In a representative experiment, the mean total spot area per sGFP::ATM and sGFP::ATZ animals were 0.2+0.7 and 194+22.4, respectively (FIG. 16K). The Z'-factor for this assay was ~0.7. Within a single experiment (sort) the Z factor remained constant form plate-to-plate. However, the Z'-factor would vary as much as 0.4 to 0.7 from day-to-day depending mostly on the size of the sort-window used to select the Pnhx2sGFP::ATZ animals.

Compound Screen:

To test the HCS protocol, a pilot drug screen was performed using the library of pharmacologically active compounds (LOPAC1280™, 1280 compounds). Tight gating parameters for total fluorescence were used to sort 35 young adult Pnhx2sGFP::ATZ animals into wells of 384-well plates containing 50 μm of a LOPAC compound and 0.5% DMSO. Pnhx2sGFP::ATZ animals incubated with 0.5% DMSO served as untreated controls and were placed in the first-two and last-two columns of each plate. In a representative experiment, plate 1 of the LOPAC library was set-up for screening on day 1, and 3 other plates were set-up on the next day. After 24 incubation at 25° C., animals were immobilized by the addition of NaAz and placed in the ArrayScan VTI for automated imaging. To examine for systematic errors, the raw data (total spot area/animal) were depicted as a plate-well scatter plot (FIG. 17A). From these data, a small amount of drift was seen in plate 1 in comparison to plates 2-4. This difference reflects a wider sort-window used to collect animals on day 1 in comparison to that used on day 2. As the average values of the negative controls and that of the sample wells were similar, we combined the control and samples wells for normalization and to identify potential hits using the z-score (FIG. 17B). The ArrayScan VTI reads microtiter plates by rows, alternating from left-to-right, and then right-to-left. For some assays, we noted that the control fluorescence values would drift upwards slightly in rows towards the bottom of the plate. This drift appeared to correlate with an increase in chamber temperature during the scanning period and was minimized by cooling the chamber with a fan or shortening the read times by using 2.5× objective with a 0.6 coupler. Nonetheless, intra-plate variation was controlled for by presenting the data as a B-score (FIG. 17C). Under the same conditions, the entire screen was repeated on a single day. An average rank-score was created for each compound by first compiling a list for each screen based on ascending B-scores, and then calculating the average rank for each compound (TABLE 5). To verify potential hits, we arbitrarily focused on those compounds with rank-scores <110 (n=33) or >1225 (n=15). Generally, compounds with these rank-scores had B-scores lesser or greater than 3 in at least one of the screens, and demonstrated the ability to significantly decrease or increase sGFP::ATZ accumulation, respectively. Based on cost and commercial availability, we selected 16 compounds to test for dose-dependent effects (TABLE 5). Cantharidin (FIG. 17D), fluphenazine (FIG. 17E) and pimozide (FIG. 17F) were representative examples of 6 of 12 compounds that showed a dose-dependent decrease in sGFP::ATZ accumulation; whereas tyrphostatin (FIG. 17G) was an example of 3 of 4 compounds that showed an increase in sGFP::ATZ accumulation. Interestingly, all three compounds that decreased GFP::ATZ accumulation were isolated previously in screens for compounds that enhance autophagy, an known elimination pathway for ATZ (53, 54). When animals expressing the Pnhx-2mCherry::lgg-1 transgene were treated, the distribution of mCherry::LGG-1 changed from diffusely cytosolic to punctate, suggesting an increase in the number of autophagosomes (FIG. 18). Taken together, these studies suggest that this screening assay was capable of identifying hit compounds that significantly altered sGFP::ATZ accumulation. A dose-response effect for pimozide and fluphenzine is demonstrated in FIG. 19 and FIGS. 20 and 21, respectively.

TABLE 5

| Rank-score[a] | Overall rank-order[b] | Potential hit compound |
|---|---|---|
| Compounds that decreased ATZ accumulation: | | |
| 2.0 | 1 | ivermectin[d] |
| 2.5 | 2 | cantharidin[c] |
| 10.5 | 3 | L-655,240 |
| 24.0 | 4 | GR 125487 sulfamate salt |
| 28.0 | 5 | muscimol hydrobromide |
| 34.5 | 6 | DL-homatropine hydrobromide |
| 36.5 | 7 | L(−)-norepinephrine bitartrate[d] |
| 41.5 | 8 | N-(2-[4-(4-Chlorophenyl)piperazin-1-yl]ethyl)-3-methoxybenzamide |
| 51.0 | 9 | cefmetazole sodium[d] |
| 52.5 | 10 | HA-100 |
| 56.0 | 11 | SB 206553 hydrochloride |
| 57.5 | 12 | L-701,324 |
| 57.5 | 13 | phenamil methanesulfonate[d] |
| 58.0 | 14 | rolipram |
| 61.0 | 15 | doxepin hydrochloride[d] |
| 61.5 | 16 | beta-chloro-L-alanine hydrochloride |
| 65.0 | 17 | S(−)-UH-301 hydrochloride |
| 72.5 | 18 | L-alpha-methyl DOPA |
| 73.5 | 19 | taxol[c] |
| 74.0 | 20 | cis-(Z)-flupenthixol dihydrochloride |
| 75.5 | 21 | 10-(alpha-diethylaminopropionyl)-phenothiazine hydrochloride |
| 79.0 | 22 | cantharidic acid[c] |
| 81.0 | 23 | fluphenazine dihydrochloride[c] |
| 83.5 | 24 | tamoxifen citrate[c] |
| 85.0 | 25 | indirubin-3'-oxime |
| 89.5 | 26 | (−)-bicuculline methbromide, 1(S), 9(R) |
| 90.0 | 27 | cephradine |
| 93.0 | 28 | indatraline hydrochloride |
| 95.5 | 29 | 5-carboxamidotryptamine maleate |
| 98.0 | 30 | tyrphostin AG 112 |
| 103.5 | 31 | prochlorperazine dimaleate |
| 105.5 | 32 | B-HT 933 dihydrochloride[d] |
| 107.5 | 33 | pimozide[c] |
| Compounds that increased ATZ accumulation: | | |
| 1263.0 | 1 | GW2974 |
| 1256.0 | 2 | thapsigargin[c] |
| 1255.0 | 3 | SB 224289 hydrochloride |
| 1255.0 | 4 | clotrimazole |
| 1253.5 | 5 | IC 261 |
| 1245.5 | 6 | tetradecylthioacetic acid |
| 1245.0 | 7 | tyrphostin 1 |
| 1240.5 | 8 | (+)-bromocriptine methanesulfonate |
| 1238.0 | 9 | L-162,313 |
| 1236.5 | 10 | tyrphostin AG 879[c] |
| 1236.5 | 11 | IIK7 |
| 1234.0 | 12 | glipizide[d] |
| 1233.5 | 12 | WIN 62,577 |
| 1231.0 | 14 | (R)-(+)-WIN 55,212-2 mesylate |
| 1229.5 | 15 | rottlerin[c] |

[a]Rank-scores were calculated by averaging compound rankings based on ascending B-scores from two independent drug screens. Compounds with rank-scores <110 or >1225 significantly decreased or increased the accumulation of sGFP::ATZ inclusions, respectively.
[b]Overall rank-order, based on relative rank-scores, for compounds that decreased or increased sGFP::ATZ accumulation.
[c]Compound demonstrated a dose-dependent response.
[d]Compound failed to demonstrate a dose-dependent response.

7.3 Discussion

Prior to the instant invention, two major obstacles have blocked the use of small animals, such as *C. elegans*, in high-throughput, high-content screening protocols: the absence of 1) a high-quality assays and 2) an automated system to capture, analyze and store data documenting the biological effects of thousands of compounds (39). In the experiments discussed herein, in order to improve assay quality, focus was initially placed on parameters that affected sample population variability. Despite using integrated and staged transgenic lines, the fluorescence intensity of the sGFP::ATZ-expressing animals varied two-fold. This variability was minimized in the assay population by using the COPAS™ BIOSORT to collect a precise number of animals using a tightly-gated fluorescence intensity window. The growth conditions in the microtiter wells also had a profound affect on assay quality. C. elegans Maintenance Medium (a chemically defined, bacteria free medium) appeared to be an ideal growth medium for animals cultivated in microtiter plates, but intense autofluorescence precluded further use (50). Ultimately, S Medium supplemented with antibiotics and E. coli (OP50) was used. Antibiotics were included to limit bacterial growth, which had a tendency to overgrow the cultures and kill the nematodes. Defining the optimal growth conditions, which vary depending on the length of the assay period and the number and condition of the animals, was important to developing a robust and reproducible assay.

The second major impediment to the routine use of C. elegans in HCS was the lack of systems that automated the time-consuming process of image acquisition, analysis and storage. This bottleneck is evident in the first series of relatively low-throughput and labor-intensive C. elegans drug screens (29, 30, 34, 51, 52). Compound effects were assessed by direct inspection of animals in microtiter plate wells using a stereomicroscope or of images captured by a CCD camera. Although sensitive for the detection of certain phenotypes, such as alterations in movement or morphology, manual inspection of plates or images is time consuming and tedious for HTS campaigns scaled for assaying hundreds-of-thousands of compounds (29, 30, 34). Moreover, operator fatigue increases variability and decreases specificity. An enzymatic assay that measures fluorescent substrate conversion in culture media can be automated, but the effects of compounds on the whole animal are lost (51). Recently, Moy et al., reported an automated high-throughput screen for novel antimicrobial compounds that protect C. elegans from a lethal dose of S. faecalis (32). While their automated screening assay was five-times faster than screening manually, the algorithm was limited to a simple yes-no (live-dead) assessment and was unable to the effects of compounds on individual animals. Taken together and as compared to established cell-based HCS protocols, these studies suggest that whole animal HCS was cumbersome and lacked the refinements in image acquisition and analysis to quantitatively assess compound effects on continuous physiological variables such as growth and development autophagy, misfolded protein disposition and cell permeability. In contrast, the HCS format of the invention could capture 5-channel multiparametric images of each well of microtiter plate using an automated inverted fluorescence microscope and image analysis software. Since the images were stored on a server, different algorithms could be applied at different times to extract various quantitative measures, such as fluorescent spot count, spot area or spot intensity per animal. These types of qualitative measures could never be assessed accurately manually, as the time required to count, for example, a dozen fluorescent spots in 35 animals in each well of a 384-well plate would rapidly fatigue even the most fastidious observer. In addition, imaging system use for data acquisition affected assay quality, which was improved by optimizing the microscope's autofocus and scanning times, and the degree of magnification used to scan the wells of 96-versus 384-well plates. The analysis algorithms, which control the fluorescence intensity cut-offs used to define fluorescent objects and must be empirically defined for each marker system, also had a significant impact on overall assay quality. By manipulating these parameters, Z'-factors were consistently obtained, which serves as a measure of assay quality, in the excellent range of 0.5 to 0.7, scores that rivaled those of the highest quality cell- or molecule-based HTS schemes (49). Based on these studies using transgenic animals expressing misfolded sGFP::ATZ, the ArrayScan VTI and the BioApplication programs possess the automation, speed and sensitivity to generate a high-quality assay that would permit the quantitative assessment of compound libraries on a continuous physiological variable, such as misfolded protein accumulation. Moreover, by optimizing the imaging analysis, the scanning time of a 384-well plate was reduced to ~30 minutes. Thus, ~6,000 compounds could be screened in a typical workday, or ~18,000 compounds per day if the ArrayScan VTI were configured with an automated plate loader. Screening using of compound effects on a discrete variable, such as a live-dead screen, would be even faster.

As a test of this C. elegans screening strategy, a limited drug screen was performed for compounds that affect accumulation of the misfolded human serpin, $\alpha$1-antitrypsin (sGFP::ATZ). Of the 6 compounds inducing a dose-dependant decrease in sGFP::ATZ accumulation, four (cantharidin, tamoxifen, fluphenazine and pimozide) belong to classes of drugs that were identified previously as enhancers of autophagy (53, 54)—a physiological process involved in the elimination of ATZ (55). Thus, the drug discovery strategy outlined herein has significant clinical import, as C. elegans has been used to model several protein misfolding disorders including Alzheimer's disease (56) and polyglutamine repeat disorders (57). Accordingly, live animal HCS for compounds that ameliorate disorders of proteostasis is feasible (58).

8. EXAMPLE: FLUPHENAZINE REDUCES ATZ IN HUMAN CELLS

Both Fluphenazine and Pimozide have a Dose-Dependent Effect on GFP+ inclusions in ATZ worms with almost complete elimination of the inclusions at 10 µM. These drugs also appear to be effective in reducing ATZ levels in the mammalian cell line model of AT deficiency, HTO/Z. An example for the effect of fluphenazine in HTO/Z cells is shown in FIG. 22. The cells were incubated for 48 hrs with fluphenazine in several different concentrations and then subjected to Western blot analysis for AT. The results show that fluphenazine mediates a dose-dependent decrease in insoluble ATZ levels. The effect is evident at doses of 1-10 µM. Interestingly this drug appears to lead to an increase in soluble ATZ with no significant change in levels of the control GAPDH. These data imply that the drug solely affects autophagic disposal of insoluble ATZ and that leads to more soluble ATZ. This is different from CBZ which appears to affect autophagic as well as proteasomal degradation.

9. REFERENCES

1. D. H. Perlmutter, Cell Death Differ. 16, 39 (2009).
2. D. A. Lomas, D. L. Evans, J. J. Finch, R. W. Carrell. Nature 357, 605 (1992).
3. J. K. Stoller, L. S. Aboussouan. Lancet 365, 2225 (2005).

4. M. J. Dycaico et al. Science 242, 1404 (1988).
5. J. A. Carlson et al J Clin Invest 83, 1193 (1989).
6. E. Piitulainen, J. A. Carlson, K. Ohlsson, T. Sveger, Chest 128, 2076 (2005).
7. D. Qu, J. H. Teckman, S. Omura, D. H. Perlmutter, J. Biol. Chem. 271, 22791 (1996).
8. E. D. Werner, J. L. Brodsky, A. A. McCracken. Proc Natl Acad Sci USA 26, 13797 (1996).
9. T. Kamimoto et al., J. Biol. Chem. 281, 4467 (2006).
10. K. B. Kruse, J. L. Brodsky, A. A. McCracken. Mol Biol Cell 17, 203 (2006).
11. T. Hidvegi, B. Z. Schmidt, P. Hale, D. H. Perlmutter. J Biol Chem 280, 39002 (2005).
12. T. Hidvegi et al J Biol Chem 282, 27769 (2007).
13. C. Haas and D. Selkoe, Nat. Rev. Mol. Cell Biol. 8, 101 (2007).
14. B. Boland et al., J Neurosci. 28, 6926 (2008).
15. R. Nixon, J. Cell Sci. 120, 4081 (2007).
16. F. Pickford et al., J. Clin. Invest. 118, 2190 (2008).
17. E. Cohen et al., Cell 139, 1157 (2009).
18. T. Hidvegi et al., Science 329, 229 (published Jun. 3, 2010 online as DOI:10.1126/science.1190354 and in print on Jul. 9, 2010; see also online supplement.)
19. R. Sifers, Science 329, 154 (Jul. 9, 2010)
20. J. A. Frearson and I. T. Collie, Drug discovery today 14 (23-24), 1150 (2009).
21. L. M. Mayr and D. Bojanic, Curr Opin Pharmacol 9 (5), 580 (2009).
22. K. H. Bleicher, H. J. Bohm, K. Muller et al., Nat Rev Drug Discov 2 (5), 369 (2003).
23. J. Hodgson, Nat Biotechnol 19 (8), 722 (2001).
24. M. P. Gleeson, Journal of medicinal chemistry 51 (4), 817 (2008).
25. P. Gleeson, G. Bravi, S. Modi et al., Bioorg Med Chem 17 (16), 5906 (2009).
26. K. A. Giuliano, J. R. Haskins, and D. L. Taylor, Assay Drug Dev Technol 1 (4), 565 (2003).
27. S. A. Haney, P. LaPan, J. Pan et al., Drug discovery today 11 (19-20), 889 (2006).
28. B. R. Stockwell, Nat Rev Genet 1 (2), 116 (2000).
29. J. Breger, B. B. Fuchs, G. Aperis et al., PLoS pathogens 3 (2), e18 (2007).
30. T. C. Kwok, N. Ricker, R. Fraser et al., Nature 441 (7089), 91 (2006).
31 G. Molina, A. Vogt, A. Bakan et al., Nat Chem Biol 5 (9), 680 (2009).
32. T. I. Moy, A. L. Conery, J. Larkins-Ford et al., ACS Chem Biol 4 (7), 527 (2009).
33. T. E. North, W. Goessling, C. R. Walkley et al., Nature 447 (7147), 1007 (2007).
34. M. Petrascheck, X. Ye, and L. B. Buck, Nature 450 (7169), 553 (2007).
35. J. Rihel, D. A. Prober, A. Arvanites et al., Science 327 (5963), 348 (2010).
36. T. C. Tran, B. Sneed, J. Haider et al., Cancer Res 67 (23), 11386 (2007).
37. P. B. Yu, C. C. Hong, C. Sachidanandan et al., Nat Chem Biol 4 (1), 33 (2008).
38. G. A. Silverman, C. J. Luke, S. R. Bhatia et al., Pediatric research 65 (1), 10 (2009).
39. S. Lee and B. J. Howell, Methods in enzymology 414, 468 (2006).
40. J. F. Morley, H. R. Brignull, J. J. Weyers et al., Proc Natl Acad Sci USA 99 (16), 10417 (2002).
41. J. J. Lum, R. J. DeBerardinis, and C. B. Thompson, Nat Rev Mol Cell Biol 6 (6), 439 (2005).
42. A. Melendez, Z. Talloczy, M. Seaman et al., Science 301 (5638), 1387 (2003).
43. C. Kang, Y. J. You, and L. Avery, Genes Dev 21 (17), 2161 (2007).
44. M. Driscoll and M. Chalfie, Nature 349 (6310), 588 (1991).
45. D. C. Royal, L. Bianchi, M. A. Royal et al., J Biol Chem 280 (51), 41976 (2005).
46. C. J. Luke, S. C. Pak, Y. S. Askew et al., Cell 130 (6), 1108 (2007).
47. K. Nehrke, J Biol Chem 278 (45), 44657 (2003).
48. D. H. Perlmutter, Journal of Clinical Investigation 110 (11), 1579 (2002).
49. J. H. Zhang, T. D. Chung, and K. R. Oldenburg, J Biomol Screen 4 (2), 67 (1999).
50. N. J. Szewczyk, E. Kozak, and C. A. Conley, BMC biotechnology 3, 19 (2003).
51. B. R. Ellerbrock, E. M. Coscarelli, M. E. Gurney et al., J Biomol Screen 9 (2), 147 (2004).
52. I. Okoli, J. J. Coleman, E. Tampakakis et al., PLoS ONE 4 (9), e7025 (2009).
53. A. Williams, S. Sarkar, P. Cuddon et al., Nat Chem Biol 4 (5), 295 (2008).
54. L. Zhang, J. Yu, H. Pan et al., Proc Natl Acad Sci USA 104 (48), 19023 (2007).
55. T. Kamimoto, S. Shoji, T. Hidvegi et al., Journal of Biological Chemistry 281 (7), 4467 (2006).
56. C. D. Link, Proc Natl Acad Sci USA 92 (20), 9368 (1995).
57. P. W. Faber, J. R. Alter, M. E. MacDonald et al., Proc Natl Acad Sci USA 96 (1), 179 (1999).
58. W. E. Balch, R. I. Morimoto, A. Dillin et al., Science 319 (5865), 916 (2008).
59. K. Nehrke and J. E. Melvin, J Biol Chem 277 (32), 29036 (2002).
60. P. A. Johnston, C. A. Foster, T. Y. Shun et al., Assay Drug Dev Technol 5 (3), 319 (2007).
61. P. A. Johnston, C. A. Foster, M. B. Tierno et al., Assay Drug Dev Technol 7 (3), 250 (2009).
62. P. A. Johnston, J. Phillips, T. Y. Shun et al., Assay Drug Dev Technol 5 (6), 737 (2007).
63. P. A. Johnston, K. M. Soares, S. N. Shinde et al., Assay Drug Dev Technol 6 (4), 505 (2008).
64. C. Brideau, B. Gunter, B. Pikounis et al., J Biomol Screen 8 (6), 634 (2003).
65. N. Malo, J. A. Hanley, S. Cerquozzi et al., Nat Biotechnol 24 (2), 167 (2006).

Various publications are cited herein, the contents of which are hereby incorporated by reference in their entireties.

We claim:
1. A *Caenorhabditis elegans* whose genome comprises a first transgene comprising: (a) a nucleic acid encoding a first fluorescent protein and (b) a nucleic acid encoding a human protein with a tendency to aggregate, or a polymerizable portion thereof, operably linked to a first *Caenorhabditis elegans* promoter, wherein said nucleic acid encoding a human protein with a tendency to aggregate, or a polymerizable portion thereof, comprises one or more synthetic introns resembling *Caenorhabditis elegans* introns, wherein said one or more synthetic introns comprise an AGGUAAGU splice acceptor sequence, a CAGG splice donor sequence, or both; wherein the human protein with a tendency to aggregate, or a polymerizable portion thereof, is fused with the first fluorescent protein and is expressed as a fusion protein, and wherein the expression of the fusion protein results in a detectable accumulation of the human protein in the *Caenorhabditis elegans*.

2. The *Caenorhabditis elegans* of claim 1, whose genome further comprises a second transgene comprising a marker construct comprising a marker gene encoding a marker protein operably linked to a second *Caenorhabditis elegans* promoter, wherein the expression of the transgene comprising the marker construct results in a single detectable region per *Caenorhabditis elegans*.

3. The *Caenorhabditis elegans* of claim 2, wherein the marker protein is a second fluorescent protein.

4. The *Caenorhabditis elegans* of claim 3, wherein the first fluorescent protein and the second fluorescent protein are not the same.

5. The *Caenorhabditis elegans* of claim 2, wherein the second *Caenorhabditis elegans* promoter is selected from the group consisting of a neuron-specific, a gut-specific promoter, a muscle-specific promoter, a pharynx-specific promoter and a tail-specific promoter.

6. The *Caenorhabditis elegans* of claim 5, wherein the second *Caenorhabditis elegans* promoter is selected from the group consisting of a pharynx-specific promoter and a tail-specific promoter.

7. The *Caenorhabditis elegans* of claim 1, wherein the protein is selected from the group consisting of huntingtin, synuclein, neuroserpin, ubiquitin, neurofilament protein, alpha B crystallin, and tau.

8. The *Caenorhabditis elegans* of claim 1, wherein the first *Caenorhabditis elegans* promoter is selected from the group consisting of a neuron-specific promoter, a gut-specific promoter, a muscle-specific promoter, a pharynx-specific promoter and a tail-specific promoter.

9. The *Caenorhabditis elegans* of claim 1, wherein the nucleic acid encodes an a1-antitrypsin mutant protein selected from the group consisting of ATZ, Siiyama and Mmalton, and wherein said first *Caenorhabditis elegans* promoter is a gut specific promoter.

10. The *Caenorhabditis elegans* of claim 1, wherein the one or more synthetic intron is between 48 and 51 base pairs in length.

11. The *Caenorhabditis elegans* of claim 1, wherein the protein is amyloid beta or a polymerizable portion thereof.

12. The *Caenorhabditis elegans* of claim 1, wherein the protein is synuclein or a polymerizable portion thereof.

13. The *Caenorhabditis elegans* of claim 1, wherein the protein is huntingtin or a polymerizable portion thereof.

14. The *Caenorhabditis elegans* of claim 1, wherein the protein is tau protein or a polymerizable portion thereof.

15. The *Caenorhabditis elegans* of claim 1, wherein the protein is neuroserpin or a polymerizable portion thereof.

16. The *Caenorhabditis elegans* of claim 1, wherein the protein is an a1-antitrypsin mutant protein selected from the group consisting of ATZ, Siiyama and Mmalton, or a polymerizable portion thereof.

* * * * *

UNITED STATES PATENT AND TRADEMARK OFFICE
CERTIFICATE OF CORRECTION

PATENT NO. : 9,844,605 B2
APPLICATION NO. : 14/335413
DATED : December 19, 2017
INVENTOR(S) : Stephen C. Pak et al.

It is certified that error appears in the above-identified patent and that said Letters Patent is hereby corrected as shown below:

In the Specification

Please correct the paragraph in Column 1, Lines 17-19 as follows:
-- This invention was made with government support under grant numbers DK079806 and CA087006 awarded by the National Institutes of Health. The government has certain rights in the invention. --

Signed and Sealed this
Eleventh Day of December, 2018

Andrei Iancu
*Director of the United States Patent and Trademark Office*